US009809809B2

(12) United States Patent
Schmidt et al.

(10) Patent No.: US 9,809,809 B2
(45) Date of Patent: *Nov. 7, 2017

(54) NEUROTOXINS EXHIBITING SHORTENED BIOLOGICAL ACTIVITY

(71) Applicant: MERZ PHARMA GmbH & CO. KGaA, Frankfurt am Main (DE)

(72) Inventors: Michael Schmidt, Potsdam (DE); Jurgen Frevert, Berlin (DE); Fred Hofmann, Potsdam (DE); Gerhard Groer, Potsdam (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 87 days.

This patent is subject to a terminal disclaimer.

(21) Appl. No.: 14/356,449

(22) PCT Filed: Nov. 8, 2012

(86) PCT No.: PCT/EP2012/072158
§ 371 (c)(1),
(2) Date: May 6, 2014

(87) PCT Pub. No.: WO2013/068476
PCT Pub. Date: May 16, 2013

(65) Prior Publication Data
US 2014/0308267 A1 Oct. 16, 2014

Related U.S. Application Data

(60) Provisional application No. 61/628,911, filed on Nov. 9, 2011, provisional application No. 61/659,137, filed on Jun. 13, 2012.

(30) Foreign Application Priority Data

Nov. 9, 2011 (EP) .................................... 11188440
Jun. 13, 2012 (EP) .................................... 12171801

(51) Int. Cl.
*C12N 9/52* (2006.01)
*C07K 14/47* (2006.01)
*A61K 38/48* (2006.01)

(52) U.S. Cl.
CPC ............ *C12N 9/52* (2013.01); *A61K 38/4893* (2013.01); *C07K 14/4746* (2013.01); *C12Y 304/24069* (2013.01)

(58) Field of Classification Search
CPC .............................. C12N 9/52; C07K 14/4746
See application file for complete search history.

(56) References Cited

U.S. PATENT DOCUMENTS

| 2002/0058294 A1* | 5/2002 | Poli ..................... C07K 16/1282 435/7.32 |
| 2009/0117587 A1* | 5/2009 | Stanker ............... C07K 16/1282 435/7.1 |
| 2010/0015116 A1* | 1/2010 | Oyler ....................... C12N 9/93 424/94.1 |
| 2010/0278826 A1* | 11/2010 | Shoemaker ........ C07K 16/1282 424/134.1 |

FOREIGN PATENT DOCUMENTS

| FR | 2924721 | 6/2009 |
| WO | WO 9847919 | 10/1998 |
| WO | WO 2009/014854 | 1/2009 |
| WO | WO 2009/080981 | 7/2009 |
| WO | WO2009080981 | * 7/2009 ........... G01N 33/573 |

OTHER PUBLICATIONS

Tsai et al., 2010, Targeting botulinum neurotoxin persistence by the ubiquitin-proteasome system, PNAS, 107(38): 16554-16559.*
Aoki, K. R., A comparison of the safety margins of botulinum neurotoxin serotypes A, B, and F in mice. Toxicon, 39, 2001, pp. 1815-1820.
Chen, F., et al., Biophysical characterization of the stability of the 150-kilodalton botulinum toxin, the nontoxic component, and the 900-kilodalton botulinum toxin complex species. Infection and Immunity, vol. 66, No. 6, Jun. 1998, pp. 2420-2425.
Couesnon, A., et al., Expression of botulinum neurotoxins A and E, and associated non-toxin genes, during the transition phase and stability at high temperature: analysis by quantitative reverse transcription-PCR. Microbiology, 2006, vol. 152, pp. 759-770.
Dressler, D., et al., Mouse diaphragm assay for detection of antibodies against botulinum toxin type B. Movement disorders, vol. 20, No. 12, 2005, pp. 1617-1619.
Eleopra, R., et al., Botulinum neurotoxin serotype C: a novel effective botulinum toxin therapy in humn, Neuroscience Letters, vol. 224, 1997, pp. 91-94.
Eleopra, R., et al., Different time courses of recovery after poisoning with botulinum neurotoxin serotypes A and E in humans. Neuroscience Letters, vol. 256, 1998, pp. 135-138.

(Continued)

*Primary Examiner* — Amber D Steele
(74) *Attorney, Agent, or Firm* — Hueschen and Sage

(57) ABSTRACT

The present invention relates to the pharmaceutical field. Specifically, it contemplates a polynucleotide encoding a neurotoxin polypeptide exhibiting a reduced duration of the biological effect in a subject, wherein said polypeptide comprises at least one E3 ligase recognition motif in the light chain, wherein said E3 ligase recognition motif is preferably a binding motif for the E3 ligase MDM2. The invention further pertains to polypeptides encoded by the polynucleotide of the invention as well as polypeptides comprising one or more amino acid substitutions. Further encompassed by the present invention are vectors and host cells comprising the said polynucleotide, polypeptides encoded thereby and antibodies specifically binding to the polypeptides. Moreover, the invention relates to medicaments comprising said polynucleotides and polypeptides, as well as specific therapeutic applications thereof. Furthermore, the present invention contemplates methods for the manufacture of the polypeptides and medicaments.

17 Claims, 8 Drawing Sheets

(56) References Cited

OTHER PUBLICATIONS

Figure 1:
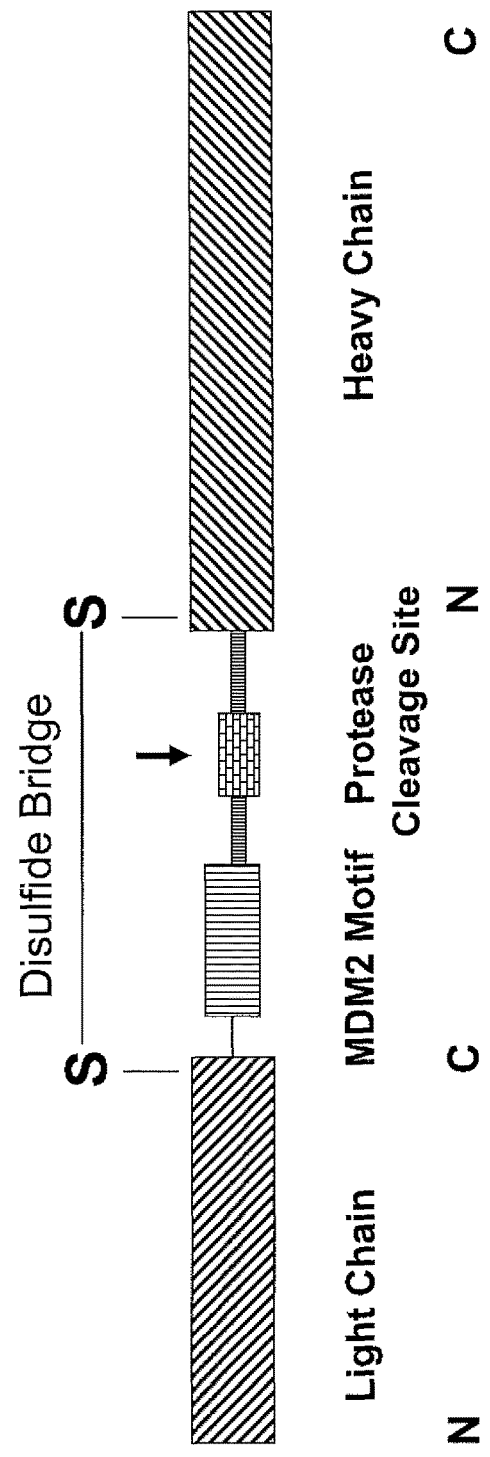

Fischer, A., et al., Single molecule detection of intermediates during botulinum neurotoxin translocation across membranes. PNAS, Jun. 19, 2007, vol. 104, No. 25, pp. 10447-10452.
Foran, P/G., et al., Evaluation of the therapeutic usefulness of botulinum neurotoxin B, C1, E, and F compared with the long lasting type A: Basis for distinct durations of inhibition of exocytosis in central neurons. The Journal of Biological Chemistry, vol. 278, No. 2, Jan. 10, 2003, pp. 1363-1371.
International Preliminary Report on Patentability for PCT/EP2012/072158 dated May 22, 2014.
Jost, W. H., et al., Botulinum neurotoxin type A free of complexing proteins (XEOMIN) in focal dystonia. Drugs, 2007, 67(5), pp. 669-683.
Keller, J.E., Recovery from botulinum neurotoxin poisoning in vivo. Neuroscience, vol. 139, 2006, pp. 629-637.
Krieglstein, K. G., et al., Covalent structure of botulinum neurotoxin type A: Location of sulfhydryl groups, and disulfide bridges and identification of C-termini of light and heavy chains. Journal of Protein Chemistry, vol. 13, No. 1, 1994, pp. 49-57.
Krieglstein, K., et al., Arrangement of disulfide bridges and positions of sulfhydryl groups in tetanus toxin. Eur. J. Biochem., 1990, vol. 188, pp. 39-45.
Krieglstein, K.G., et al., Limited proteolysis of tetanus toxin. Eur. J. Biochem., 1991, vol. 202, pp. 41-51.
Marmor, M. D., et al., Role of protein ubiquitylation in regulating endocytosis of receptor tyrosine kinases. Oncogene, 2004, vol. 23, pp. 2057-2070.
Pearce, L. B., et al., Measurement of botulinum toxin activity: Evaluation of the lethality assay. Toxicology and Applied Pharmacology, vol. 128, 1994, pp. 69-77.
Schrader, E. K., et al., Targeting proteins for degradation. Nature Chemical Biology, vol. 5, No. 11, Nov. 2009, pp. 815-822.
Sloop, R. R., et al., Human response to botulinum toxin injection: Type B compared with type A. Neurology, vol. 49, Jul. 1997, pp. 189-194.
Torii, Y., et al., Comparison of effects of botulinum toxin subtype A1 and A2 using twitch tension assay and rat grip strength test. Toxicon vol. 57, 2011, pp. 93-99.
Washbourne, P., et al., On the action of botulinum neurotoxins A and E at cholinergic terminals. J. Physiology (Paris), 1998, vol. 92, pp. 135-139.
Whitemarsh, R.C.M., et al., Novel application of human neurons derived from induced pluripotent stem cells for highly sensitive botulinum neurotoxin detection. Toxicological Sciences, 126(2), Jan. 2012, pp. 426-435.
International Search Report for PCT/EP2012/072158 of Dec. 11, 2012.
Kuo, Chueh-Ling, et al., "Accelerated neuronal cell recovery from Botulinum neurotoxin intoxication by targeted ubiquitination", PLoS ONE May 2011, vol. 6, issue 5, e20352, pp. 1-10.
Shimizu, Harumi, et al., "The conformationally flexible S9-S10 linker region in the core domain of p53 contains a novel MDM2 binding site whose mutation increases ubiquitination of p53 in vivo", The Journal of Biological Chemistry, vol. 277, No. 32, Issue of Aug. 9, 2002, pp. 28446-28458.
Ohno, Susumu, et al., "Antigen-binding specificities of antibodies are primarily determined by seven residues of VH", Proc. Natl. Acad. Sci, USA, May 1985, vol. 82, pp. 2945-2949, Immunology.
Rudikoff, Stuart, et al., "Single amino acid substitution altering antigen-binding specificity", Proc. Natl. Acad. Sci. USA, Mar. 1982. vol. 79, pp. 179-1983, Immunology.

\* cited by examiner

Fig. 3

| Q27 | E28 | Q53 | N72 | N378 | N379 | V382 | N383 | L391 | R394 | T400 | SEQ ID NO.: | Comparison with BoNT/E-MDM2 (SEQ ID NO. 52) |
|---|---|---|---|---|---|---|---|---|---|---|---|---|
|  |  | X | X | X | X |  |  |  | X | X | 57 | Reduced duration of biological effect |
|  |  | X | X |  |  |  |  |  | X | X | 64 | no effect |
|  |  |  | X |  |  |  |  |  | X | X | 60 | no effect |
|  |  | X |  | X | X |  |  |  | X |  | 63 | no effect |
|  |  |  |  | X | X |  |  |  |  |  | 58 | Reduced duration of biological effect |
|  |  |  |  | X | X |  |  |  |  |  | 66 | no effect |
|  |  |  |  | X |  |  |  |  |  |  | 65 | no effect |
|  |  |  |  | X | X |  |  |  |  |  | 76 | no effect |
|  |  |  |  | X | X |  |  |  | X |  | 74 | no effect |
|  |  |  | X | X | X |  |  |  |  |  | 61 | Reduced duration of biological effect |
|  |  |  |  | X | X |  |  |  |  | X | 75 | Reduced duration of biological effect |
| X | X |  |  |  |  |  |  |  |  |  | 53 | no effect |
| X | X |  |  |  |  |  |  |  |  |  | 54 | no effect |
| X | X |  | X |  |  |  |  |  |  |  | 55 | no effect |
|  |  |  |  | X | X | X |  |  |  |  | 67 | no effect |
|  |  |  |  | X | X |  |  | X |  |  | 73 | no effect |
|  |  |  |  | X | X |  | X |  |  |  | 71 | n.d. |
|  |  |  |  | X | X | X | X |  |  |  | 68 | n.d. |
|  |  |  |  | X | X | X |  | X |  |  | 70 | n.d. |
|  |  |  |  | X | X |  | X | X |  |  | 72 | n.d. |
|  |  |  |  | X | X | X | X | X |  |  | 69 | n.d. |
|  |  | X | X | X | X |  |  |  |  | X | 56 | n.d. |
|  |  | X |  | X | X |  |  |  |  | X | 62 | n.d. |
|  |  | X | X | X | X |  |  |  |  | X | 59 | n.d. |
|  |  |  |  | X | X |  |  |  |  | X | 77 | n.d. |

NEUROTOXINS EXHIBITING SHORTENED BIOLOGICAL ACTIVITY

The present invention relates to the pharmaceutical field. Specifically, it contemplates a polynucleotide encoding a neurotoxin polypeptide exhibiting a reduced duration of the biological effect in a subject, wherein said polypeptide comprises at least one E3 ligase recognition motif in the light chain, wherein said E3 ligase recognition motif is preferably a binding motif for the E3 ligase MDM2. The invention further pertains to polypeptides encoded by the polynucleotides of the invention as well as polypeptides comprising one or more amino acid substitutions. Further encompassed by the present invention are vectors and host cells comprising the said polynucleotides, polypeptides encoded thereby and antibodies specifically binding to the polypeptides. Moreover, the invention relates to medicaments comprising said polynucleotides and polypeptides, as well as specific therapeutic applications thereof. Furthermore, the present invention contemplates methods for the manufacture of the polypeptides and medicaments.

*Clostridium botulinum* and *Clostridium tetani* produce highly potent neurotoxins, i.e. *botulinum* toxins (BoNTs) and tetanus toxin (TeNT), respectively. These Clostridial neurotoxins (CNTs) specifically bind to neuronal cells and disrupt neurotransmitter release. Each toxin is synthesized as an inactive unprocessed approximately 150 kDa single-chain protein. The posttranslational processing involves formation of disulfide bridges, and limited proteolysis (nicking) by the bacterial protease(s). Active neurotoxin consists of two chains, an N-terminal light chain of approx. 50 kDa and a heavy chain of approx. 100 kDa linked by a disulfide bond. CNTs consist of three domains, i.e. the catalytic light chain, the heavy chain encompassing the translocation domain (N-terminal half) and the receptor binding domain (C-terminal half), see Krieglstein 1990, Eur. J. Biochem. 188, 39; Krieglstein 1991, Eur. J. Biochem. 202, 41; Krieglstein 1994, J. Protein Chem. 13, 49. The *Botulinum* neurotoxins are synthesized as molecular complexes comprising the 150 kDa neurotoxin protein and associated non-toxic, complexing proteins. The complex sizes differ based on the Clostridial strain and the distinct neurotoxin serotypes ranging from 300 kDa to 900 kDa. The complexing proteins in these complexes stabilize the neurotoxin and protect it against degradation, see Chen 1998, Infect. Immun. 66 (6): 2420-2425.

*Clostridium botulinum* secretes seven antigenically distinct serotypes designated A to G of the *botulinum* neurotoxin (BoNT). All serotypes together with the related tetanus neurotoxin (TeNT) secreted by *Clostridium tetani*, are $Zn^{2+}$-endoproteases that block synaptic exocytosis by cleaving SNARE proteins, see Couesnon, 2006, Microbiology, 152, 759. BoNTs cause the flaccid muscle paralysis seen in botulism, see Fischer 2007, PNAS 104, 10447.

Despite its toxic effects, *Botulinum* toxins have been used as therapeutic agents for a large number of diseases or disorders. *Botulinum* toxin serotype A was approved for human use in the United States in 1989 for the treatment of strabism, blepharospasm, and other disorders. It is commercially available as a *Botulinum* A neurotoxin with complexing proteins, for example, under the tradename BOTOX (Allergan Inc.) or under the tradename DYSPORT (Ipsen Ltd.). An improved, complex-free neurotoxin A polypeptide preparation is available under the tradename XEOMIN (Merz Pharmaceuticals LLC). The effect of *Botulinum* toxin is only temporary, which is the reason why repeated administration of *Botulinum* toxin may be required to maintain a therapeutic effect.

The Clostridial neurotoxins weaken voluntary muscle strength and are effective therapeutics for strabism, focal dystonia, including cervical dystonia, and benign essential blepharospasm. They have been further shown to relief hemifacial spasm, and focal spasticity, and, moreover, to be effective in a wide range of other indications, such as gastrointestinal disorders, hyperhidrosis, and cosmetic wrinkle correction, see Jost 2007, Drugs 67, 669.

However, weakening muscle strengths and contraction is also desirable for medical conditions or disease such as wound healing, immobilisation for bone and tendon fracture treatment, post surgery immobilization, specifically in connection with haemorrhoidectomy, introduction of dental implants, or hip joint replacement (endoprothesis), knee arthroplasty, ophthalmological surgery, acne, irritable bowel disease, vaginism, lower back pain, or benign prostate hyperplasia. The neurotoxins usually exhibit their biological effect over a time period which is longer than actually needed for efficient treatment of said diseases or conditions. A prolonged muscle paralysis is, however, detrimental or at least less preferable in the therapy of the said medical conditions or diseases. Neurotoxins exhibiting their biological effect only over the desired time period are, however, not yet available.

Accordingly, the technical problem underlying the present invention can be seen as the provision of means and methods for complying with the aforementioned needs. The technical problem is solved by the embodiments characterized in the claims and herein below.

The present invention, accordingly, relates to a polynucleotide encoding a neurotoxin polypeptide exhibiting a reduced duration of the biological effect in a subject, wherein said polypeptide comprises at least one E3 ligase recognition motif in the light chain, wherein said E3 ligase recognition motif is preferably a binding motif for the E3 ligase MDM2. The reduced duration of the biological activity of a, thus, modified polypeptide has been exemplified for BoNT/E-MDM2. In addition, said neurotoxin polypeptide has been further optimized by site-directed mutagenesis of specific amino acid residues in the light chain. To this end, exposed amino acid residues in the neurotoxin light chain located in spatial proximity to the introduced E3 ligase MDM2 recognition motif have been identified by three-dimensional structural analysis. Subsequently, the identified exposed amino acid residues in the neurotoxin light chain have been substituted by lysine residues. This optimization approach resulted in an even faster degradation of the mutated BoNT/E-MDM2 polypeptides, in comparison to non-mutated BoNT/E-MDM2 polypeptides, as demonstrated in the following Examples.

Accordingly, such modified or mutated neurotoxin polypeptides of the invention are particularly useful for therapy of diseases which require a short or reduced duration of the biological effect of a neurotoxin.

The term "polynucleotide" as used herein refers to single- or double-stranded DNA molecules as well as to RNA molecules. Encompassed by the said term is genomic DNA, cDNA, hnRNA, mRNA as well as all naturally occurring or artificially modified derivatives of such molecular species. The polynucleotide may be, in an aspect, a linear or circular molecule. Moreover, in addition to the nucleic acid sequences encoding the aforementioned neurotoxin polypeptide, a polynucleotide of the present invention may comprise additional sequences required for proper transcription and/or translation such as 5' or 3' UTR sequences. The polynucleotide of the present invention encodes a modified neurotoxin polypeptide derivable from one of the antigenically different serotypes of Botulinum neurotoxins, i.e. BoNT/A, BoNT/B, BoNT/C1, BoNT/D, BoNT/E, BoNT/F, BoNT/G, or Tetanus neurotoxin (TeNT). In an aspect of the present invention, the said polynucleotide comprises (prior to the modification of the invention, i.e. modification of the light chain by at least one E3 ligase recognition motif) a nucleic acid sequence as shown in SEQ ID NO: 1 (BoNT/A), SEQ ID NO: 3 (BoNT/B), SEQ ID NO: 5 (BoNT/C1), SEQ ID NO: 7 (BoNT/D), SEQ ID NO: 9 or 81 (BoNT/E), SEQ ID NO: 11 (BoNT/F), SEQ ID NO: 13 (BoNT/G) or SEQ ID NO: 15 (TeNT). Moreover, encompassed is, in an aspect, a polynucleotide comprising a nucleic acid sequence encoding an amino acid sequence (prior to the modification of the invention, i.e. modification of the light chain by at least one E3 ligase recognition motif) as shown in any one of SEQ ID NO: 2 (BoNT/A), SEQ ID NO: 4 (BoNT/B), SEQ ID NO: 6 (BoNT/C1), SEQ ID NO: 8 (BoNT/D), SEQ ID NO: 10 or 82 (BoNT/E), SEQ ID NO: 12 (BoNT/F), SEQ ID NO: 14 (BoNT/G) or SEQ ID NO: 16 (TeNT). In another aspect, the said polynucleotide is a variant of the aforementioned polynucleotides comprising one or more nucleotide substitutions, deletions and/or additions which in still another aspect may result in an encoded amino acid having one or more amino acid substitutions, deletions and/or additions. Moreover, a variant polynucleotide of the invention shall in another aspect comprise a nucleic acid sequence variant being at least 40%, at least 50%, at least 60%, at least 70%, at least 75%, at least 80%, at least 85%, at least 90%, at least 95%, at least 96%, at least 97%, at least 98%, at least 99% identical or 100% identical to the nucleic acid sequence as shown in any one of SEQ ID NOs: 1, 3, 5, 7, 9, 81, 11, 13 or 15 or a nucleic acid sequence variant which encodes an amino acid sequence being at least 40%, at least 50%, at least 60%, at least 70%, at least 75%, at least 80%, at least 85%, at least 90%, at least 95%, at least 96%, at least 97%, at least 98%, at least 99% identical or 100% identical to the amino acid sequence as shown in any one of SEQ ID NOs: 2, 4, 6, 8, 10, 82, 12, 14, or 16. In an aspect, each of the aforementioned variant polynucleotides encodes a variant polypeptide retaining one or more biological properties and, in another aspect, all of the biological properties of the respective neurotoxin polypeptide, i.e. the BoNT/A, BoNT/B, BoNT/C1, BoNT/D, BoNT/E, BoNT/F, BoNT/G or Tetanus neurotoxin (TeNT). Those of skill in the art will appreciate that full biological activity is maintained only after proteolytic activation, even though it is conceivable that the unprocessed precursor can exert some biological functions or be partially active. The term "biological properties" as used herein refers to (a) receptor binding, (b) internalization, (c) translocation across the endosomal membrane into the cytosol, and/or (d) endoproteolytic cleavage of proteins involved in synaptic vesicle membrane fusion. In a further aspect, the variant polynucleotides can encode variant polypeptides having improved or altered biological properties, e.g., they may comprise cleavage sites which are improved for enzyme recognition or may be improved for receptor binding or any other property specified above. In yet a further aspect, the variant polynucleotides shall encode fusion neurotoxin polypeptides comprising a part of at least two neurotoxin polypeptides of different serotypes, e.g., a fusion neurotoxin comprising a heavy chain of BoNT/A and a light chain of BoNT/E or a binding domain of BoNT/E and the translocation domain and a light chain of BoNT/A.

The term "identical" as used herein refers to sequence identity characterized by determining the number of identical amino acids between two nucleic acid sequences or amino acid sequences wherein the sequences are aligned so that the highest order match is obtained. It can be calculated using published techniques or methods codified in computer programs such as, for example, BLASTP, BLASTN or FASTA (Altschul 1990, J. Mol. Biol. 215, 403). The percent identity values are, in one aspect, calculated over the entire amino acid sequence. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS 5, 151) or the programs Gap and BestFit (Needleman 1970, J. Mol. Biol. 48; 443; Smith 1981, Adv. Appl. Math. 2, 482), which are part of the GCG software packet (Genetics Computer Group 1991, 575 Science Drive, Madison, Wisconsin, USA 53711), may be used. The sequence identity values recited above in percent (%) are to be determined, in another aspect of the invention, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

The term "activity", "function", "biological activity", "biological function", or "biological effect" of a neurotoxin as used herein denotes the amount of cellular exocytosis inhibited from a cell per unit of time, such as exocytosis of a neurotransmitter, e.g. acetylcholine, from a target cell, such as a neuron. More specifically, it refers to the biological activity of a mature di-chain neurotoxin polypeptide exhibiting a) receptor binding, b) internalization, c) translocation across the endosomal membrane into the cytosol, and/or d) endoproteolytic cleavage of proteins involved in synaptic vesicle fusion. The term "duration of the biological effect (of the neurotoxin) in a subject" as used herein means the time period of the biological activity of a neurotoxin in a subject to which the neurotoxin has been applied. In vivo assays for assessing biological activity include the mouse LD50 assay and the ex vivo mouse hemidiaphragm assay as described by Pearce et al. (Pearce 1994, Toxicol. Appl. Pharmacol. 128: 69-77) and Dressler et al. (Dressler 2005, Mov. Disord. 20:1617-1619, Keller 2006, Neuroscience 139: 629-637). The biological activity can also be assessed by a cell-based assay as described, e.g., by Whitemarsh et al. (Whitemarsh et al. 2012, Toxicol. Sci. 126: 426-435). The biological activity is commonly expressed in Mouse Units (MU). As used herein, 1 MU is the amount of neurotoxic component, which kills 50% of a specified mouse population after intraperitoneal injection, i.e. the mouse i.p. LD50. The term "subject" as used herein means a mammal, preferably a human.

Moreover, fusion polypeptides further comprising detectable marker peptides or tags are encompassed in further aspects of the neurotoxin polypeptide of the invention exhibiting a reduced duration of the biological effect in a subject, due to the at least one E3 ligase recognition motif in the light chain. In one aspect, suitable tags are, e.g., FLAG-tags, Myc-tags, His-tags, HA-tags or GST-tags which also allow for a more efficient purification of the tagged polypeptides. Detectable marker peptides, in an aspect, include fluorescent proteins such as GFP, BFP, YFP and the like. Said fusion polypeptides can comprise additional polypeptide domains in some aspects. For example, the neurotoxin polypeptide of the invention can comprise a peptide domain which mediates cell penetration in order to access the site of action of the neurotoxin light chain, i.e. the cytoplasm of a neuronal target cell. For this purpose, e.g., a poly-arginine peptide can be used for fusion to the neurotoxin polypeptide of the invention which is well known in the art.

introduced into the sequence between the two cysteines forming the disulfide bridge between heavy and light chain, preferably into a linker as defined elsewhere herein.

TABLE 1

Neurotoxins and proteolytic cleavage sites which can be used to form the active di-chain molecule

| Neurotoxin (Bacterial Strain) | Accession number | Cleavage site(s) | Native light chain | Sequence including cysteines forming disulfide bridge and cleavage sites (highlighted) |
|---|---|---|---|---|
| BoNT/A (Hall/62A) | ABD 65472 | K438/T439 K448/A449 | M1-K438 | KLLCVRGIITSK . . . TKSLDKGYNK . . . ALN . . . DLCIKV (SEQ ID NO: 17) |
| BoNT/B (Okra) | BAE 48264 | K441/A442 | M1-K441 | IQMCKSVK . . . APGCIDV (SEQ ID NO: 18) |
| BoNT/C1 (C-6814) | BAA 89713 | R444/S445 K449/T450 | M1-R444 | TKFCHKAIDGR . . . SYNK . . . TLDCRELLV (SEQ ID NO: 19) |
| BoNT/D | BAA 90661 | K442/N443 R445/D446 | M1-K442 | TKVCLRLTK . . . NSR . . . DDSTCIKV (SEQ ID NO: 20) |
| BoNT/E (Beluga) | CAA 43999 | K419/G420 R422/K423 | M1-K419 | IRFCKNIVSVK . . . G . . . IRKSICIEI (SEQ ID NO: 21) |
| BoNT/F (NCTC10281) | CAA 73972 | R435/K436 K439/A440 | M1-R435 | VKFCKSVIPRK . . . GTK . . . APPRLCIRV (SEQ ID NO: 22) |
| BoNT/G | CAA 52275 | K446/S447 | M1-K446 | IAMCKPVMYKNTGK . . . SEQCIIV (SEQ ID NO: 23) |
| TeNT | P 04958 | R449 (R455) | M1-A457 | IGLCKKIIPPTNIR . . . ENLYNR . . . TASLTDLGGELCIKI (SEQ ID NO: 24) |

The neurotoxin polypeptide (encoded by the polynucleotide) of the invention further comprises at least one E3 ligase recognition motif in its light chain. As set forth elsewhere herein in more detail and as demonstrated in the following Examples, the duration of the biological effect of a neurotoxin in a subject can be influenced, i.e. altered, by the incorporation of at least one E3 ligase recognition motif into the light chain or the addition of at least one E3 ligase recognition motif to the N- or C-terminus of the light chain. Thus, in one aspect, the neurotoxin polypeptide of the invention comprises at least one internally or terminally introduced E3 ligase recognition motif in the light chain. Such a modification results in a reduced duration of the biological effect of the neurotoxin of the invention in a subject, in comparison to a neurotoxin not comprising an E3 ligase recognition motif. In an aspect of the invention, the said light chain of the neurotoxin polypeptide encoded by the polynucleotide of the invention is obtained by modification from a light chain being encoded by a polynucleotide comprising any one of the aforementioned specific nucleic acid sequences or variants thereof described above. As described above and well known in the art, the light chains of the neurotoxin polypeptides are generated by proteolytic cleavage of a precursor polypeptide. The light chain is the N-terminal portion of the precursor polypeptide which is obtained as a result of said proteolytic cleavage. The amino acid sequences of the light chains of the neurotoxin polypeptides referred to above can be deduced, in an aspect, from the cleavage sites of the wild type neurotoxins indicated in Table 1. In recombinant neurotoxins, cleavage sites (such as a thrombin cleavage site or enterokinase cleavage site) are The term "E3 ligase recognition motif" as used herein refers to (a) modification(s) of the light chain of the neurotoxin polypeptide of the invention which result in accelerated degradation of said neurotoxin polypeptide by endogenous degradation pathways present in the subject to which the neurotoxin has been applied. The E3 ligase recognition motif is a structural motif which allows recognition of the motif and binding to the motif of an E3 ligase. Further peptide degradation signals mediating cellular degradation of proteins are known in the art, and comprise, for example, PEST motifs, WW motifs, or WD40 motifs.

The degradation pathway can be a proteasomal degradation pathway or a lysosomal degradation pathway. In another aspect, a degradation pathway may merely result in a partial degradation of the neurotoxin polypeptide of the invention, e.g., by one or more proteolytic cleavage steps. The said E3 ligase recognition motif can be introduced into the light chain, i.e. be located (internally) within the light chain or linked thereto either N- or C-terminally. In the latter case, a neurotoxin polypeptide of the invention can, for example, carry an E3 ligase recognition motif which is interposed between the neurotoxin light chain and the neurotoxin heavy chain. For example, such a construct may in one aspect have the arrangement, from the N-terminus to the C-terminus: Neurotoxin light chain-E3 ligase recognition motif-neurotoxin heavy chain. Alternatively, the domain arrangement can be, from the N- to the C-terminus: Neurotoxin heavy chain-E3 ligase recognition motif-neurotoxin light chain. In a further aspect, an additional linker, such as, e.g., a poly-Glycine linker, may be used to interconnect said neurotoxin light and heavy chain. Such a construct may be arranged, from the N- to the C-terminus: Neurotoxin light chain-E3 ligase recognition motif-linker-neurotoxin heavy chain. Alternatively, the domain arrangement can be, from the N- to the C-terminus: Neurotoxin heavy chain-linker-E3 ligase recognition motif-neurotoxin light chain. The linker preferably comprises a protease cleavage site, for instance, an enterokinase cleavage site or a thrombin cleavage site. The position of the E3 ligase recognition motif is preferably C-terminal of the first disulfide bridge-forming cysteine of the light chain and N-terminal of the protease cleavage site; see FIG. 1. Upon cleavage by the respective protease, the neurotoxin light chain (comprising the E3 ligase recognition motif) is released from the above-mentioned construct. In other aspects, the neurotoxin polypeptide of the invention comprises not only one E3 ligase recognition motif in or attached to the native recombinant light chain, but two, three, four or even more E3 ligase recognition motifs. The term "modified" neurotoxin polypeptide exhibiting a reduced duration of the biological effect in a subject as used herein means that the neurotoxin polypeptide of the invention comprises at least one E3 ligase recognition motif in or attached to the native recombinant light chain, preferably in combination with one or more mutations in the neurotoxin light chain. Even more preferred, said mutation in the neurotoxin light chain is an amino acid substitution as defined elsewhere herein.

The person skilled in the art is well aware of suitable E3 ligase recognition motifs and how to introduce or link them to the neurotoxin polypeptide' s light chain. Moreover, the skilled artisan can generate polynucleotides encoding such neurotoxin polypeptides with the at least one E3 ligase recognition motif by applying recombinant molecular biological techniques or chemical modifications. For example, site directed mutagenesis may be used for introducing the E3 ligase recognition motifs referred to herein. Alternatively, a nucleic acid sequence for the polynucleotide comprising the coding sequences for the neurotoxin polypeptide and the envisaged E3 ligase recognition motif may be designed and the entire polynucleotide may subsequently be chemically synthesised.

In one aspect, the said E3 ligase recognition motif is at least one internally or terminally introduced E3 ligase-recognition and/or E3 ligase-binding motif. Preferably, the recognition and binding motif for a respective E3 ligase is identical, i.e. said motif is used both for recognition and binding of the E3 ligase. In this aspect, the E3 ligase recognition motif targets the neurotoxin polypeptide's light chain of the invention to cellular degradation via the ubiquitin-mediated proteasome degradation pathway. Degradation via the ubiquitin-proteasome pathway involves two discrete and successive steps: (i) covalent attachment of multiple ubiquitin molecules to the neurotoxin polypeptide's light chain of the invention to form a poly-ubiquitin chain and (ii) degradation of the, thus, tagged neurotoxin polypeptide's light chain of the invention by the 26S proteasome pathway. As described in the art, ubiquitin, a highly conserved 76-amino acid protein, is conjugated to the target protein by a three-step mechanism. Initially, the C-terminal carboxyl group of ubiquitin is activated by an ubiquitin-activating enzyme (E1). The thioester formed by attachment of ubiquitin to the E1 enzyme is then transferred through a trans-acylation reaction to an ubiquitin-conjugating enzyme (E2). Depending on the E3 ligase involved, the ubiquitin is then either directly transferred to the E3 ligase (HECT E3 ligases) or the E2-ubiquitin complex binds to the E3 ligase (RING E3 ligases). Finally, in both cases the E3 ligase binds specifically to the substrate and catalyses the last step in the conjugation process, which is the covalent attachment of ubiquitin to the substrate, in the present case to the neurotoxin polypeptide's light chain of the invention (Marmor and Yarden 2004, Oncogene 23: 2057-2070). Successive conjugations of ubiquitin to the internal lysines of previously added ubiquitin molecules lead to the formation of poly-ubiquitin chains. The poly-ubiquitinated target protein is then recognized by the 26S proteasome and eliminated (Schrader 2009, Nat. Chem. Biol. 5: 815-22). Preferably, the E3 ligase recognition motif as defined herein mediates irreversible degradation. Such irreversible degradation has been described, for instance, for the peptide degradation signal domain "ALAPYIP" (SEQ ID NO: 25). In particular aspects, a E3 ligase-recognition and/or -binding motif is a peptide or peptidomimetic having a length of less than 50 amino acids residues, a length of less than 40 residues, a length of less than 30 residues, a length of less than 20 residues, or a length of less than 15 residues. Examples of specific E3 ligase recognition motifs are indicated in Table 2 or E3 ligase recognition motifs comprising the amino acid sequence ETFSDLWKLLPE (SEQ ID NO: 26), TSFAEYWNLLSP (SEQ ID NO: 27), LTFEHYWAQLTS (SEQ ID NO: 28), LTFEHWWAQLTS (SEQ ID NO: 29), LTFEHSWAQLTS (SEQ ID NO: 30), ETFEHNWAQLTS (SEQ ID NO: 31), LTFEHNWAQLTS (SEQ ID NO: 32), LTFEHWASLTS (SEQ ID NO: 33), LTFEHWWSSLTS (SEQ ID NO: 34), LTFTHWWAQLTS (SEQ ID NO: 35), ETFEHWWAQLTS (SEQ ID NO: 36), LTFEHWWSQLTS (SEQ ID NO: 37), LTFEHWWAQLLS (SEQ ID NO: 38), ETFEHWWSQLLS (SEQ ID NO: 39), RFMDYWEGL (SEQ ID NO: 40), MPRFMDYWEGLN (SEQ ID NO: 41), SQETFSDLWKLLPEN (SEQ ID NO: 42) and/or LTFEHNWAQLEN (SEQ ID NO: 78). Preferably, the E3 ligase recognition motif mediates degradation of at least 10, 20, 30, 40, 50, 60, 70, 80, or 90%, more preferably 100% of the neurotoxin polypeptide's light chain of the invention within the cell. Degradation can be determined by assays described in the art, e.g. by, in vitro assays like quantitative cell based assays, or in vivo assays such as the mouse running assay, digit abduction assay (DAS), or rat grip strength assay.

TABLE 2

In an aspect, the E3 ligase recognition motif comprises or consists of a consensus sequence as shown in the following table (wherein "X" may represent any of the naturally occurring amino acids).

| E3 ubiquitin Ligase | Recognition motif (consensus) |
|---|---|
| VBCCul2 | ALAPYIP (SEQ ID NO: 25) |
| MDM2 | XXFXXXWXXLXX (SEQ ID NO: 43) |
| Smurf2 | ELESPPPPYSRYPM (SEQ ID NO: 44) |
| RN181 | KVGFFKR (SEQ ID NO: 45) |
| E3alpha | LLVRGRTLVV (SEQ ID NO: 46) |
| SCF | DRHDSGLDSM (SEQ ID NO: 47) |
| Siah | PXAXVXP (SEQ ID NO: 48) |
| Itch | PPXYXXM (SEQ ID NO: 49) |
| Nedd4-2 | PPXY (SEQ ID NO: 50) |

Figure 2:
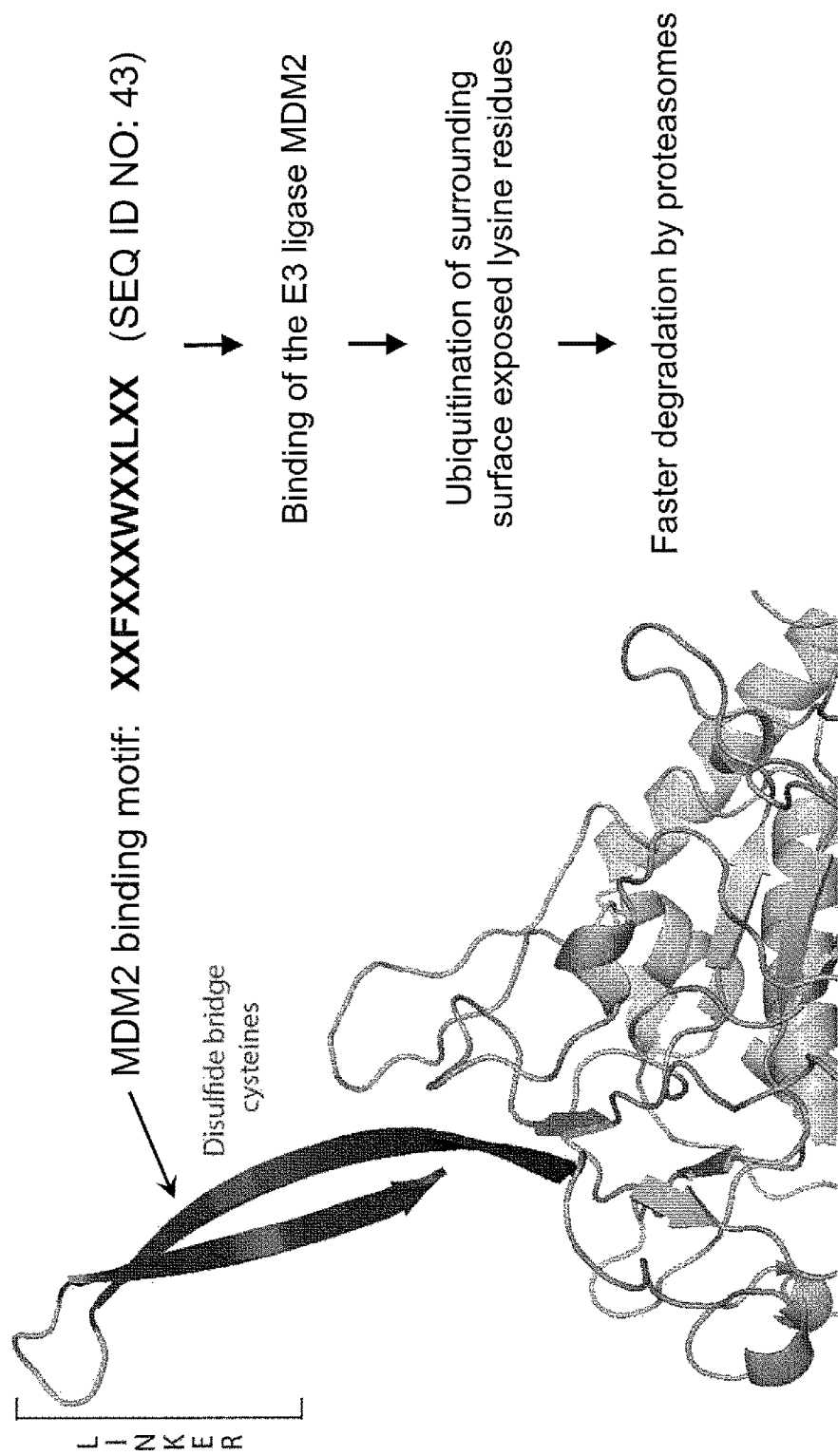

In another aspect, the E3 ligase recognition motif is a binding motif for the E3 ligase MDM2. The corresponding human nucleic acid and amino acid sequences are shown in Accession Nos. NM_002392 and NP_002383, respectively. Preferably, said binding motif for the E3 ligase MDM2 comprises or consists of an amino acid sequence selected from the group consisting of ETFSDLWKLLPE (SEQ ID NO: 26), TSFAEYWNLLSP (SEQ ID NO: 27), LTFEHYWAQLTS (SEQ ID NO: 28), LTFEHWWAQLTS (SEQ ID NO: 29), LTFEHSWAQLTS (SEQ ID NO: 30), ETFEHNWAQLTS (SEQ ID NO: 31), LTFEHNWAQLTS (SEQ ID NO: 32), LTFEHWWASLTS (SEQ ID NO: 33), LTFEHWWSSLTS (SEQ ID NO: 34), LTFTHWWAQLTS (SEQ ID NO: 35), ETFEHWWAQLTS (SEQ ID NO: 36), LTFEHWWSQLTS (SEQ ID NO: 37), LTFEHWWAQLLS (SEQ ID NO: 38), ETFEHWWSQLLS (SEQ ID NO: 39), RFMDYWEGL (SEQ ID NO: 40), MPRFMDYWEGLN (SEQ ID NO: 41), SQETFSDLWKLLPEN (SEQ ID NO: 42) and/or LTFEHNWAQLEN (SEQ ID NO: 78). Even more preferred, said binding motif for the E3 ligase MDM2 comprises or consists of the amino acid sequence LTFEHNWAQLTS (SEQ ID NO: 32) or LTFEHNWAQLEN (SEQ ID NO: 78). It is also preferred that the length of the binding motif for the E3 ligase MDM2 is between 9 and 15 amino acid residues, more preferably it is 12 amino acid residues in length. FIG. 1 illustrates an example of a neurotoxin polypeptide of the invention comprising a binding motif for the E3 ligase MDM2 (MDM2 motif). FIG. 2 shows that the interposition of a binding motif for the E3 ligase MDM2 between the neurotoxin light chain and heavy chain as illustrated in FIG. 1 allows recognition and binding of the E3 ligase MDM2 to the, thus, modified neurotoxin light chain, resulting in ubiquitination of surrounding surface exposed lysine residues and faster degradation of the ubiquitinated neurotoxin light chain of the invention by the cellular proteasome system. It is encompassed within the scope of the present application, that the sequence of the indicated binding motifs for the E3 ligase MDM2 can be further modified, for example, by one or more nucleotide substitutions, deletions and/or additions which in still another aspect may result in an encoded amino acid sequence having one or more amino acid substitutions, deletions and/or additions. Said modifications can be carried out in order to alter (e.g. improve) the binding of the E3 ligase MDM2 to the indicated binding motifs, resulting in a still enhanced degradation of the neurotoxin polypeptide of the invention by the ubiquitin-mediated proteasome degradation pathway.

In a further aspect, said polynucleotide of the invention comprises a nucleic acid sequence selected from the group consisting of:
  a) a nucleic acid sequence having a nucleotide sequence as shown in SEQ ID NO: 51 or 79;
  b) a nucleic acid sequence encoding a polypeptide having an amino acid sequence as shown in SEQ ID NO: 52 or 80; and
  c) a nucleic acid sequence being at least 40%, preferably at least 50%, 60%, 70%, 75%, 80%, 85%, 90%, 95%, 96%, 97%, 98%, 99% or 100% identical to the nucleic acid sequence of a) or b).

As demonstrated in the following Examples, the neurotoxin polypeptide (encoded by the polynucleotide) of the present invention comprising at least one E3 ligase recognition motif in the light chain exhibits a reduced duration of the biological effect in a subject upon administration, in comparison to an unmodified neurotoxin polypeptide (not comprising one or more E3 ligase recognition motif(s) in the light chain). The reduced duration of the biological activity of a, thus, modified polypeptide has been exemplified for BoNT/E-MDM2. The reduced duration of the biological effect of the neurotoxin polypeptide of the invention is a result of the faster degradation of said neurotoxin polypeptide (i.e. of the catalytic neurotoxin light chain) by the proteasome system in the neuron of the subject.

The above-mentioned BoNT/E-MDM2 polypeptide has been further improved by the present inventors by site-directed mutagenesis of exposed amino acid residues in the light chain which are located in spatial proximity to the MDM2-recognition motif. "Exposed amino acid residues" as used herein means that the amino acid residues are located at the surface of the neurotoxin's light chain, e.g. the BoNT/E light chain, and the side chains of said amino acid residues are not involved in intra-molecular interactions. Said exposed amino acid residues within the light chain have been first identified by three-dimensional structural analysis and then substituted by lysine residues. This optimization procedure resulted in an even more accelerated degradation of the mutated BoNT/E-MDM2 polypeptides, in comparison to non-mutated BoNT/E-MDM2 polypeptides comprising the E3 ligase recognition motif. It has unexpectedly been found that substitutions at Q53, N72, N378, N379, R394 and/or T400 by lysine resulted in faster degradation of the BoNT/E-MDM2 by the proteasome system. The indicated position of the respective amino acid residue is based on the numbering in the amino acid sequence shown in SEQ ID NO: 52. In particular, BoNT/E-MDM2 mutants in which (i) Q53, N72, N378, N379, R394 and T400 (SEQ ID NO: 57); (ii) Q53, N378 and N379 (SEQ ID NO: 58); (iii) N72, N378 and N379 (SEQ ID NO: 61); or (iv) N378, N379 and T400 (SEQ ID NO: 75) in the light chain, have been substituted by lysine residues showed a reduced biological effect on cultured cortex neurons. In contrast, numerous other mutations did not show any reduced duration of the biological effect, as demonstrated in FIG. 3. Accordingly, in a further aspect, the polypeptide of the invention comprises or consists of an amino acid sequence selected from the group consisting of:
  a) an amino acid sequence as shown in SEQ ID NO: 57, 58, 61 or 75; and
  b) an amino acid sequence being at least 40%, preferably 50%, 60%, 70%, 75%, 80%, 85%, 90%, 95%, 96%, 97%, 98%, 99% or 100% identical to the amino acid sequence of a).

Preferably, the amino acid sequence of b) carries the same set of mutations as SEQ ID NO: 57 (Q53, N72, N378, N379, R394 and T400), 58 (Q53, N378 and N379), 61 (N72, N378 and N379) or 75 (N378, N379 and T400), in the light chain. In another aspect, the invention pertains to the polynucleotides encoding the amino acid sequences of a) or b) above.

In an aspect, the said biological effect of the neurotoxin polypeptide of the invention observed in the subject causes muscle paralysis, i.e. a (reversible) inactivation of the muscle's capability to contract. In a further aspect, the reduced duration of the biological effect of the neurotoxin polypeptide of the invention in a human subject persist less than 5, 4, 3, 2 weeks or even less than 1 week. In another aspect, the effects can be tested in vivo by the so-called mouse running assay (Keller 2006, Neuroscience 139: 629-637), the digit abduction assay (Aoki 2001, Toxicon 12: 1815-20) or the rat grip strength assay (Torii 2011, Toxicon 57 (1): 93-9). The biological effects can be determined by the person skilled in the art without further ado. A reduced duration of the biological effect, in an aspect, refers to a statistically significant reduced duration. Whether the duration of an effect is statistically significant reduced can be determined by those skilled in the art by applying standard statistical tests, e.g., determination of confidence intervals, p-value determination, Student's t-test, Mann-Whitney test etc. Preferred confidence intervals are at least 90%, at least 95%, at least 96%, at least 97%, at least 98% or at least 99%. The p-values are, preferably, 0.1, 0.05, 0.01, 0.005, or 0.0001. Preferably, the probability envisaged by the present invention allows that the diagnosis will be correct for at least 60%, at least 70%, at least 80%, or at least 90% of the subjects of a given cohort or population. In an aspect, the said reduced duration persists less than 75%, less than 70%, less than 65%, less than 60%, less than 55%, less than 50%, less than 45%, less than 40%, less than 30% or less than 20% of the normal duration, i.e. the duration observed for an unmodified neurotoxin polypeptide (not comprising one or more E3 ligase recognition motif(s) in or attached to the light chain). In an aspect, normal duration persists for approximately 4 months in the case of BoNT/A, 2 months in the case of BoNT/B, approximately 3 to 4 months in the case of BoNT/C or approximately 4 to 6 weeks in the case of BoNT/E (Foran, J. Biol. Chem. 278 (2): 1363-1371, Eleopra 1998, Neurosci. Lett. 13, 256 (3): 135-138, Eleopra 1997, Neurosci. Lett. 14,224 (2): 91-94, Sloop 1997, Neurology 49 (1): 189-194, Washbourne 1998, J. Physiol. Paris 92 (2): 135-139). It is to be understood that the duration of the effect depends on individual influences in a subject such as genetic background, age, life style etc. Therefore, an approximate duration as meant herein refers to a duration as indicated above for the respective neurotoxin polypeptides (e.g., 4 months for BoNT/A or 4 to 6 weeks for BoNT/E) with a standard deviation of 25% or less, 20% or less, 15% or less, 10% or less or 5% or less.

It has advantageously been found in accordance with the present invention that a neurotoxin polypeptide can be modified to exhibit a shortened biological effect in a subject upon administration. This can be achieved by introducing or linking an E3 ligase recognition motif to the light chain of the said neurotoxin polypeptide since it was found that the persistence of the light chain correlates with the duration of the biological effect. The shortened duration of the biological effect elicited by the neurotoxin polypeptides of the invention is beneficial for various medical applications set forth elsewhere herein which require a reduced duration of the biological effect of said neurotoxin. Such a reduced duration is particularly important in case of short term or acute treatments with neurotoxin, for example, in treatment of surgery wounds, in order to facilitate quick and painless wound healing without scar forming, or in paralyzing the eye lid muscles of patients in artificial coma whose eyes might suffer damages by drying out. Further applications of the neurotoxin polypeptide of the invention are listed elsewhere herein.

The present invention contemplates a vector comprising the polynucleotide of the present invention.

The term "vector", preferably, encompasses phage, plasmid, viral or retroviral vectors as well as artificial chromosomes, such as bacterial or yeast artificial chromosomes. Moreover, the term also relates to targeting constructs which allow for random or site-directed integration of the targeting construct into genomic DNA. Such target constructs, preferably, comprise DNA of sufficient length for either homologous or heterologous recombination as described in detail below. The vector encompassing the polynucleotides of the present invention, in an aspect, further comprises selectable markers for propagation and/or selection in a host. The vector may be incorporated into a host cell by various techniques well known in the art. For example, a plasmid vector can be introduced in a precipitate such as a calcium phosphate precipitate or rubidium chloride precipitate, or in a complex with a charged lipid or in carbon-based clusters, such as fullerenes. Alternatively, a plasmid vector may be introduced by heat shock or electroporation techniques. Should the vector be a virus, it may be packaged in vitro using an appropriate packaging cell line prior to application to host cells. Retroviral vectors may be replication competent or replication defective. In the latter case, viral propagation generally will occur only in complementing host/cells. Moreover, in an aspect of the invention, the polynucleotide is operatively linked to expression control sequences allowing expression in prokaryotic or eukaryotic host cells or isolated fractions thereof in the said vector. Expression of the polynucleotide comprises transcription of the polynucleotide into a translatable mRNA. Regulatory elements ensuring expression in host cells are well known in the art. In an aspect, they comprise regulatory sequences ensuring initiation of transcription and/or poly-A signals ensuring termination of transcription and stabilization of the transcript. Additional regulatory elements may include transcriptional as well as translational enhancers. Possible regulatory elements permitting expression in prokaryotic host cells comprise, e.g., the lac-, trp- or tac-promoter in *E. coli*, and examples for regulatory elements permitting expression in eukaryotic host cells are the AOX1- or the GAL1-promoter in yeast or the CMV-, SV40-, RSV-promoter (Rous sarcoma virus), CMV-enhancer, SV40-enhancer or a globin intron in mammalian and other animal cells. Moreover, inducible expression control sequences may be used in an expression vector encompassed by the present invention. Such inducible vectors may comprise tet or lac operator sequences or sequences inducible by heat shock or other environmental factors. Suitable expression control sequences are well known in the art. Beside elements which are responsible for the initiation of transcription such regulatory elements may also comprise transcription termination signals, such as the SV40-poly-A site or the tk-poly-A site, downstream of the polynucleotide. In this context, suitable expression vectors are known in the art such as Okayama-Berg cDNA expression vector pcDV1 (Pharmacia), pBluescript (Stratagene), pCDM8, pRc/CMV, pcDNA1, pcDNA3 (Invitrogen) or pSPORT1 (Invitrogen). Preferably, said vector is an expression vector and a gene transfer or targeting vector. Expression vectors derived from viruses such as retroviruses, vaccinia virus, adeno-associated virus, herpes viruses, or bovine papilloma virus, may be used for delivery of the polynucleotides or vector of the invention into targeted cell population. Methods which are well known to those skilled in the art can be used to construct recombinant viral vectors; see, for example, the techniques described in Sambrook, Molecular Cloning: A Laboratory Manual, Cold Spring Harbor Laboratory (2001) N.Y. and Ausubel, Current Protocols in Molecular Biology, Green Publishing Associates and Wiley Interscience, N.Y. (1994).

Moreover, the present invention pertains to a host cell comprising the polynucleotide or the vector of the present invention.

The term "host cell" as used herein encompasses prokaryotic and eukaryotic host cells. Preferably, the host cell is an isolated prokaryotic or eukaryotic host cell. In an aspect the host cell is a bacterial cell and, in another aspect, a Firmicutes bacterial cell. In one aspect, the said bacterial host cell is an *E. coli* host cell. In another aspect, it is a *Clostridium* host cell. In a further aspect, the said *Clostridium* host cell is a *Clostridium botulinum* host cell, in even a further aspect, a cell of one of the aforementioned seven different serotypes of *Clostridium botulinum*. In yet another aspect, the bacterial host cell is a *Clostridium tetani* host cell. In a further aspect, the host cell is a *Bacillus* host cell and in a particular aspect a *Bacillus megaterium* host cell. A eukaryotic host cell, in an aspect, is a cell of an animal cell line suitable for production of toxic proteins or a fungal host cell such as a yeast host cell.

Also encompassed by the present invention is a polypeptide encoded by the polynucleotide of the invention. In an aspect of the polypeptide of the invention, the polypeptide further comprises at least one amino acid substitution in the light chain of the neurotoxin polypeptide (but not in the MDM2 binding motif as defined herein). Preferably, the substitution of the naturally occurring amino acid in the light chain is by lysine. More preferably, said polypeptide comprises at least one of the amino acid substitutions selected from the group consisting of Q53K, N72K, N378K, N379K, R394K and T400K. The polypeptide can comprise not only one of said amino acid substitutions but also two, three, four, five, six or even more amino acid substitutions. BoNT/E-MDM2 mutants in which (i) Q53, N72, N378, N379, R394 and T400 (SEQ ID NO. 57), (ii) Q53, N378 and N379 (SEQ ID NO. 58), (iii) N72, N378 and N379 (SEQ ID NO. 61) or (iv) N378, N379 and T400 (SEQ ID NO. 75) in the light chain have been substituted by lysine residues are particularly preferred. In other aspects of the polypeptide of the invention, the polypeptide can comprise, in addition to the above-mentioned amino acid sequence substitutions in the light chain, one or more amino acid sequence substitutions in the MDM2 binding motif, for example, in order to improve binding of the E3 ligase MDM2 to the polypeptide of the invention.

The term "polypeptide" as used herein encompasses isolated or essentially purified polypeptides being essentially free of other polypeptides including the complexing proteins (HA70, HA17, HA33, or NTNH (NBP) of *Clostridium botulinum* or polypeptide preparations comprising other proteins in addition. Moreover, the term includes recombinant and chemically modified polypeptides. Such modifications may be artificial modifications or naturally occurring modifications. As referred to above, the polypeptide of the present invention shall have the biological properties of the neurotoxin polypeptides referred to above. Moreover, it shall exhibit shortened duration of the biological effect in a subject upon administration. Further, the polypeptide of the invention can be composed of a *Botulinum* toxin with a new binding domain to target other types of cells. The polypeptide of the invention, in an aspect, can be manufactured by a method of manufacturing a polypeptide as described elsewhere herein in more detail. In an aspect of the invention, a polypeptide preparation is also envisaged which comprises a complex of the neurotoxin polypeptide and its complexing proteins.

Moreover, the present invention relates to an antibody which specifically binds to the polypeptide of the present invention. In a further aspect, the antibody specifically binds to the amino acid sequence shown in SEQ ID NO: 52, 57, 58, 61 or 75.

Antibodies against the polypeptide of the invention can be prepared by well known methods using a purified polypeptide according to the invention or a suitable fragment derived therefrom as an antigen. A fragment which is suitable as an antigen may be identified by antigenicity determining algorithms well known in the art. Such fragments may be obtained either from the polypeptide of the invention by proteolytic digestion or may be a synthetic peptide. In an aspect, the antibody of the present invention is a monoclonal antibody, a polyclonal antibody, a single chain antibody, a human or humanized antibody or primatized antibody, chimerized antibody or a fragment thereof. Also comprised as antibodies by the present invention is a bispecific or bispecific single chain antibody, a synthetic antibody, an antibody fragment, such as a Fab, Fv or scFv fragment etc., or a chemically modified derivative of any of these. The antibody of the present invention shall specifically bind (i.e. does not cross react with other polypeptides or peptides) to the polypeptide of the invention. Specifically, the antibody shall also not cross react with the unmodified neurotoxin polypeptide (not carrying a MDM2 binding motif). Further, the antibody shall not cross react with the E3 ligase MDM2. Specific binding can be tested by various well known techniques. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described by Köhler et al. (Köhler 1975, Nature 256: 495) or Galfré (Galfré 1981, Meth. Enzymol. 73) which comprise the fusion of mouse myeloma cells to spleen cells derived from mammals which have been immunized by the antigen, i.e. the polypeptide of the invention or a immunogenic fragment thereof. The antibodies can be used, for example, for the immunoprecipitation and immunolocalization of the polypeptides of the invention as well as for the monitoring of the presence of said polypeptides, for example, in recombinant organisms, and for the identification of compounds interacting with the proteins according to the invention. For example, surface plasmon resonance as employed in the BIAcore system can be used to increase the efficiency of phage antibodies which bind to an epitope of the protein of the invention (Schier 1996, Human Antibodies Hybridomas 7: 97-105; Malmborg 1995, J. Immunol. Methods 183: 7-13). In another aspect, the antibody of the invention specifically binds to one or more of the amino acid substitutions selected from the group consisting of Q53K, N72K, N378K, N379K, R394K and T400K, with the position numbering corresponding to that of SEQ ID NO: 52.

The polynucleotide or polypeptide of the invention can be used as a medicament, in general.

The term "medicament" as used herein refers, in one aspect, to a pharmaceutical composition containing the biologically active neurotoxin polypeptide of the invention or a polynucleotide encoding it as pharmaceutical active compound. The said medicament may be used for human or animal therapy of various diseases or disorders in a therapeutically effective dose. The medicament can be formulated by various techniques dependent on the desired application purposes. Different aspects of a medicament according to the present invention are specified herein below.

In an aspect, the medicament comprises the biologically active neurotoxin polypeptide of the present invention one or more pharmaceutically acceptable carrier as a pharmaceutical composition. The pharmaceutically acceptable carrier(s) must be acceptable in the sense of being compatible with the other ingredients of the formulation and being not deleterious to the recipient thereof. The pharmaceutical carrier employed may include a solid, a gel, or a liquid. Exemplary of solid carriers are lactose, terra alba, sucrose, talc, gelatine, agar, pectin, acacia, magnesium stearate, stearic acid and the like. Exemplary of liquid carriers are glycerol, phosphate buffered saline solution, water, emulsions, various types of wetting agents, and the like. Suitable carriers comprise those mentioned above and others well known in the art, see, e.g., Remington's Pharmaceutical Sciences, Mack Publishing Company, Easton, Pa. It will be understood that a carrier might also be a virus or retrovirus suitable for gene therapy, in particular, if the active ingredient of the medicament is the polynucleotide of the invention.

The medicament, in an aspect, will be dissolved in a diluent prior to administration. The diluent is also selected so as not to affect the biological activity of the combination. Examples of such diluents are distilled water or physiological saline. In addition, the pharmaceutical composition or formulation may also include other carriers or non-toxic, non-therapeutic, non-immunogenic stabilizers and the like. Thus, the neurotoxin polypeptide of the invention can be present, in an aspect, in liquid or lyophilized form. In an aspect, it can be present together with glycerol, protein stabilizers (HSA) or non-protein stabilizers such as polyvinyl pyrrolidone (PVP), hyaluronic acid or free amino acids. In an aspect, suitable non-proteinaceous stabilizers are disclosed in WO 2005/007185 or WO 2006/020208.

In another aspect, the medicament will be provided as a solution comprising the neurotoxin polypeptide. Moreover, the solution can comprise carriers or stabilizers referred to above as well. A stable liquid formulation of the neurotoxin polypeptide can be provided, in an aspect, as disclosed by U.S. Pat. No. 7,211,261.

The pharmaceutical composition is, in one aspect, administered topically. Conventionally the medicament will be administered intra-muscular or subcutaneous (near glands) depending on the desired medical indication. However, depending on the nature and the mode of action of a compound the pharmaceutical composition may be administered by other routes as well.

A therapeutically effective dose refers to an amount of the neurotoxin polypeptide or the polynucleotide of the invention which prevents, ameliorates or treats the symptoms accompanying a condition or disease referred to in this specification. Therapeutic efficacy and toxicity of the compound can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. The medicament of the present invention will comprise, in an aspect, dosage recommendations in the prescribers or users instructions in order to anticipate dosage adjustments depending on the individual recipient.

The medicament referred to herein are developed to be administered at least once in order to treat or ameliorate or prevent a disease or condition recited in this specification. However, the said medicament may be administered more than one time.

The medicament according to the present invention may in a further aspect of the invention comprise drugs in addition to the biologically active neurotoxin polypeptide which are added to the pharmaceutical composition during its formulation.

Moreover, the present invention pertains to the use of the polynucleotide or the polypeptide of the present invention for the preparation of a medicament for the treatment of wound healing, immobilization for bone and tendon fracture treatment, post surgery immobilization, specifically in connection with haemorrhoidectomy, introduction of dental implants, hip joint replacement (endoprothesis), epicondylitis, knee arthroplasty, ophthalmological surgery, acne, irritable bowel disease, vaginism, low back pain, or benign prostate dysplasia.

The symptoms associated with the aforementioned medical conditions or diseases are well known to the person skilled in the art and are described in standard text books of medicine such as Stedman or Pschyrembel.

Moreover, the present invention also relates to the use of the polynucleotide or the polypeptide of the present invention for the preparation of a diagnostic medicament for determining whether a subject is susceptible for a neurotoxin therapy.

The diagnostic medicament referred to above is a neurotoxin polypeptide medicament as referred to above. However, the medicament is to be applied for a time and at a dosage regimen allowing merely the determination of whether a subject responds to the neurotoxin polypeptide at all or the determination of a suitable dosage regimen. Since the above neurotoxin polypeptide—although having therapeutic potential as well—is pivotally used for a diagnostic purpose rather than for treating or amelioration in this aspect, the medicament comprising it is termed "diagnostic medicament". Thus, such a time-restricted pre-screen with the modified neurotoxin polypeptides of the present invention will assist in selecting subjects susceptible for a therapy using an unmodified neurotoxin as well as in determining a suitable dosage. Potential side effects of a therapy based on an unmodified neurotoxin which would normally persist over a longer time can be reduced due to the reduced duration of the biological effect elicited by the modified neurotoxin polypeptide of the invention.

The present invention encompasses a method for the manufacture of a neurotoxin polypeptide encoded by the polynucleotide of the invention comprising the steps of:
a) cultivating the host cell of the invention under conditions which allow for the expression of the neurotoxin polypeptide encoded by the polynucleotide of the invention, and
b) obtaining the neurotoxin polypeptide encoded by the polynucleotide of the invention from the host cell culture of a).

The polypeptide may be obtained from the culture, in an aspect, by all conventional purification techniques including affinity chromatography, ion exchange chromatography, size exclusion chromatography, high pressure liquid chromatography (HPLC) and precipitation techniques including antibody precipitation. In another aspect, the neurotoxin polypeptide may be obtained as a complex comprising in addition to the neurotoxin polypeptide complexing proteins. Moreover, obtaining as used herein, in an aspect, includes activation of the neurotoxin polypeptide. This can be achieved by proteolytic cleavage of the (single-chain) neurotoxin polypeptide precursor either intracellular by an endogenous or exogenous (e.g., recombinant expressed) protease or outside the cell by contacting the neurotoxin polypeptide, e.g., prior, during or after the aforementioned purification, with the protease under conditions allowing for cleavage.

Furthermore, a method for the manufacture of a medicament is contemplated in accordance with the present invention, said method comprising the steps of the aforementioned method of the invention and the further step of formulating the neurotoxin polypeptide encoded by the polynucleotide of the invention as a medicament.

It will be understood that such a method for the manufacture of a medicament is carried out according to the GMP standards for medicaments in order to ensure quality, pharmaceutical safety, and efficacy of the medicament. Suitable formulations of the medicament are described elsewhere in this specification. The person skilled in the art is, however, well aware of how such formulations can be made.

The invention also encompasses a method for the manufacture of a cosmetic composition comprising the steps of the method of the invention and the further step of formulating the neurotoxin polypeptide as a cosmetic composition.

"Cosmetic composition" as used herein can be formulated and used as described for a pharmaceutical composition above. For a cosmetic composition, likewise, it is envisaged that the compound of the present invention is in an aspect used in substantially pure form. Impurities, however, may be less critical than for a medicament. Cosmetic compositions are, in a further aspect, to be applied intramuscular. In an even further aspect of the invention, cosmetic compositions comprising the neurotoxin can be formulated as an anti-wrinkle agent.

The present invention also pertains to such a cosmetic composition and to the use of the polynucleotide or the polypeptide of the present invention for the preparation of a cosmetic composition to be used as an anti-wrinkle agent.

All references cited in this specification are herewith incorporated by reference with respect to their entire disclosure content and the disclosure content specifically mentioned in this specification.

FIGURES

FIG. 1: Modified *Botulinum* neurotoxin harboring an MDM2 binding motif. Illustration of a modified *botulinum* neurotoxin with a binding motif for the E3 ligase MDM2 interposed between the *botulinum* neurotoxin light chain and heavy chain, comprising, from the N- to the C-terminus, a *botulinum* neurotoxin light chain, a MDM2 binding motif, a linker comprising a protease cleavage site and the *botulinum* neurotoxin heavy chain. The *botulinum* neurotoxin light chain and heavy chain are interlinked by a disulfide bridge.

FIG. 2: Introduction of MDM2 binding motifs. Interposition of a binding motif for the E3 ligase MDM2 between the *botulinum* neurotoxin light chain and heavy chain as illustrated in FIG. 1 allows recognition and binding of the E3 ligase MDM2 to the, thus, modified *botulinum* neurotoxin, resulting in ubiquitination of the indicated surrounding surface exposed lysine residues and faster degradation of the ubiquitinated *botulinum* neurotoxin by the cellular proteasome system. Illustrated is the MDM2 binding consensus motif XXFXXXWXXLXX (SEQ ID NO: 43, with "X" representing any of the naturally occurring amino acids).

FIG. 3: Generation and analysis of the duration of the biological activity of

BoNT/E-MDM2 mutants. The effect on the duration of the biological activity of BoNT/E-MDM2 mutants in frontal cortex cells of the mouse is shown, in comparison to non-mutated BoNT/E-MDM2 (SEQ ID NO. 52). Indicated are the corresponding amino acid residues which have been substituted by lysine, respectively. As a result, BoNT/E-MDM2 mutants in which (i) Q53, N72, N378, N379, R394 and T400 (SEQ ID NO. 57), (ii) Q53, N378 and N379 (SEQ ID NO. 58), (iii) N72, N378 and N379 (SEQ ID NO. 61) or (iv) N378, N379 and T400 (SEQ ID NO. 75) in the light chain have been substituted by lysine residues showed a reduced duration of the biological effect on cortex neurons. Consequently, the introduction of lysine residues in the BoNT/E-MDM2 neurotoxin at the indicated positions resulted in a quicker degradation of the mutant light chain in cortex neurons. In contrast, numerous other tested amino acid substitutions and combinations thereof in the light chain did not show an effect on the duration of the neurotoxin's biological activity. The abbreviation "n.d." means not (yet) determined.

Figure 4:
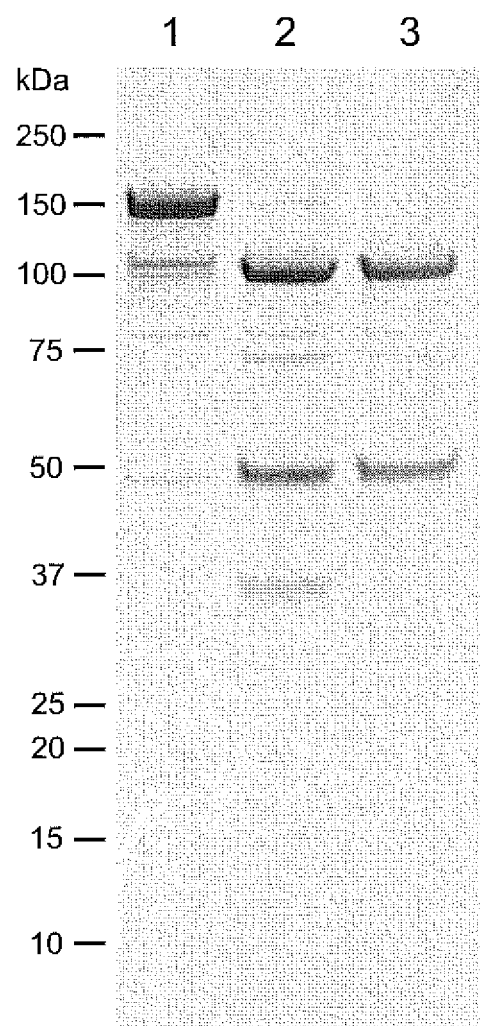

FIG. 4: Activation of purified BoNT/E-MDM2 (SEQ ID NO: 52) by protease cleavage. Purified single-chain BoNT/E was cleaved with Thrombin according to Example 2, the protease was removed and the activated BoNT/E was analyzed by SDS-PAGE and Commassie staining. Lane 1: purified single-chain BoNT/E-MDM2; Lane 2: activated BoNT/E-MDM2; Lane 3: activated BoNT/E-MDM2, Thrombin removed.

Figure 5:
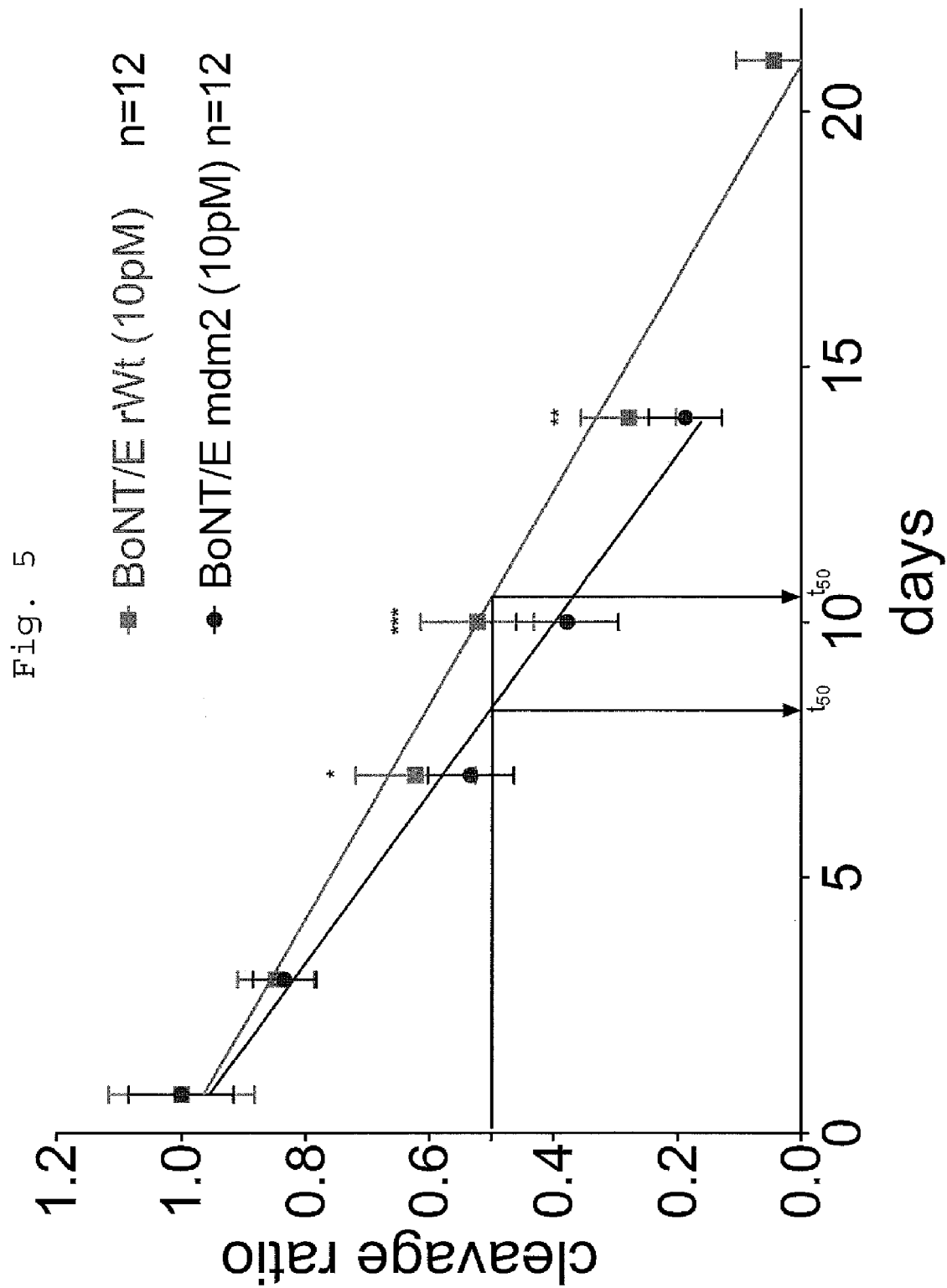

FIG. 5: Comparison of BoNT/E-MDM2 (SEQ ID NO: 52) with the Recombinant Wild Type BoNT/E (rWT) (SEQ ID NO: 82) in frontal cortex neurons. Frontal cortex neurons were incubated with equipotent doses of rWT (SEQ ID NO: 82) and BoNT/E-MDM2 (SEQ ID NO: 52). At defined time points, the ratio of cleaved to total SNAP-25 was analyzed which is a measure of the presence of the light chain in the nerve cell.

Figure 6:
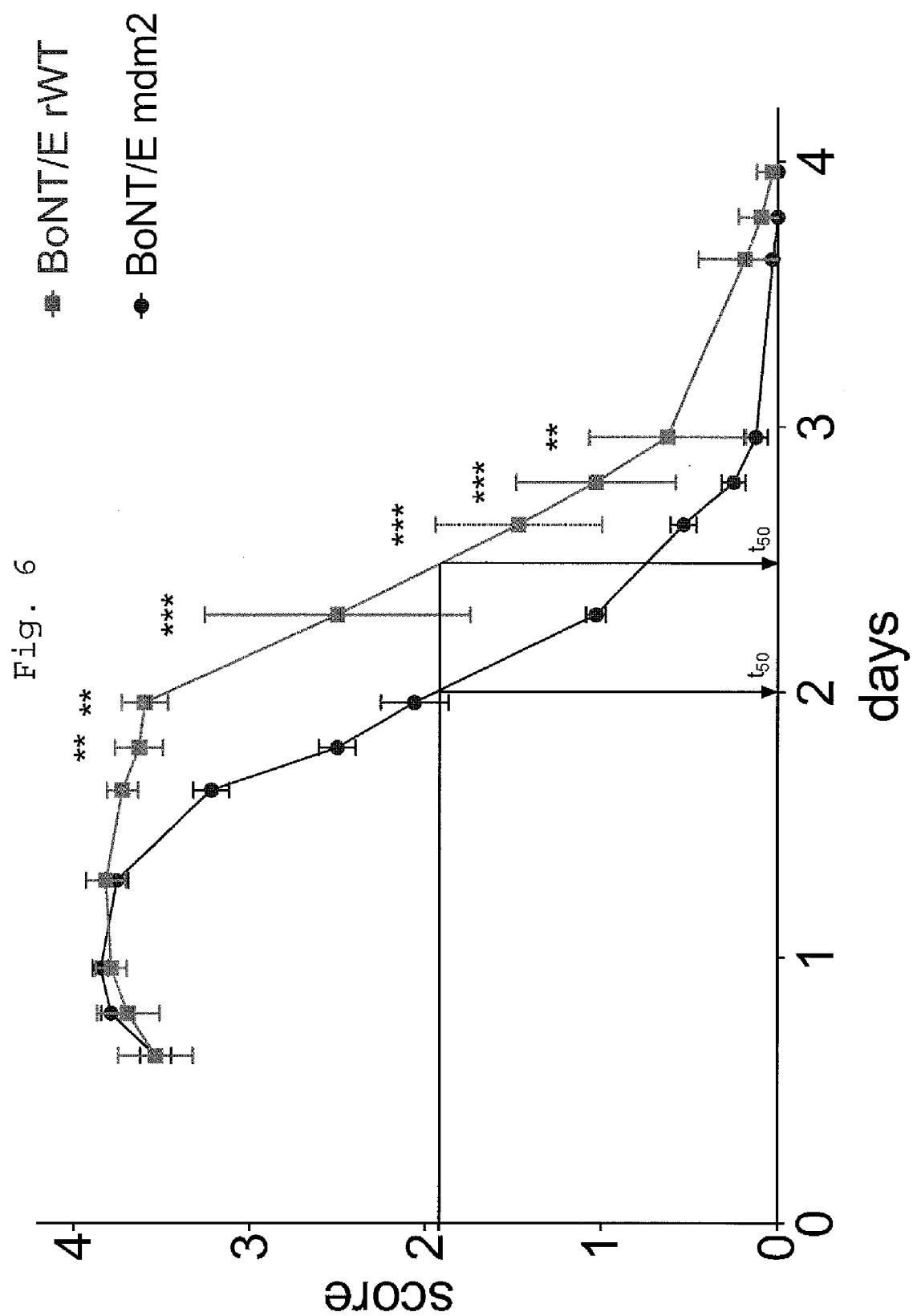

FIG. 6: Comparison of BoNT/E-MDM2 (SEQ ID NO: 52) with the Recombinant Wild Type BoNT/E (SEQ ID NO: 82) in the Digit Abduction Score (DAS) Assay. Equipotent doses of rWT (SEQ ID NO: 82) and BoNT/E-MDM2 (SEQ ID NO: 52) were injected into the gastrocnemius muscle of mice and the paralysis was analyzed in the DAS assay.

Figure 7:
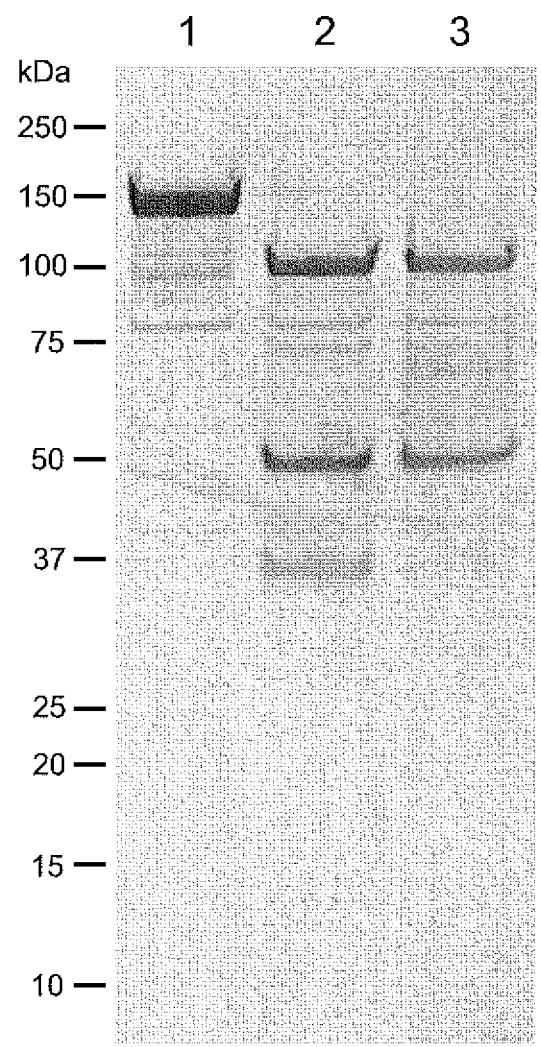

FIG. 7: Activation of purified BoNT/E-MDM2 (SEQ ID NO: 80) by protease cleavage. Purified single-chain BoNT/E was digested with Thrombin according to Example 6, the protease was removed and the activated BoNT/E was analyzed by SDS-PAGE and Coomassie staining. Lane 1: purified single-chain BoNT/E-MDM2; Lane 2: activated BoNT/E-MDM2; Lane 3: activated BoNT/E-MDM2, Thrombin removed.

Figure 8:
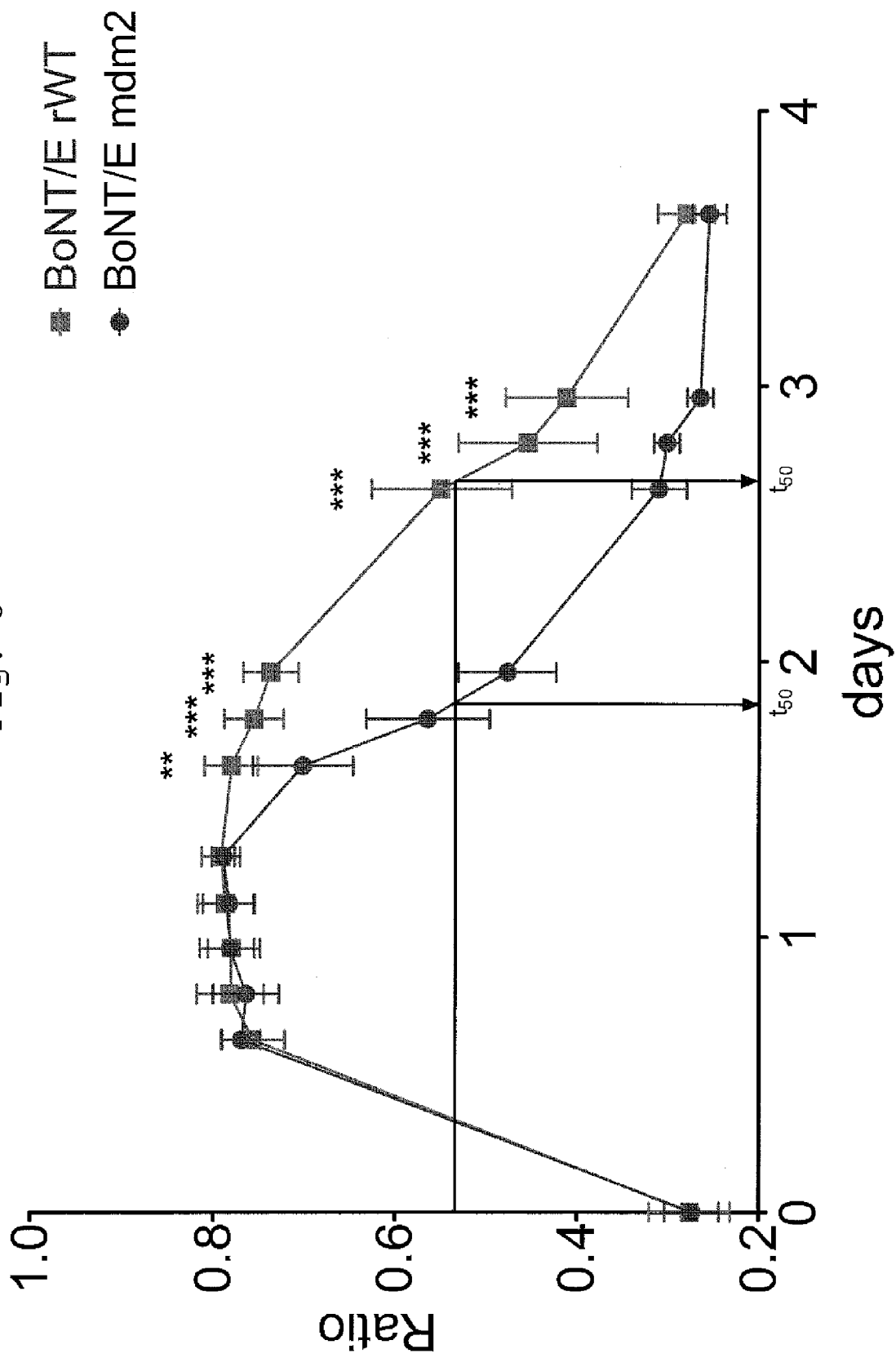

FIG. 8: Comparison of BoNT/E-MDM2 (SEQ ID NO: 80) with the Recombinant Wild Type BoNT/E (SEQ ID NO: 82) in the Foto Digit Abduction Score (DAS) Assay. Equipotent doses of rWT (SEQ ID NO: 82) and BoNT/E-MDM2 (SEQ ID NO: 80) were injected into the gastrocnemius muscle of mice and the paralysis was analyzed in the Foto-DAS assay. In contrast to the DAS Assay (see FIG. 5), the effect in this assay was shown as the difference 1−ratio of width to length of the injected paw.

EXAMPLES

The invention will now be illustrated by the following Examples which shall, however, not be construed as limiting the scope of the invention.

Example 1

Construction, Expression and Purification of Recombinant BoNT/E Comprising a MDM2 Recognition Motif (BoNT/E-MDM2; SEQ ID NO: 52)

The coding sequence of *Botulinum* neurotoxin type E (BoNT/E) harboring the MDM2 binding motif "LTFEHN-WAQLTS" as shown in SEQ ID NO: 32 was gene synthesized and subcloned into an *E. coli* expression vector adding C-terminal purification tags (e.g. His-tag). The protein (with the amino acid sequence shown in SEQ ID NO: 52, BoNT/E-MDM2) was expressed in *E. coli* BL21 using LB medium for 24 h at 16° C. The expressed neurotoxin was purified using a 3-step chromatography protocol (e.g. affinity chromatography employing C-terminal affinity tags such as His-tag, ion exchange chromatography and/or size exclusion chromatography). The tags were afterwards removed by protease cleavage employing a C-terminal protease cleavage

19 site (e.g. Thrombin cleavage site) and the purity of the protein was analyzed by SDS-PAGE.

Example 2

Activation of Purified BoNT/E by Protease Cleavage

Purified *Botulinum* neurotoxin (see Example 1) with the amino acid sequence as shown in SEQ ID NO: 52 harbouring a Thrombin cleavage site in the linker between light and heavy chain was incubated with biotinylated Thrombin at 20° C. O/N. Biotinylated Thrombin was removed by affinity chromatography (e.g. incubation with streptavidin agarose) and the activated toxin was analyzed by SDS-PAGE followed by Coomassie staining (see FIG. 4) and immunoblotting. The final concentration of the activated neurotoxin was determined by ELISA using a rabbit anti-BoNT/E antibody for capture and a guinea pig anti-BoNT/E antibody for detection. Potency testing was carried out using the hemidiaphragm assay (HDA).

Example 3

Determination of the Persistence In Vitro

Frontal cortex tissue was harvested from embryonic day 15-16 mice. Cells were suspended in Neurobasal™ medium at a density of $0.5 \times 10^6$ cells per mL and 2000 µL were seeded onto 6-well plates. Cultures were incubated at 37° C. in a 4% $CO_2$ atmosphere for 3.5 weeks. The cultures were treated with 5-fluaro-2'desoxyuridine (25 µM) and uridine (64 µM) to prevent further glial proliferation. The cultures were then treated with either 10 pM of wildtype BoNT/E (SEQ ID NO: 82) or BoNT/E comprising a MDM2 recognition motif (SEQ ID NO: 52; Example 2) for precisely 18 h and washed afterwards with conditioned cell culture medium. At this time point and after 3 days, 7 days, 10 days, 14 days and 21 days, cells were harvested and the ratio of cleaved to total SNAP25 in the Western Blot was determined applying a mouse monoclonal antibody (Synaptic Systems #111111). It was found that the cleavage ratio in the cell cultures treated with the BoNT/E comprising the MDM2 recognition motif (SEQ ID NO. 52) reached the 50% ratio ($t_{50}$) in a time about 25% shorter compared to the wild type BoNT/E (SEQ ID NO: 82); see FIG. 5. This shows that the persistence of the light chain in the neuronal cells was reduced by 25% which demonstrates that the duration of the biological effect was reduced by 25%.

Example 4

Determination of the Recovery In Vivo

BoNT/E-MDM2 as described in Example 2 (SEQ ID NO: 52) was analyzed in the digit abduction assay (DAS) (Aoki, 2001 Toxicon. (12):1815-20). An equipotent dose of wild type and the mutant BoNT/E comprising the MDM2 motif were injected into the gastrocnemius muscle of 10 mice. The mice were scored according to the scale described in Aoki 2001 Toxicon. (12):1815-20. The recovery time of the mice treated with the BoNT/E-MDM2 (Example 2, SEQ ID NO. 52) was reduced by about 20%, compared to wild type BoNT/E (SEQ ID NO: 82); see FIG. 6.

20

Example 5

Construction, Expression and Purification of Recombinant BoNT/E Comprising a MDM2 Recognition Motif (BoNT/E-MDM2; SEQ ID NO: 80)

The coding sequence of *Botulinum* Neurotoxin type E (BoNT/E) harboring the MDM2 binding motif "LTFEHNWAQLEN" as shown in SEQ ID NO: 78 was gene synthesized and subcloned into an *E. coli* expression vector adding C-terminal purification tags (e.g. His-tag). The protein (with the amino acid sequence shown in SEQ ID NO: 80, BoNT/E-MDM2) was expressed in *E. coli* BL21 using LB medium for 24 h at 16° C. The expressed neurotoxin was purified using a 3-step chromatography protocol (e.g. affinity chromatography employing C-terminal affinity tags such as His-tag, ion exchange chromatography and/or size exclusion chromatography). The tags were afterwards removed by protease cleavage employing a C-terminal protease cleavage site (e.g. Thrombin cleavage site) and the purity of the protein was analyzed by SDS-PAGE.

Example 6

Activation of Purified BoNT/E by Protease Cleavage

Purified *Botulinum* Neurotoxin (Example 5) with the amino acid sequence as shown in SEQ ID NO: 80 harbouring a Thrombin cleavage site in the linker between light and heavy chain was incubated with biotinylated Thrombin at 20° C. O/N. Biotinylated Thrombin was removed by affinity chromatography (e.g. incubation with streptavidin agarose) and the activated toxin was analyzed by SDS-PAGE followed by Coomassie staining (see FIG. 7) and immunoblotting. The final concentration of the activated neurotoxin was determined by ELISA using a rabbit anti-BoNT/E antibody for capture and a guinea pig anti-BoNT/E antibody for detection. Potency testing was carried out using the hemidiaphragm assay (HDA).

Example 7

Determination of the Persistence In Vitro

Frontal cortex tissue was harvested from embryonic day 15-16 mice. Cells were suspended in Neurobasal™ medium at a density of $0.5 \times 10^6$ cells per mL and 2000 µL were seeded onto 6-well plates. Cultures were incubated at 37° C. in a 4% $CO_2$ atmosphere for 3.5 weeks. The cultures were treated with 5-fluaro-2'desoxyuridine (25 µM) and uridine (63 µM) to prevent further glial proliferation. The cultures were then treated with either 10 pM of wildtype BoNT/E (SEQ ID NO: 82) or BoNT/E comprising a MDM2 recognition motif (SEQ ID NO: 80; Example 6) for precisely 18 h and washed afterwards with conditioned cell culture medium. At this time point and after 3 days, 7 days, 10 days, 14 days and 21 days cells were harvested and the ratio of cleaved to total SNAP-25 in the Western Blot was determined applying a mouse monoclonal antibody (Synaptic Systems #111111). It was found that the cleavage ratio in the cell cultures treated with the BoNT/E comprising the MDM2 recognition motif (SEQ ID NO. 80) reached the 50% ratio ($t_{50}$) in a time about 25% shorter compared with the wild type BoNT/E (SEQ ID NO: 82). This shows that the persistence of the light chain in the neuronal cells was

Example 8

Determination of the Recovery In Vivo

In a slightly modified setup of the DAS assay (see [0071]), the scoring was replaced by calculating the difference between 1-ratio of width to length of the injected paw. The recovery time of the mice treated with the BoNT/E-MDM2 (Example 6, SEQ ID NO. 80) was reduced by about 25% compared to wild type BoNT/E (SEQ ID NO: 82); see FIG. 8.

Example 9

Generation of BoNT/E-MDM2 Mutants

The generation of two different BoNT/E-MDM2 polypeptides (SEQ ID NO. 52 and SEQ ID NO: 80) has been described in Examples 1 and 5. Subsequently, exposed amino acid residues in the BoNT/E light chain located in the spatial proximity of the MDM2-recognition motif have been identified by the analysis of the three-dimensional structure of the BoNT/E light chain. "Exposed amino acid residues" as used herein means that the amino acid residues are located at the surface of the BoNT/E light chain and the side chains of said amino acid residues are not involved in intra-molecular interactions. The exposed amino acid residues have been identified by molecular dynamic (MD) simulations and calculation of the solvent accessible surface area (SASA). A SASA value higher than 60% (mostly) has been chosen as a specific cutoff. The exchange of the exposed amino acid residues at the identified positions by lysine residues as shown in FIG. 3 has been carried out by site-directed mutagenesis using a QuikChangeTM mutagenesis kit, in combination with specific primer pairs which have been designed to this end. The substitution by lysine residues of the identified exposed amino acid residues not involved in intra-molecular interactions has been performed because E3 ligases, including MDM2, ubiquitinylate their substrates at lysine residues. To this end, the E3 ligase first binds to the E3 ligase binding motif in the substrate, e.g. the MDM2 binding motif in a BoNT/E-MDM2 protein as described herein, and then "detects" lysine residues in the spatial proximity to the binding motif in the substrate which can be modified by ubiquitin molecules. Accordingly, the efficacy of proteasomal degradation is increased by the introduction of additional lysine residues in the light chain of the Neurotoxin polypeptide of the invention, comprising a MDM2 E3 ligase binding motif. The resulting DNA constructs have been transformed into an *E. coli* expression strain (BL21) and the thus modified recombinant *Botulinum* Neurotoxins have been expressed. The mutated recombinant *Botulinum* Neurotoxins have been purified from cell lysates of *E. coli* via affinity chromatography (e.g. His-tag), ion exchange chromatography and/or size exclusion chromatography. Said mutated Neurotoxins have been activated by proteolytic cleavage using the protease Thrombin and subsequent removal of the protease. In the following, the thus purified and activated mutated Neurotoxins have been analyzed, as shown in the subsequent Example.

Example 10

Analysis of the Degradation of BoNT/E-MDM2 Mutants in a Cell Culture System To this end, a cell culture of frontal cortex cells of the mouse has been established, as indicated in Example 3. One x $10^6$ cells have been treated with 20 pM BoNT/E-MDM2 (SEQ ID NO. 52) and with the respective BoNT/E-MDM2 mutants (see FIG. 3) for 18 hours in six well plates. After 18 hours, 3 days, 7 days, 10 days, 14 days, and 21 days, samples have been isolated and analyzed by Western Blot using an antibody which recognizes both SNAP-25 as well as SNAP-25 cleaved by BoNT/E (Synaptic Systems #111111). The ratio of cleaved to uncleaved SNAP-25 has been taken as measurement for the biological activity of the light chain of the *Botulinum* Neurotoxin in the frontal cortex cells that is for its concentration. As a result, it has been found that the proteolytic activity and hence the concentration of the light chain of the BoNT/E-MDM2 mutants has been reduced significantly quicker, in comparison to that of BoNT/E-MDM2; see FIG. 3. In particular, BoNT/E-MDM2 mutants in which (i) Q53, N72, N378, N379, R394 and T400 (SEQ ID NO. 57), (ii) Q53, N378 and N379 (SEQ ID NO. 58), (iii) N72, N378 and N379 (SEQ ID NO. 61) or (iv) N378, N379 and T400 (SEQ ID NO. 75) in the light chain have been substituted by lysine residues showed a reduced biological effect on cortex neurons. Consequently, the introduction of lysine residues in the BoNT/E-MDM2 Neurotoxins resulted in a quicker degradation of the mutant light chain in cortex neurons. In contrast, numerous other tested amino acid substitutions and combinations thereof in the light chain did not show an effect on the duration of the Neurotoxin's biological activity.

---

The invention claimed is:

1. A polynucleotide encoding a neurotoxin polypeptide exhibiting a reduced duration of muscle paralysis in a subject, wherein the neurotoxin polypeptide comprises at least one E3 ligase recognition motif in a light chain region of the neurotoxin polypeptide, wherein the E3 ligase recognition motif is a binding motif for the E3 ligase MDM2.

2. The polynucleotide of claim 1, wherein the binding motif for the E3 ligase MDM2 is selected from the group consisting of ETFSDLWKLLPE (SEQ ID NO: 26), TSFAEYWNLLSP (SEQ ID NO: 27), LTFEHYWAQLTS (SEQ ID NO: 28), LTFEHWWAQLTS (SEQ ID NO: 29), LTFEHSWAQLTS (SEQ ID NO: 30), ETFEHNWAQLTS (SEQ ID NO: 31), LTFEHNWAQLTS (SEQ ID NO: 32), LTFEHWWASLTS (SEQ ID NO: 33), LTFEHVVVVSSLTS (SEQ ID NO: 34), LTFTHWWAQLTS (SEQ ID NO: 35), ETFEHWWAQLTS (SEQ ID NO: 36), LTFEHWWSQLTS (SEQ ID NO: 37), LTFEHWWAQLLS (SEQ ID NO: 38), ETFEHVVWSQLLS (SEQ ID NO: 39), MPRFMDYWEGLN (SEQ ID NO: 41), SQETFSDLWKLLPEN (SEQ ID NO: 42) and LTFEHNWAQLEN (SEQ ID NO: 78).

3. The polynucleotide of claim 1, wherein the reduced duration of biological effect persists less than 5, 4, 3, 2 weeks or less than 1 week.

4. The polynucleotide of claim 1, wherein the light chain of the polypeptide is obtained by modification from a light chain being encoded by a polynucleotide comprising a nucleic acid sequence selected from the group consisting of:
   a) a nucleic acid sequence having a nucleotide sequence of SEQ ID NO: 1, 3, 5, 7, 9, 81, 11, 13 or 15;
   b) a nucleic acid sequence encoding a polypeptide having an amino acid sequence of SEQ ID NO: 2, 4, 6, 8, 10, 82, 12, 14, or 16; and
   c) a nucleic acid sequence being at least 40% identical to the nucleic acid sequence of a) or b).

5. The polynucleotide of claim 1, wherein the polynucleotide comprises a nucleic acid sequence selected from the group consisting of:
   a) a nucleic acid sequence having a nucleotide sequence of SEQ ID NO: 51 or 79;
   b) a nucleic acid sequence encoding a polypeptide having an amino acid sequence of SEQ ID NO: 52 or 80; and
   c) a nucleic acid sequence being at least 40% identical to the nucleic acid sequence of a) or b).

6. A vector comprising the polynucleotide of claim 1.

7. An in vitro protein expression system host cell comprising the polynucleotide of claim 1.

8. An in vitro protein expression system host cell comprising the vector of claim 6.

9. The in vitro protein expression system host cell of claim 8, wherein the cell is an *E. coil* cell, a *Clostridium* cell or a *Bacillus* cell.

10. A polypeptide encoded by the polynucleotide of claim 1.

11. The polypeptide of claim 10, further comprising at least one amino acid substitution by lysine in the light chain of the neurotoxin polypeptide.

12. The polypeptide of claim 11, comprising at least one amino acid substitution selected from the group consisting of Q53K, N72K, N378K, N379K, R394K and T400K.

13. An antibody which specifically binds to the polypeptide of claim 10, wherein the antibody does not cross react with (i) unmodified neurotoxin polypeptides not carrying a binding motif for the E3 ligase MDM2 and (ii) the E3 ligase MDM2.

14. A method of treatment providing for wound healing, immobilization for bone and tendon fracture treatment, post surgery immobilization, specifically in connection with haemorrhoidectomy, introduction of dental implants, or hip joint replacement, endoprothesis, epicondylitis, knee arthroplasty, ophthalmological surgery, acne, irritable bowel disease, vaginism, low back pain, or benign prostate hyperplasia, comprising administering to a subject in the need thereof a therapeutically effective amount of a polynucleotide of claim 1.

15. A method of treatment providing for wound healing, immobilization for bone and tendon fracture treatment, post surgery immobilization, specifically in connection with haemorrhoidectomy, introduction of dental implants, or hip joint replacement, endoprothesis, epicondylitis, knee arthroplasty, ophthalmological surgery, acne, irritable bowel disease, vaginism, low back pain, or benign prostate hyperplasia, comprising administering to a subject in the need thereof a therapeutically effective amount of a polypeptide of claim 10.

16. A method for the manufacture of a neurotoxin polypeptide composition comprising the steps of:
 a) cultivating a host cell under conditions which allow for expression of the neurotoxin polypeptide encoded by the polynucleotide of claim 1, and
 b) obtaining the neurotoxin polypeptide from the host cell.

17. The method of claim 16, further comprising a step of formulating the neurotoxin polypeptide with a pharmaceutically acceptable carrier.

\* \* \* \* \*

SEQUENCE LISTING

```
<160> NUMBER OF SEQ ID NOS: 82

<210> SEQ ID NO 1
<211> LENGTH: 3891
<212> TYPE: DNA
<213> ORGANISM: Clostridium botulinum

<400> SEQUENCE: 1
atgccatttg ttaataaaca atttaattat aaagatcctg taaatggtgt tgatattgct      60
tatataaaaa ttccaaatgc aggacaaatg caaccagtaa aagcttttaa aattcataat     120
aaaatatggg ttattccaga aagagataca tttacaaatc ctgaagaagg agatttaaat     180
ccaccaccag aagcaaaaca agttccagtt tcatattatg attcaacata tttaagtaca    240
```

-continued

```
gataatgaaa aagataatta tttaaaggga gttacaaaat tatttgagag aatttattca    300
actgatcttg gaagaatgtt gttaacatca atagtaaggg gaataccatt ttggggtgga    360
agtacaatag atacagaatt aaaagttatt gatactaatt gtattaatgt gatacaacca    420
gatggtagtt atagatcaga agaacttaat ctagtaataa taggaccctc agctgatatt    480
atacagtttg aatgtaaaag cttttggacat gaagttttga atcttacgcg aaatggttat    540
ggctctactc aatacattag atttagccca gattttacat ttggttttga ggagtcactt    600
gaagttgata caaatcctct tttaggtgca ggcaaatttg ctacagatcc agcagtaaca    660
ttagcacatg aacttataca tgctggacat agattatatg gaatagcaat taatccaaat    720
agggttttta aagtaaatac taatgcctat tatgaaatga gtgggttaga agtaagcttt    780
gaggaactta gaacatttgg gggacatgat gcaaagttta tagatagttt acaggaaaac    840
gaatttcgtc tatattatta taataagttt aaagatatag caagtacact aataaagct    900 aaatcaatag taggtactac tgcttcatta cagtatatga aaaatgtttt taaagagaaa    960
tatctcctat ctgaagatac atctggaaaa ttttcggtag ataaattaaa atttgataag   1020
ttatacaaaa tgttaacaga gatttacaca gaggataatt tgttaagtt ttttaaagta   1080 cttaacagaa aaacatattt gaattttgat aaagccgtat ttaagataaa tatagtacct   1140
aaggtaaatt acacaatata tgatggattt aatttaagaa atacaaattt agcagcaaac   1200
tttaatggtc aaaatacaga aattaataat atgaattta ctaaactaaa aaattttact   1260
ggattgtttg aattttataa gttgctatgt gtaagaggga taataacttc taaaactaaa   1320
tcattagata aaggatacaa taaggcatta aatgattttt gtatcaaagt taataattgg   1380
gacttgtttt ttagtcccttc agaagataat tttactaatg atctaaataa aggagaagaa   1440
attacatctg atactaatat agaagcagca gaagaaaata ttagtttaga tttaatacaa   1500
caatattatt taacctttaa ttttgataat gaacctgaaa atatttcaat agaaaatctt   1560
tcaagtgaca ttataggcca attagaactt atgcctaata tagaaagatt tcctaatgga   1620
aaaaagtatg agttagataa atatactatg ttccattatc ttcgtgctca agaatttgaa   1680
catggtaaat ctaggattgc tttaacaaat tctgttaacg aagcattatt aaatcctagt   1740 cgtgttata cattttttc ttcagactat gtaaagaaag ttaataaagc tacggaggca   1800
gctatgtttt taggctgggt agaacaatta gtatatgatt ttaccgatga aactagcgaa   1860
gtaagtacta cggataaaat tgcggatata actataatta ttccatatat aggacctgct   1920
ttaaatatag gtaatatgtt atataaagat gattttgtag gtgctttaat attttcagga   1980
gctgttattc tgttagaatt tataccagag attgcaatac ctgtattagg tactttttgca   2040 cttgtatcat atattgcgaa taaggttcta accgttcaaa caatagataa tgctttaagt   2100
aaaagaaatg aaaaatggga tgaggtctat aaatatatag taacaaattg gttagcaaag   2160
gttaatacac agattgatct aataagaaaa aaaatgaaag aagctttaga aaatcaagca   2220
gaagcaacaa aggctataat aaactatcag tataatcaat atactgagga agagaaaaat   2280
aatattaatt ttaatattga tgatttaagt tcgaaactta atgagtctat aaataaagct   2340
atgattaata taaataaatt tttgaatcaa tgctctgttt catatttaat gaattctatg   2400
atcccttatg gtgttaaacg gttagaagat tttgatgcta gtcttaaaga tgcattatta   2460
aagtatatat atgataatag aggaactta attggtcaag tagatagatt aaagatataa   2520
gttaataata cacttagtac agatatacct tttcagcttt ccaaatacgt agataatcaa   2580
agattattat ctacatttac tgaatatatt aagaatatta ttaatacttc tatattgaat   2640
```

```
ttaagatatg aaagtaatca tttaatagac ttatctaggt atgcatcaaa aataaatatt   2700
ggtagtaaag taaattttga tccaatagat aaaaatcaaa ttcaattatt taatttagaa   2760
agtagtaaaa ttgaggtaat tttaaaaaat gctattgtat ataatagtat gtatgaaaat   2820
tttagtacta gcttttggat aagaattcct aagtatttta acagtataag tctaaataat   2880
gaatatacaa taataaattg tatggaaaat aattcaggat ggaaagtatc acttaattat   2940
ggtgaaataa tctggacttt acaggatact caggaaataa acaaagagt agttttttaaa   3000
tacagtcaaa tgattaatat atcagattat ataaacagat ggattttgt aactatcact   3060
aataatagat aaataactc taaaatttat ataaatggaa gattaataga tcaaaaacca   3120
atttcaaatt taggtaatat tcatgctagt aataatataa tgtttaaatt agatggttgt   3180
agagatacac atagatatat ttggataaaa tattttaatc tttttgataa ggaattaaat   3240
gaaaagaaa tcaagatttt atatgataat caatcaaatt caggtatttt aaaagacttt   3300
tgggtgatt atttcaaata tgataaacca tactatatgt taaatttata tgatccaaat   3360
aaatatgtcg atgtaaataa tgtaggtatt agaggttata tgtatcttaa agggcctaga   3420
ggtagcgtaa tgactacaaa catttattta aattcaagtt tgtataggggg acaaaatttt   3480
attataaaaa aatatgcttc tggaaataaa gataatattg ttagaaataa tgatcgtgta   3540
tatattaatg tagtagttaa aaataaagaa tataggttag ctactaatgc atcacaggca   3600
ggcgtagaaa aaatactaag tgcattagaa atacctgatg taggaaatct aagtcaagta   3660
gtagtaatga agtcaaaaaa tgatcaagga ataacaaata aatgcaaaat gaattacaa    3720
gataataatg ggaatgatat aggctttata ggatttcatc agtttaataa tatagctaaa   3780
ctagtagcaa gtaattggta taatagacaa atagaaagat ctagtaggac tttgggttgc   3840
tcatgggaat ttattcctgt agatgatgga tggggagaaa ggccactgta a             3891
```

<210> SEQ ID NO 2
<211> LENGTH: 1296
<212> TYPE: PRT
<213> ORGANISM: Clostridium botulinum

<400> SEQUENCE: 2

```
Met Pro Phe Val Asn Lys Gln Phe Asn Tyr Lys Asp Pro Val Asn Gly
1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
```

```
            145                 150                 155                 160
        Ile Gln Phe Glu Cys Lys Ser Phe Gly His Glu Val Leu Asn Leu Thr
                        165                 170                 175
        Arg Asn Gly Tyr Gly Ser Thr Gln Tyr Ile Arg Phe Ser Pro Asp Phe
                        180                 185                 190
        Thr Phe Gly Phe Glu Ser Leu Glu Val Asp Thr Asn Pro Leu Leu
                        195                 200                 205
        Gly Ala Gly Lys Phe Ala Thr Asp Pro Ala Val Thr Leu Ala His Glu
                210                 215                 220
        Leu Ile His Ala Gly His Arg Leu Tyr Gly Ile Ala Ile Asn Pro Asn
        225                 230                 235                 240
        Arg Val Phe Lys Val Asn Thr Asn Ala Tyr Tyr Glu Met Ser Gly Leu
                        245                 250                 255
        Glu Val Ser Phe Glu Glu Leu Arg Thr Phe Gly Gly His Asp Ala Lys
                        260                 265                 270
        Phe Ile Asp Ser Leu Gln Glu Asn Glu Phe Arg Leu Tyr Tyr Tyr Asn
                        275                 280                 285
        Lys Phe Lys Asp Ile Ala Ser Thr Leu Asn Lys Ala Lys Ser Ile Val
                290                 295                 300
        Gly Thr Thr Ala Ser Leu Gln Tyr Met Lys Asn Val Phe Lys Glu Lys
        305                 310                 315                 320
        Tyr Leu Leu Ser Glu Asp Thr Ser Gly Lys Phe Ser Val Asp Lys Leu
                        325                 330                 335
        Lys Phe Asp Lys Leu Tyr Lys Met Leu Thr Glu Ile Tyr Thr Glu Asp
                        340                 345                 350
        Asn Phe Val Lys Phe Phe Lys Val Leu Asn Arg Lys Thr Tyr Leu Asn
                        355                 360                 365
        Phe Asp Lys Ala Val Phe Lys Ile Asn Ile Val Pro Lys Val Asn Tyr
                370                 375                 380
        Thr Ile Tyr Asp Gly Phe Asn Leu Arg Asn Thr Asn Leu Ala Ala Asn
        385                 390                 395                 400
        Phe Asn Gly Gln Asn Thr Glu Ile Asn Asn Met Asn Phe Thr Lys Leu
                        405                 410                 415
        Lys Asn Phe Thr Gly Leu Phe Glu Phe Tyr Lys Leu Leu Cys Val Arg
                        420                 425                 430
        Gly Ile Ile Thr Ser Lys Thr Lys Ser Leu Asp Lys Gly Tyr Asn Lys
                        435                 440                 445
        Ala Leu Asn Asp Leu Cys Ile Lys Val Asn Asn Trp Asp Leu Phe Phe
                450                 455                 460
        Ser Pro Ser Glu Asp Asn Phe Thr Asn Asp Leu Asn Lys Gly Glu Glu
        465                 470                 475                 480
        Ile Thr Ser Asp Thr Asn Ile Glu Ala Ala Glu Glu Asn Ile Ser Leu
                        485                 490                 495
        Asp Leu Ile Gln Gln Tyr Tyr Leu Thr Phe Asn Phe Asp Asn Glu Pro
                        500                 505                 510
        Glu Asn Ile Ser Ile Glu Asn Leu Ser Ser Asp Ile Ile Gly Gln Leu
                        515                 520                 525
        Glu Leu Met Pro Asn Ile Glu Arg Phe Pro Asn Gly Lys Lys Tyr Glu
                530                 535                 540
        Leu Asp Lys Tyr Thr Met Phe His Tyr Leu Arg Ala Gln Glu Phe Glu
        545                 550                 555                 560
        His Gly Lys Ser Arg Ile Ala Leu Thr Asn Ser Val Asn Glu Ala Leu
                        565                 570                 575
```

-continued

```
Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
        595                 600                 605

Gln Leu Val Tyr Asp Phe Thr Asp Glu Thr Ser Glu Val Ser Thr Thr
    610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Glu Phe Ile Pro Glu Ile Ala
            660                 665                 670

Ile Pro Val Leu Gly Thr Phe Ala Leu Val Ser Tyr Ile Ala Asn Lys
            675                 680                 685

Val Leu Thr Val Gln Thr Ile Asp Asn Ala Leu Ser Lys Arg Asn Glu
        690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Lys Met Lys Glu Ala Leu
                725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
    755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
            805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
    835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
    915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
            965                 970                 975

Ser Leu Asn Tyr Gly Glu Ile Ile Trp Thr Leu Gln Asp Thr Gln Glu
            980                 985                 990
```

| Ile | Lys | Gln | Arg | Val | Val | Phe | Lys | Tyr | Ser | Gln | Met | Ile | Asn | Ile | Ser |
|  |  | 995 |  |  |  |  | 1000 |  |  |  |  | 1005 |  |  |  |

Asp Tyr Ile Asn Arg Trp Ile Phe Val Thr Ile Thr Asn Asn Arg
1010                    1015                   1020

Leu Asn Asn Ser Lys Ile Tyr Ile Asn Gly Arg Leu Ile Asp Gln
    1025                    1030                   1035

Lys Pro Ile Ser Asn Leu Gly Asn Ile His Ala Ser Asn Asn Ile
    1040                    1045                   1050

Met Phe Lys Leu Asp Gly Cys Arg Asp Thr His Arg Tyr Ile Trp
    1055                    1060                   1065

Ile Lys Tyr Phe Asn Leu Phe Asp Lys Glu Leu Asn Glu Lys Glu
    1070                    1075                   1080

Ile Lys Asp Leu Tyr Asp Asn Gln Ser Asn Ser Gly Ile Leu Lys
    1085                    1090                   1095

Asp Phe Trp Gly Asp Tyr Leu Gln Tyr Asp Lys Pro Tyr Tyr Met
    1100                    1105                   1110

Leu Asn Leu Tyr Asp Pro Asn Lys Tyr Val Asp Val Asn Asn Val
    1115                    1120                   1125

Gly Ile Arg Gly Tyr Met Tyr Leu Lys Gly Pro Arg Gly Ser Val
    1130                    1135                   1140

Met Thr Thr Asn Ile Tyr Leu Asn Ser Ser Leu Tyr Arg Gly Thr
    1145                    1150                   1155

Lys Phe Ile Ile Lys Lys Tyr Ala Ser Gly Asn Lys Asp Asn Ile
    1160                    1165                   1170

Val Arg Asn Asn Asp Arg Val Tyr Ile Asn Val Val Val Lys Asn
    1175                    1180                   1185

Lys Glu Tyr Arg Leu Ala Thr Asn Ala Ser Gln Ala Gly Val Glu
    1190                    1195                   1200

Lys Ile Leu Ser Ala Leu Glu Ile Pro Asp Val Gly Asn Leu Ser
    1205                    1210                   1215

Gln Val Val Val Met Lys Ser Lys Asn Asp Gln Gly Ile Thr Asn
    1220                    1225                   1230

Lys Cys Lys Met Asn Leu Gln Asp Asn Asn Gly Asn Asp Ile Gly
    1235                    1240                   1245

Phe Ile Gly Phe His Gln Phe Asn Asn Ile Ala Lys Leu Val Ala
    1250                    1255                   1260

Ser Asn Trp Tyr Asn Arg Gln Ile Glu Arg Ser Ser Arg Thr Leu
    1265                    1270                   1275

Gly Cys Ser Trp Glu Phe Ile Pro Val Asp Asp Gly Trp Gly Glu
    1280                    1285                   1290

Arg Pro Leu
    1295

<210> SEQ ID NO 3
<211> LENGTH: 3876
<212> TYPE: DNA
<213> ORGANISM: Clostridium botulinum

<400> SEQUENCE: 3
atgccagtta caataaataa ttttaattat aatgatccta ttgataataa taatattatt      60
atgatggagc ctccatttgc gagaggtacg gggagatatt ataaagcttt taaaatcaca     120
gatcgtattt ggataatacc ggaaagatat acttttggat ataaacctga ggattttaat     180
aaaagttccg gtattttaa tagagatgtt tgtgaatatt atgatccaga ttacttaaat     240

```
actaatgata aaaagaatat attttttacaa acaatgatca agttatttaa tagaatcaaa    300
tcaaaaccat tgggtgaaaa gttattagag atgattataa atggtatacc ttatcttgga    360
gatagacgtg ttccactcga agagtttaac acaaacattg ctagtgtaac tgttaataaa    420
ttaatcagta atccaggaga agtggagcga aaaaaaggta ttttcgcaaa tttaataata    480
tttggacctg ggccagtttt aaatgaaaat gagactatag atataggtat acaaaatcat    540
tttgcatcaa gggaaggctt cgggggtata atgcaaatga agttttgccc agaatatgta    600
agcgtattta ataatgttca agaaaacaaa ggcgcaagta tatttaatag acgtggatat    660
ttttcagatc cagccttgat attaatgcat gaacttatac atgttttaca tggattatat    720
ggcattaaag tagatgattt accaattgta ccaaatgaaa aaaaattttt tatgcaatct    780
acagatgcta tacaggcaga agaactatat acatttggag acaagatcc cagcatcata    840 actccttcta cggataaaag tatctatgat aaagttttgc aaaattttag agggatagtt    900
gatagactta acaaggtttt agtttgcata tcagatccta acattaatat taatatatat    960
aaaaataaat ttaaagataa atataaattc gttgaagatt ctgagggaaa atatagtata   1020
gatgtagaaa gttttgataa attatataaa agcttaatgt ttggttttac agaaactaat   1080
atagcagaaa attataaaat aaaaaactaga gcttcttatt ttagtgattc cttaccacca   1140
gtaaaaataa aaaatttatt agataatgaa atctatacta tagaggaagg gtttaatata   1200
tctgataaag atatgaaaa agaatataga ggtcagaata aagctataaa taaacaagct   1260
tatgaagaaa ttagcaagga gcatttggct gtatataaga tacaaatgtg taaaagtgtt   1320
aaagctccag gaatatgtat tgatgttgat aatgaagatt tgttctttat agctgataaa   1380
aatagttttt cagatgattt atctaaaaac gaaagaatag aatataatac acagagtaat   1440
tatatagaaa atgacttccc tataaatgaa ttaattttag atactgattt aataagtaaa   1500
atagaattac caagtgaaaa tacagaatca cttactgatt ttaatgtaga tgttccagta   1560
tatgaaaaac aacccgctat aaaaaaaatt tttacagatg aaaataccat ctttcaatat   1620
ttatactctc agacatttcc tctagatata agagatataa gtttaacatc ttcatttgat   1680
gatgcattat tattttctaa caaagtttat tcattttttt ctatggatta tattaaaact   1740
gctaataaag tggtagaagc aggattattt gcaggttggg tgaaacagat agtaaatgat   1800
tttgtaatcg aagctaataa aagcaatact atggataaaa ttgcagatat atctctaatt   1860
gttccttata taggattagc tttaaatgta ggaaatgaaa cagctaaagg aaattttgaa   1920
aatgcttttg agattgcagg agccagtatt ctactagaat ttataccaga acttttaata   1980
cctgtagttg gagccttttt attagaatca tatattgaca ataaaaataa aattattaaa   2040
acaatagata atgctttaac taaaagaaat gaaaaatgga gtgatatgta cggattaata   2100
gtagcgcaat ggctctcaac agttaatact caatttata caataaaaga gggaatgtat   2160
aaggctttaa attatcaagc acaagcattg gaagaaataa taaaatacag atataatata   2220
tattctgaaa agaaaagtc aaatattaac atcgattta atgatataaa ttctaaactt   2280
aatgagggta ttaaccaagc tatagataat ataaataatt ttataaatgg atgttctgta   2340
tcatatttaa tgaaaaaaat gattccatta gctgtagaaa aattactaga ctttgataat   2400
actctcaaaa aaatttgtt aaattatata gatgaaaata aattatattt gattggaagt   2460
gcagaatatg aaaaatcaaa agtaaataaa tacttgaaaa ccattatgcc gtttgatctt   2520
tcaatatata ccaatgatac aatactaata gaaatgttta ataaatataa tagcgaaatt   2580
ttaaataata ttatcttaaa tttaagatat aaggataata atttaataga tttatcagga   2640
```

```
tatgggcaa aggtagaggt atatgatgga gtcgagctta atgataaaaa tcaatttaaa   2700
ttaactagtt cagcaaatag taagattaga gtgactcaaa atcagaatat catatttaat   2760
agtgtgttcc ttgattttag cgttagcttt tggataagaa tacctaaata taagaatgat   2820
ggtatacaaa attatattca taatgaatat acaataatta attgtatgaa aaataattcg   2880
ggctggaaaa tatctattag gggtaatagg ataatatgga cttttaattga tataaatgga   2940
aaaaccaaat cggtattttt tgaatataac ataagagaag atatatcaga gtatataaat   3000
agatggtttt ttgtaactat tactaataat ttgaataacg ctaaaattta tattaatggt   3060
aagctagaat caaatacaga tattaaagat ataagagaag ttattgctaa tggtgaaata   3120
atatttaaat tagatggtga tatagataga acacaattta tttggatgaa atatttcagt   3180
attttttaata cggaattaag tcaatcaaat attgaagaaa gatataaaat tcaatcatat   3240
agcgaatatt taaaagattt ttgggggaaat cctttaatgt acaataaaga atattatatg   3300
tttaatgcgg ggaataaaaa ttcatatatt aaactaaaga aagattcacc tgtaggtgaa   3360
attttaacac gtagcaaata taatcaaaat tctaaatata taaattatag agatttatat   3420
attggagaaa aatttattat aagaagaaag tcaaattctc aatctataaa tgatgatata   3480
gttagaaaag aagattatat atatctagat tttttttaatt taaatcaaga gtggagagta   3540
tatacctata aatattttaa gaaagaggaa gaaaaattgt ttttagctcc tataagtgat   3600
tctgatgagt tttacaatac tatacaaata aaagaatatg atgaacagcc aacatatagt   3660
tgtcagttgc tttttaaaaa agatgaagaa agtactgatg agataggatt gattggtatt   3720
catcgtttct acgaatctgg aattgtattt gaagagtata agattatttt ttgtataagt   3780
aaatggtact aaaagaggt aaaaaggaaa ccatataatt taaaattggg atgtaattgg   3840
cagtttattc ctaaagatga agggtggact gaataa                             3876
```

<210> SEQ ID NO 4
<211> LENGTH: 1291
<212> TYPE: PRT
<213> ORGANISM: Clostridium botulinum

<400> SEQUENCE: 4

Met Pro Val Thr Ile Asn Asn Phe Asn Tyr Asn Asp Pro Ile Asp Asn
1               5                   10                  15

Asn Asn Ile Ile Met Met Glu Pro Pro Phe Ala Arg Gly Thr Gly Arg
                20                  25                  30

Tyr Tyr Lys Ala Phe Lys Ile Thr Asp Arg Ile Trp Ile Ile Pro Glu
            35                  40                  45

Arg Tyr Thr Phe Gly Tyr Lys Pro Glu Asp Phe Asn Lys Ser Ser Gly
        50                  55                  60

Ile Phe Asn Arg Asp Val Cys Glu Tyr Tyr Asp Pro Asp Tyr Leu Asn
65                  70                  75                  80

Thr Asn Asp Lys Lys Asn Ile Phe Leu Gln Thr Met Ile Lys Leu Phe
                85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125

Phe Asn Thr Asn Ile Ala Ser Val Thr Val Asn Lys Leu Ile Ser Asn
    130                 135                 140

Pro Gly Glu Val Glu Arg Lys Lys Gly Ile Phe Ala Asn Leu Ile Ile

```
            145                 150                 155                 160
        Phe Gly Pro Gly Pro Val Leu Asn Glu Asn Glu Thr Ile Asp Ile Gly
                        165                 170                 175
        Ile Gln Asn His Phe Ala Ser Arg Glu Gly Phe Gly Ile Met Gln
                        180                 185                 190
        Met Lys Phe Cys Pro Glu Tyr Val Ser Val Phe Asn Asn Val Gln Glu
                        195                 200                 205
        Asn Lys Gly Ala Ser Ile Phe Asn Arg Arg Gly Tyr Phe Ser Asp Pro
                210                 215                 220
        Ala Leu Ile Leu Met His Glu Leu Ile His Val Leu His Gly Leu Tyr
        225                 230                 235                 240
        Gly Ile Lys Val Asp Asp Leu Pro Ile Val Pro Asn Glu Lys Lys Phe
                        245                 250                 255
        Phe Met Gln Ser Thr Asp Ala Ile Gln Ala Glu Glu Leu Tyr Thr Phe
                        260                 265                 270
        Gly Gly Gln Asp Pro Ser Ile Ile Thr Pro Ser Thr Asp Lys Ser Ile
                        275                 280                 285
        Tyr Asp Lys Val Leu Gln Asn Phe Arg Gly Ile Val Asp Arg Leu Asn
                290                 295                 300
        Lys Val Leu Val Cys Ile Ser Asp Pro Asn Ile Asn Ile Asn Ile Tyr
        305                 310                 315                 320
        Lys Asn Lys Phe Lys Asp Lys Tyr Lys Phe Val Glu Asp Ser Glu Gly
                        325                 330                 335
        Lys Tyr Ser Ile Asp Val Glu Ser Phe Asp Lys Leu Tyr Lys Ser Leu
                        340                 345                 350
        Met Phe Gly Phe Thr Glu Thr Asn Ile Ala Glu Asn Tyr Lys Ile Lys
                        355                 360                 365
        Thr Arg Ala Ser Tyr Phe Ser Asp Ser Leu Pro Pro Val Lys Ile Lys
                        370                 375                 380
        Asn Leu Leu Asp Asn Glu Ile Tyr Thr Ile Glu Glu Gly Phe Asn Ile
        385                 390                 395                 400
        Ser Asp Lys Asp Met Glu Lys Glu Tyr Arg Gly Gln Asn Lys Ala Ile
                        405                 410                 415
        Asn Lys Gln Ala Tyr Glu Glu Ile Ser Lys Glu His Leu Ala Val Tyr
                        420                 425                 430
        Lys Ile Gln Met Cys Lys Ser Val Lys Ala Pro Gly Ile Cys Ile Asp
                        435                 440                 445
        Val Asp Asn Glu Asp Leu Phe Phe Ile Ala Asp Lys Asn Ser Phe Ser
        450                 455                 460
        Asp Asp Leu Ser Lys Asn Glu Arg Ile Glu Tyr Asn Thr Gln Ser Asn
        465                 470                 475                 480
        Tyr Ile Glu Asn Asp Phe Pro Ile Asn Glu Leu Ile Leu Asp Thr Asp
                        485                 490                 495
        Leu Ile Ser Lys Ile Glu Leu Pro Ser Glu Asn Thr Glu Ser Leu Thr
                        500                 505                 510
        Asp Phe Asn Val Asp Val Pro Val Tyr Glu Lys Gln Pro Ala Ile Lys
                        515                 520                 525
        Lys Ile Phe Thr Asp Glu Asn Thr Ile Phe Gln Tyr Leu Tyr Ser Gln
                        530                 535                 540
        Thr Phe Pro Leu Asp Ile Arg Asp Ile Ser Leu Thr Ser Ser Phe Asp
        545                 550                 555                 560
        Asp Ala Leu Leu Phe Ser Asn Lys Val Tyr Ser Phe Phe Ser Met Asp
                        565                 570                 575
```

```
Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
                645                 650                 655

Glu Leu Leu Ile Pro Val Val Gly Ala Phe Leu Leu Glu Ser Tyr Ile
                660                 665                 670

Asp Asn Lys Asn Lys Ile Ile Lys Thr Ile Asp Asn Ala Leu Thr Lys
                675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
                725                 730                 735

Arg Tyr Asn Ile Tyr Ser Glu Lys Glu Lys Ser Asn Ile Asn Ile Asp
                740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
                805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
                885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
                965                 970                 975

Asp Ile Asn Gly Lys Thr Lys Ser Val Phe Phe Glu Tyr Asn Ile Arg
            980                 985                 990
```

```
Glu Asp Ile Ser Glu Tyr Ile Asn Arg Trp Phe Phe Val Thr Ile Thr
        995                 1000                1005

Asn Asn Leu Asn Asn Ala Lys Ile Tyr Ile Asn Gly Lys Leu Glu
    1010                1015                1020

Ser Asn Thr Asp Ile Lys Asp Ile Arg Glu Val Ile Ala Asn Gly
    1025                1030                1035

Glu Ile Ile Phe Lys Leu Asp Gly Asp Ile Asp Arg Thr Gln Phe
    1040                1045                1050

Ile Trp Met Lys Tyr Phe Ser Ile Phe Asn Thr Glu Leu Ser Gln
    1055                1060                1065

Ser Asn Ile Glu Glu Arg Tyr Lys Ile Gln Ser Tyr Ser Glu Tyr
    1070                1075                1080

Leu Lys Asp Phe Trp Gly Asn Pro Leu Met Tyr Asn Lys Glu Tyr
    1085                1090                1095

Tyr Met Phe Asn Ala Gly Asn Lys Asn Ser Tyr Ile Lys Leu Lys
    1100                1105                1110

Lys Asp Ser Pro Val Gly Glu Ile Leu Thr Arg Ser Lys Tyr Asn
    1115                1120                1125

Gln Asn Ser Lys Tyr Ile Asn Tyr Arg Asp Leu Tyr Ile Gly Glu
    1130                1135                1140

Lys Phe Ile Ile Arg Arg Lys Ser Asn Ser Gln Ser Ile Asn Asp
    1145                1150                1155

Asp Ile Val Arg Lys Glu Asp Tyr Ile Tyr Leu Asp Phe Phe Asn
    1160                1165                1170

Leu Asn Gln Glu Trp Arg Val Tyr Thr Tyr Lys Tyr Phe Lys Lys
    1175                1180                1185

Glu Glu Glu Lys Leu Phe Leu Ala Pro Ile Ser Asp Ser Asp Glu
    1190                1195                1200

Phe Tyr Asn Thr Ile Gln Ile Lys Glu Tyr Asp Glu Gln Pro Thr
    1205                1210                1215

Tyr Ser Cys Gln Leu Leu Phe Lys Lys Asp Glu Glu Ser Thr Asp
    1220                1225                1230

Glu Ile Gly Leu Ile Gly Ile His Arg Phe Tyr Glu Ser Gly Ile
    1235                1240                1245

Val Phe Glu Glu Tyr Lys Asp Tyr Phe Cys Ile Ser Lys Trp Tyr
    1250                1255                1260

Leu Lys Glu Val Lys Arg Lys Pro Tyr Asn Leu Lys Leu Gly Cys
    1265                1270                1275

Asn Trp Gln Phe Ile Pro Lys Asp Glu Gly Trp Thr Glu
    1280                1285                1290

<210> SEQ ID NO 5
<211> LENGTH: 3843
<212> TYPE: DNA
<213> ORGANISM: Clostridium botulinum

<400> SEQUENCE: 5
atgccaataa caattaacaa ctttaattat tcagatcctg ttgataataa aaatatttta    60
tatttagata ctcatttaaa tacattagct aatgagcctg aaaaagcctt tcgcattata   120
gggaatatat gggtaatacc cgatagattt tcaagagatt ctaatccaaa tttaaataaa   180
cctcctcgag ttacaagccc taaaagtggt tattatgatc ctaattattt gagtactgat   240
tctgaaaaag atacattttt aaaagaaatt ataagttat ttaaagaat taactctaga   300 gaaataggag aagaattaat atatagactt gcaacagaca tacccttcc tgggaataac   360
```

```
aatactccaa ttaatacttt tgattttgat gtagatttta acagtgttga tgttaaaact      420
agacaaggta acaactgggt taaaactggt agtataaatc ctagtgttat aataactgga      480
cctagagaaa acattataga cccagaaact tctacgttta aattaactaa caatactttt      540
gcggcacaag aaggatttgg tgctttatca ataatttcaa tatcacctag atttatgcta      600
acatatagta atgcaactaa taatgtagga gagggtagat tttctaagtc tgaattttgc      660
atggatccaa tactaatttt aatgcatgaa cttaatcatg caatgcataa tttatatgga      720
atagctatac caaatgatca aagaatttca tctgtaacta gtaatatttt ttattctcaa      780
tataaggtga aattagagta tgcagaaata tatgcatttg gaggtccaac tatagacctt      840
attcctaaaa gtgcaaggaa atattttgag gaaaaggcat tggattatta tagatccata      900
gctaaaagac ttaatagtat aactactgca aatccttcaa gctttaataa atatataggat    960 gaatataaac agaaacttat tagaaagtat agattcgtag tagaatcttc aggtgaagtt     1020
gcagtagatc gtaataagtt tgctgagtta tataaagaac ttacacaaat atttacagaa     1080
tttaactacg ctaaaatata taatgtacaa aataggaaaa tatatctttc aaatgtatat     1140
actccggtta cggcaaatat attagacgat aatgtttatg atatacaaaa tggatttaac     1200
atacctaaaa gtaatttaaa tgtactattt atgggtcaaa atttatctcg aaatccagca     1260
ttaagaaaag tcaatcctga aaatatgctt tatttattta caaaattttg ccataaagca     1320
atagatggta gatcattata taataaaaca ttagattgta gagagctttt agttaaaaat     1380
actgacttac cctttatagg tgatattagt gatatcaaaa ctgatatatt tttaagcaaa     1440
gatattaatg aagaaactga agttatagac tatccggaca atgtttcagt ggatcaagtt     1500
attctcagta agaatacctc agaacatgga caactagatt tattataccc tattattgaa     1560
ggtgagagtc aagtattacc gggagagaat caagtctttt atgataatag aactcaaaat     1620
gttgattatt tgaattctta ttattaccta gaatctcaaa aactaagtga taatgttgaa     1680
gattttactt ttacgacatc aattgaggaa gctttggata atagtggaaa agtatatact     1740
tactttccta aactagctga taaagtaaat acgggtgttc aaggtggttt atttttaatg     1800
tgggcaaatg atgtagttga agattttact acaaatattc taagaaaaga tacattagat     1860
aaaatatcag atgtatcagc tattattccc tatataggac ctgcattaaa tataagtaat     1920
tctgtaagaa ggggaaattt tactgaagca tttgcagtta ccggtgtaac tatttttatta    1980 gaagcgtttc aagaatttac aatacctgca cttggtgcat tgtgattta tagtaaggtt      2040 caagaaagaa acgagattat taaaactata gataattgtt tagaacaaag gattaaaaga     2100
tggaaagatt catatgaatg gatgatagga acgtggttat ccaggattac tactcaattt     2160
aataatataa gttatcaaat gtatgattct ttaaattatc aggcagatgc aatcaaagat     2220
aaaatagatt tagaatataa aaaatactca ggaagtgata agaaaaatat aaaaagtcaa     2280
gttgaaaatt taaaaatag tttagatata aaaatctcgg aagcaatgaa taatataaat      2340
aaatttatac gagaatgttc tgtaacatac ttatttaaaa atatgctccc taaagtaatt     2400
gatgaattaa ataagtttga tttaaaaact aaaacagaat taattaatct tatagatagt     2460
cataatatta ttctagttgg tgaagtagat agattaaaag caaagtaaa tgagagtttt      2520 gaaaatacaa tacccttta tattttttca tatactaata attctttatt aaaagatata     2580
attaatgaat atttcaatag tattaatgat tcaaaaattt tgagcttaca aaacaaaaaa     2640
aatgctttag tggatacatc aggatataat gcagaagtga ggctagaagg tgatgttcaa     2700
```

```
gttaatacga tatatacaaa tgattttaaa ttaagtagtt caggagataa aattatagta    2760
aatttaaata ataatatttt atatagcgct atttatgaga actctagtgt tagttttttgg  2820 attaagatat ctaaagattt aactaattct cataatgaat atacaataat taatagtata   2880
aaacaaaatt ctgggtggaa attatgtatt aggaatggca atatagaatg gattttacaa   2940
gatattaata gaaagtataa aagtttaatt tttgattata gtgaatcatt aagtcataca   3000
ggatatacaa ataatggtt ttttgttact ataactaata atataatggg gtatatgaaa    3060
ctttatataa atggagaatt aaagcagagt gaaagaattg aagatttaaa tgaggttaag   3120
ttagataaaa ccatagtatt tggaatagat gagaatatag atgagaatca gatgcttttgg  3180 attagagatt ttaatatttt ttctaaagaa ttaagcaatg aagatattaa tattgtatat   3240
gagggacaaa tattaagaaa tgttattaaa gattattggg gaaatccttt gaagtttgat   3300
acagaatatt atattattaa tgataattat atagataggt atatagcacc taaaagtaat   3360
atacttgtac ttgttcagta tccagataga tctaaattat atactggaaa tcctattact   3420
attaaatcag tatctgataa gaatccttat agtagaattt taaatggaga taatatataatg  3480 tttcatatgt tatataatag tgggaaatat atgataataa agatactga tacaatatat    3540 gcaatagaag gaagagagtg ttcaaaaaat tgtgtatatg cattaaaatt acagagtaat   3600
ttaggtaatt atggtatagg tatatttagt ataaaaaata ttgtatctca aaataaatat   3660
tgtagtcaaa ttttctctag ttttatgaaa atacaatgc ttctagcaga tatatataaa    3720
ccttggagat tttcttttga aaatgcatac acgccagttg cagtaactaa ttatgagaca   3780
aaactattat caacttcatc tttttggaaa tttatttcta gggatccagg atgggtagag   3840
taa                                                                 3843
```

<210> SEQ ID NO 6
<211> LENGTH: 1280
<212> TYPE: PRT
<213> ORGANISM: Clostridium botulinum
<400> SEQUENCE: 6

```
Met Pro Ile Thr Ile Asn Asn Phe Asn Tyr Ser Asp Pro Val Asp Asn
1               5                   10                  15

Lys Asn Ile Leu Tyr Leu Asp Thr His Leu Asn Thr Leu Ala Asn Glu
            20                  25                  30

Pro Glu Lys Ala Phe Arg Ile Ile Gly Asn Ile Trp Val Ile Pro Asp
        35                  40                  45

Arg Phe Ser Arg Asp Ser Asn Pro Asn Leu Asn Lys Pro Pro Arg Val
    50                  55                  60

Thr Ser Pro Lys Ser Gly Tyr Tyr Asp Pro Asn Tyr Leu Ser Thr Asp
65                  70                  75                  80

Ser Glu Lys Asp Thr Phe Leu Lys Glu Ile Ile Lys Leu Phe Lys Arg
                85                  90                  95

Ile Asn Ser Arg Glu Ile Gly Glu Glu Leu Ile Tyr Arg Leu Ala Thr
            100                 105                 110

Asp Ile Pro Phe Pro Gly Asn Asn Asn Thr Pro Ile Asn Thr Phe Asp
        115                 120                 125

Phe Asp Val Asp Phe Asn Ser Val Asp Val Lys Thr Arg Gln Gly Asn
    130                 135                 140

Asn Trp Val Lys Thr Gly Ser Ile Asn Pro Ser Val Ile Ile Thr Gly
145                 150                 155                 160

Pro Arg Glu Asn Ile Ile Asp Pro Glu Thr Ser Thr Phe Lys Leu Thr
```

-continued

```
                165                 170                 175
Asn Asn Thr Phe Ala Ala Gln Glu Gly Phe Gly Ala Leu Ser Ile Ile
            180                 185                 190

Ser Ile Ser Pro Arg Phe Met Leu Thr Tyr Ser Asn Ala Thr Asn Asn
        195                 200                 205

Val Gly Glu Gly Arg Phe Ser Lys Ser Glu Phe Cys Met Asp Pro Ile
210                 215                 220

Leu Ile Leu Met His Glu Leu Asn His Ala Met His Asn Leu Tyr Gly
225                 230                 235                 240

Ile Ala Ile Pro Asn Asp Gln Arg Ile Ser Ser Val Thr Ser Asn Ile
            245                 250                 255

Phe Tyr Ser Gln Tyr Lys Val Lys Leu Glu Tyr Ala Glu Ile Tyr Ala
        260                 265                 270

Phe Gly Gly Pro Thr Ile Asp Leu Ile Pro Lys Ser Ala Arg Lys Tyr
    275                 280                 285

Phe Glu Glu Lys Ala Leu Asp Tyr Tyr Arg Ser Ile Ala Lys Arg Leu
290                 295                 300

Asn Ser Ile Thr Thr Ala Asn Pro Ser Ser Phe Asn Lys Tyr Ile Gly
305                 310                 315                 320

Glu Tyr Lys Gln Lys Leu Ile Arg Lys Tyr Arg Phe Val Val Glu Ser
            325                 330                 335

Ser Gly Glu Val Ala Val Asp Arg Asn Lys Phe Ala Glu Leu Tyr Lys
        340                 345                 350

Glu Leu Thr Gln Ile Phe Thr Glu Phe Asn Tyr Ala Lys Ile Tyr Asn
    355                 360                 365

Val Gln Asn Arg Lys Ile Tyr Leu Ser Asn Val Tyr Thr Pro Val Thr
370                 375                 380

Ala Asn Ile Leu Asp Asp Asn Val Tyr Asp Ile Gln Asn Gly Phe Asn
385                 390                 395                 400

Ile Pro Lys Ser Asn Leu Asn Val Leu Phe Met Gly Gln Asn Leu Ser
            405                 410                 415

Arg Asn Pro Ala Leu Arg Lys Val Asn Pro Glu Asn Met Leu Tyr Leu
        420                 425                 430

Phe Thr Lys Phe Cys His Lys Ala Ile Asp Gly Arg Ser Leu Tyr Asn
    435                 440                 445

Lys Thr Leu Asp Cys Arg Glu Leu Leu Val Lys Asn Thr Asp Leu Pro
450                 455                 460

Phe Ile Gly Asp Ile Ser Asp Ile Lys Thr Asp Ile Phe Leu Ser Lys
465                 470                 475                 480

Asp Ile Asn Glu Glu Thr Glu Val Ile Asp Tyr Pro Asp Asn Val Ser
            485                 490                 495

Val Asp Gln Val Ile Leu Ser Lys Asn Thr Ser Glu His Gly Gln Leu
        500                 505                 510

Asp Leu Leu Tyr Pro Ile Ile Glu Gly Glu Ser Gln Val Leu Pro Gly
    515                 520                 525

Glu Asn Gln Val Phe Tyr Asp Asn Arg Thr Gln Asn Val Asp Tyr Leu
530                 535                 540

Asn Ser Tyr Tyr Tyr Leu Glu Ser Gln Lys Leu Ser Asp Asn Val Glu
545                 550                 555                 560

Asp Phe Thr Phe Thr Thr Ser Ile Glu Glu Ala Leu Asp Asn Ser Gly
            565                 570                 575

Lys Val Tyr Thr Tyr Phe Pro Lys Leu Ala Asp Lys Val Asn Thr Gly
        580                 585                 590
```

```
Val Gln Gly Gly Leu Phe Leu Met Trp Ala Asn Asp Val Val Glu Asp
            595                 600                 605

Phe Thr Thr Asn Ile Leu Arg Lys Asp Thr Leu Asp Lys Ile Ser Asp
610                 615                 620

Val Ser Ala Ile Ile Pro Tyr Ile Gly Pro Ala Leu Asn Ile Ser Asn
625                 630                 635                 640

Ser Val Arg Arg Gly Asn Phe Thr Glu Ala Phe Ala Val Thr Gly Val
                645                 650                 655

Thr Ile Leu Leu Glu Ala Phe Gln Glu Phe Thr Ile Pro Ala Leu Gly
            660                 665                 670

Ala Phe Val Ile Tyr Ser Lys Val Gln Glu Arg Asn Glu Ile Ile Lys
            675                 680                 685

Thr Ile Asp Asn Cys Leu Glu Gln Arg Ile Lys Arg Trp Lys Asp Ser
            690                 695                 700

Tyr Glu Trp Met Ile Gly Thr Trp Leu Ser Arg Ile Thr Thr Gln Phe
705                 710                 715                 720

Asn Asn Ile Ser Tyr Gln Met Tyr Asp Ser Leu Asn Tyr Gln Ala Asp
                725                 730                 735

Ala Ile Lys Asp Lys Ile Asp Leu Glu Tyr Lys Lys Tyr Ser Gly Ser
            740                 745                 750

Asp Lys Glu Asn Ile Lys Ser Gln Val Glu Asn Leu Lys Asn Ser Leu
            755                 760                 765

Asp Ile Lys Ile Ser Glu Ala Met Asn Asn Ile Asn Lys Phe Ile Arg
            770                 775                 780

Glu Cys Ser Val Thr Tyr Leu Phe Lys Asn Met Leu Pro Lys Val Ile
785                 790                 795                 800

Asp Glu Leu Asn Lys Phe Asp Leu Lys Thr Lys Thr Glu Leu Ile Asn
                805                 810                 815

Leu Ile Asp Ser His Asn Ile Ile Leu Val Gly Glu Val Asp Arg Leu
            820                 825                 830

Lys Ala Lys Val Asn Glu Ser Phe Glu Asn Thr Ile Pro Phe Asn Ile
            835                 840                 845

Phe Ser Tyr Thr Asn Asn Ser Leu Leu Lys Asp Ile Ile Asn Glu Tyr
850                 855                 860

Phe Asn Ser Ile Asn Asp Ser Lys Ile Leu Ser Leu Gln Asn Lys Lys
865                 870                 875                 880

Asn Ala Leu Val Asp Thr Ser Gly Tyr Asn Ala Glu Val Arg Leu Glu
                885                 890                 895

Gly Asp Val Gln Val Asn Thr Ile Tyr Thr Asn Asp Phe Lys Leu Ser
            900                 905                 910

Ser Ser Gly Asp Lys Ile Ile Val Asn Leu Asn Asn Asn Ile Leu Tyr
            915                 920                 925

Ser Ala Ile Tyr Glu Asn Ser Ser Val Ser Phe Trp Ile Lys Ile Ser
            930                 935                 940

Lys Asp Leu Thr Asn Ser His Asn Glu Tyr Thr Ile Ile Asn Ser Ile
945                 950                 955                 960

Lys Gln Asn Ser Gly Trp Lys Leu Cys Ile Arg Asn Gly Asn Ile Glu
                965                 970                 975

Trp Ile Leu Gln Asp Ile Asn Arg Lys Tyr Lys Ser Leu Ile Phe Asp
            980                 985                 990

Tyr Ser Glu Ser Leu Ser His  Thr Gly Tyr Thr Asn Lys Trp Phe Phe
            995                 1000                 1005
```

| | | | | | | | | | | |
|---|---|---|---|---|---|---|---|---|---|---|
| Val | Thr | Ile | Thr | Asn | Asn | Ile | Met | Gly | Tyr | Met | Lys | Leu | Tyr | Ile |
| 1010 | | | | | 1015 | | | | | 1020 | | | | |

Asn Gly Glu Leu Lys Gln Ser Glu Arg Ile Glu Asp Leu Asn Glu
1025 1030 1035

Val Lys Leu Asp Lys Thr Ile Val Phe Gly Ile Asp Glu Asn Ile
1040 1045 1050

Asp Glu Asn Gln Met Leu Trp Ile Arg Asp Phe Asn Ile Phe Ser
1055 1060 1065

Lys Glu Leu Ser Asn Glu Asp Ile Asn Ile Val Tyr Glu Gly Gln
1070 1075 1080

Ile Leu Arg Asn Val Ile Lys Asp Tyr Trp Gly Asn Pro Leu Lys
1085 1090 1095

Phe Asp Thr Glu Tyr Tyr Ile Ile Asn Asp Asn Tyr Ile Asp Arg
1100 1105 1110

Tyr Ile Ala Pro Lys Ser Asn Ile Leu Val Leu Val Gln Tyr Pro
1115 1120 1125

Asp Arg Ser Lys Leu Tyr Thr Gly Asn Pro Ile Thr Ile Lys Ser
1130 1135 1140

Val Ser Asp Lys Asn Pro Tyr Ser Arg Ile Leu Asn Gly Asp Asn
1145 1150 1155

Ile Met Phe His Met Leu Tyr Asn Ser Gly Lys Tyr Met Ile Ile
1160 1165 1170

Arg Asp Thr Asp Thr Ile Tyr Ala Ile Glu Gly Arg Glu Cys Ser
1175 1180 1185

Lys Asn Cys Val Tyr Ala Leu Lys Leu Gln Ser Asn Leu Gly Asn
1190 1195 1200

Tyr Gly Ile Gly Ile Phe Ser Ile Lys Asn Ile Val Ser Gln Asn
1205 1210 1215

Lys Tyr Cys Ser Gln Ile Phe Ser Ser Phe Met Lys Asn Thr Met
1220 1225 1230

Leu Leu Ala Asp Ile Tyr Lys Pro Trp Arg Phe Ser Phe Glu Asn
1235 1240 1245

Ala Tyr Thr Pro Val Ala Val Thr Asn Tyr Glu Thr Lys Leu Leu
1250 1255 1260

Ser Thr Ser Ser Phe Trp Lys Phe Ile Ser Arg Asp Pro Gly Trp
1265 1270 1275

Val Glu
1280

<210> SEQ ID NO 7
<211> LENGTH: 3858
<212> TYPE: DNA
<213> ORGANISM: Clostridium botulinum

<400> SEQUENCE: 7

```
atgacatggc cagtaaaaga ttttaattat agtgatcctg ttaatgacaa tgatatatta      60
tatttaagaa taccacaaaa taagttaatt actacacctg taaaagcttt tatgattact     120
caaaatattt gggtaatacc agaaagattt tcatcagata ctaatccaag tttaagtaaa     180
ccgcctagac ctacttcaaa gtatcaaagt tattatgatc ctagttattt atctactgat     240
gagcaaaaag atacattttt aaagggatt ataaaattat ttaaaagaat aatgaaaga     300
gatataggaa aaaattaat aaattattta gtagttggtt cacctttat gggagattca     360
agtacgcctg aagatacatt tgattttaca cgtcatacta ctaatattgc agttgaaaag     420
```

| | |
|---|---|
| tttgaaaatg gtagttggaa agtaacaaat attataacac caagtgtatt gatatttgga | 480 |
| ccacttccta atatattaga ctatacagca tcccttacat tgcaaggaca acaatcaaat | 540 |
| ccatcatttg aagggtttgg aacattatct atactaaaag tagcacctga attttttgtta | 600 |
| acatttagtg atgtaacatc taatcaaagt tcagctgtat taggcaaatc tatattttgt | 660 |
| atggatccag taatagcttt aatgcatgag ttaacacatt ctttgcatca attgtatgga | 720 |
| ataaatatac catctgataa aaggattcgt ccacaagtta gcgagggatt tttttctcaa | 780 |
| gatggaccca acgtacaatt tgaggaatta tacacatttg gaggatcaga tgttgaaata | 840 |
| atacctcaaa ttgaaagatt acaattaaga gaaaaagcat taggtcacta aaagatata | 900 |
| gcgaaaagac ttaataatat taataaaact attccttcta gttggagtag taatatagat | 960 |
| aaatataaaa aaatattttc tgaaaagtat aattttgata agataatac aggaaatttt | 1020 |
| gttgtaaata ttgataaatt caatagctta tattcagact tgactaatgt tatgtcagaa | 1080 |
| gttgtttatt cttcgcaata taatgttaaa aacaggactc attattttc aaagcattat | 1140 |
| ctacctgtat ttgcaaatat attagatgat aatatttata ctataataaa cggttttaat | 1200 |
| ttaacaacta aaggttttaa tatagaaaat tcgggtcaga atatagaaag gaatcctgca | 1260 |
| ctacaaaaac ttagttcaga aagtgtagta gatttgttta caaagtatg tttaagatta | 1320 |
| acaagaaata gtagagatga ttcaacatgt attcaagtta aaaataatac attaccttat | 1380 |
| gtagctgata aagatagcat ttcacaagaa atatttgaaa gtcaaattat tacagatgag | 1440 |
| actaatgtag aaaattattc agataattt tcattagatg aatctatttt agatgcaaaa | 1500 |
| gtccctacta atcctgaagc agtagatcca ctgttaccca atgttaatat ggaacctta | 1560 |
| aatgttccag gtgaagaaga agtattttat gatgatatta ctaaagatgt tgattattta | 1620 |
| aactcttatt attattgga gcccaaaaaa ttaagtaata atgttgaaaa tattactctt | 1680 |
| acaacttcag ttgaagaagc attaggttat agcaataaga tatacacatt tttacctagc | 1740 |
| ttagctgaaa aagtgaataa aggtgttcaa gcaggttat tcttaaattg ggcgaatgaa | 1800 |
| gtagttgagg attttactac aaatattatg aaaaaagata cattggataa aatatcagat | 1860 |
| gtatcagcca taattccata tataggacct gccttaaata taggaaattc agcattaagg | 1920 |
| ggaaacttta agcaagcatt tgcaacagct ggtgtagctt ttttgttaga aggattca | 1980 |
| gagtttacaa tacctgcact cggtgtattt acctttata gttctattca agaaagagag | 2040 |
| aaaattatta aaactataga aaattgttta gaacaaagag ttaagagatg gaaagattca | 2100 |
| tatcaatgga tggtatcaaa ttggttgtca agaattacta ctcgatttaa tcatataagt | 2160 |
| tatcaaatgt atgattcttt gagttatcag gcagatgcaa tcaaagctaa aatagattta | 2220 |
| gaatataaaa aatactcagg aagtgataaa gaaaatataa aaagtcaagt tgaaaattta | 2280 |
| aaaaatagtt tagatgtaaa aatctcggaa gcaatgaata atataaataa atttatacga | 2340 |
| gaatgttctg taacatactt atttaaaaat atgctcccta agtaattga tgaattaaat | 2400 |
| aagtttgatt taaaaactaa aacagaatta attaatctta tagatagtca taatattatt | 2460 |
| ctagttggtg aagtagatag attaaaagca aagtaaatg agagttttga aaatacaata | 2520 |
| cccttttaata ttttttcata tactaataat tctttattaa aagatatgat taatgaatat | 2580 |
| ttcaatagta ttaatgattc aaaaattttg agcttacaaa ataaaaaaaa tactttgatg | 2640 |
| gatacatcag gatataacgc agaagtgaga gtagaaggca atgttcagct taatccaata | 2700 |
| tttccatttg actttaaatt aggtagttca ggggatgata gaggtaaagt tatagtaacc | 2760 |
| cagaatgaaa atattgtata taatgctatg tatgaaagtt ttagtattag tttttggatt | 2820 |

```
aggataaaata aatgggtaag taatttacct ggatatacta taattgatag tgttaaaaat    2880
aactcaggtt ggagtatagg tattattagt aattttttag tgtttacttt aaaacaaaat    2940
gaaaatagtg aacaagatat aaactttagt tatgatatat caaagaatgc tgcgggatat    3000
aataaatggt tttttgtaac tattactacc aatatgatgg gaaatgtgat gatttatata    3060
aatggaaaat taatagatac tataaaagtt aaagagttaa ctggaattaa ttttagcaaa    3120
actataacat ttcaaatgaa taaaattcca aatactggct taattacctc agattctgat    3180
aacatcaata tgtggataag ggattttttat atctttgcta aagaattaga tgataaagat    3240
attaatatat tatttaatag cttgcaatat actaatgttg taaagatta ttggggaaat     3300 gatttaagat atgataaaga atattacatg attaacgtaa attatatgaa tagatatatg    3360
tctaaaaaag gcaatggaat tgttttttaat acacgtaaaa ataataatga cttcaatgaa    3420
ggatataaaa ttataataaa aagaattaga ggaaatacaa atgatactag agtacgagga    3480
gaaaatgtat tatattttaa tactacaatt gataacaaac aatatagttt aggtatgtat    3540
aaaccttcta gaaatctagg gactgattta gttccactag gtgcattgga tcaaccaatg    3600
gatgagatac gtaaatatgg ttcgtttata atacaaccat gcaatacttt tgattactat    3660
gcatcacaat tattttttgtc aagtaatgca acaacaaata ggcttggaat actatcaatt    3720
ggtagttata gtttcaaact tggagatgac tattggttta atcacgaata tttaattcct    3780
gttataaaaa tagagcatta tgcttcatta ttagaatcaa catcaactca ttgggttttt    3840
gtacctgcaa gtgaataa                                                   3858

<210> SEQ ID NO 8
<211> LENGTH: 1285
<212> TYPE: PRT
<213> ORGANISM: Clostridium botulinum

<400> SEQUENCE: 8

Met Thr Trp Pro Val Lys Asp Phe Asn Tyr Ser Asp Pro Val Asn Asp
1               5                   10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
```

```
            180                 185                 190
Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
        210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Ser Asp Val Glu Ile Ile Pro Gln Ile Glu Arg Leu Gln
        275                 280                 285

Leu Arg Glu Lys Ala Leu Gly His Tyr Lys Asp Ile Ala Lys Arg Leu
        290                 295                 300

Asn Asn Ile Asn Lys Thr Ile Pro Ser Ser Trp Ser Ser Asn Ile Asp
305                 310                 315                 320

Lys Tyr Lys Lys Ile Phe Ser Glu Lys Tyr Asn Phe Asp Lys Asp Asn
                325                 330                 335

Thr Gly Asn Phe Val Val Asn Ile Asp Lys Phe Asn Ser Leu Tyr Ser
            340                 345                 350

Asp Leu Thr Asn Val Met Ser Glu Val Val Tyr Ser Ser Gln Tyr Asn
        355                 360                 365

Val Lys Asn Arg Thr His Tyr Phe Ser Lys His Tyr Leu Pro Val Phe
        370                 375                 380

Ala Asn Ile Leu Asp Asp Asn Ile Tyr Thr Ile Ile Asn Gly Phe Asn
385                 390                 395                 400

Leu Thr Thr Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Arg Asn Ser Arg Asp Asp Ser
        435                 440                 445

Thr Cys Ile Gln Val Lys Asn Asn Thr Leu Pro Tyr Val Ala Asp Lys
        450                 455                 460

Asp Ser Ile Ser Gln Glu Ile Phe Glu Ser Gln Ile Ile Thr Asp Glu
465                 470                 475                 480

Thr Asn Val Glu Asn Tyr Ser Asp Asn Phe Ser Leu Asp Glu Ser Ile
                485                 490                 495

Leu Asp Ala Lys Val Pro Thr Asn Pro Glu Ala Val Asp Pro Leu Leu
            500                 505                 510

Pro Asn Val Asn Met Glu Pro Leu Asn Val Pro Gly Glu Glu Val
        515                 520                 525

Phe Tyr Asp Asp Ile Thr Lys Asp Val Asp Tyr Leu Asn Ser Tyr Tyr
        530                 535                 540

Tyr Leu Glu Ala Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605
```

```
Ile Met Lys Lys Asp Thr Leu Asp Lys Ile Ser Asp Val Ser Ala Ile
    610                 615                 620
Ile Pro Tyr Ile Gly Pro Ala Leu Asn Ile Gly Asn Ser Ala Leu Arg
625                 630                 635                 640
Gly Asn Phe Lys Gln Ala Phe Ala Thr Ala Gly Val Ala Phe Leu Leu
                645                 650                 655
Glu Gly Phe Pro Glu Phe Thr Ile Pro Ala Leu Gly Val Phe Thr Phe
                660                 665                 670
Tyr Ser Ser Ile Gln Glu Arg Glu Lys Ile Ile Lys Thr Ile Glu Asn
        675                 680                 685
Cys Leu Glu Gln Arg Val Lys Arg Trp Lys Asp Ser Tyr Gln Trp Met
    690                 695                 700
Val Ser Asn Trp Leu Ser Arg Ile Thr Thr Arg Phe Asn His Ile Ser
705                 710                 715                 720
Tyr Gln Met Tyr Asp Ser Leu Ser Tyr Gln Ala Asp Ala Ile Lys Ala
                725                 730                 735
Lys Ile Asp Leu Glu Tyr Lys Lys Tyr Ser Gly Ser Asp Lys Glu Asn
                740                 745                 750
Ile Lys Ser Gln Val Glu Asn Leu Lys Asn Ser Leu Asp Val Lys Ile
        755                 760                 765
Ser Glu Ala Met Asn Asn Ile Asn Lys Phe Ile Arg Glu Cys Ser Val
    770                 775                 780
Thr Tyr Leu Phe Lys Asn Met Leu Pro Lys Val Ile Asp Glu Leu Asn
785                 790                 795                 800
Lys Phe Asp Leu Lys Thr Lys Thr Glu Leu Ile Asn Leu Ile Asp Ser
                805                 810                 815
His Asn Ile Ile Leu Val Gly Glu Val Asp Arg Leu Lys Ala Lys Val
                820                 825                 830
Asn Glu Ser Phe Glu Asn Thr Ile Pro Phe Asn Ile Phe Ser Tyr Thr
        835                 840                 845
Asn Asn Ser Leu Leu Lys Asp Met Ile Asn Glu Tyr Phe Asn Ser Ile
    850                 855                 860
Asn Asp Ser Lys Ile Leu Ser Leu Gln Asn Lys Lys Asn Thr Leu Met
865                 870                 875                 880
Asp Thr Ser Gly Tyr Asn Ala Glu Val Arg Val Glu Gly Asn Val Gln
                885                 890                 895
Leu Asn Pro Ile Phe Pro Phe Asp Phe Lys Leu Gly Ser Ser Gly Asp
                900                 905                 910
Asp Arg Gly Lys Val Ile Val Thr Gln Asn Glu Asn Ile Val Tyr Asn
        915                 920                 925
Ala Met Tyr Glu Ser Phe Ser Ile Ser Phe Trp Ile Arg Ile Asn Lys
    930                 935                 940
Trp Val Ser Asn Leu Pro Gly Tyr Thr Ile Ile Asp Ser Val Lys Asn
945                 950                 955                 960
Asn Ser Gly Trp Ser Ile Gly Ile Ile Ser Asn Phe Leu Val Phe Thr
                965                 970                 975
Leu Lys Gln Asn Glu Asn Ser Glu Gln Asp Ile Asn Phe Ser Tyr Asp
                980                 985                 990
Ile Ser Lys Asn Ala Ala Gly Tyr  Asn Lys Trp Phe Phe  Val Thr Ile
        995                 1000                1005
Thr Thr Asn Met Met Gly Asn  Met Met Ile Tyr Ile  Asn Gly Lys
       1010                1015                1020
```

| | | | | | | | | | | | |
|---|---|---|---|---|---|---|---|---|---|---|---|
| Leu | Ile | Asp | Thr | Ile | Lys | Val | Lys | Glu | Leu | Thr | Gly | Ile | Asn | Phe |
| 1025 | | | | 1030 | | | | | 1035 | | |

Ser Lys Thr Ile Thr Phe Gln Met Asn Lys Ile Pro Asn Thr Gly
    1040                1045                1050

Leu Ile Thr Ser Asp Ser Asp Asn Ile Asn Met Trp Ile Arg Asp
    1055                1060                1065

Phe Tyr Ile Phe Ala Lys Glu Leu Asp Asp Lys Asp Ile Asn Ile
    1070                1075                1080

Leu Phe Asn Ser Leu Gln Tyr Thr Asn Val Val Lys Asp Tyr Trp
    1085                1090                1095

Gly Asn Asp Leu Arg Tyr Asp Lys Glu Tyr Tyr Met Ile Asn Val
    1100                1105                1110

Asn Tyr Met Asn Arg Tyr Met Ser Lys Lys Gly Asn Gly Ile Val
    1115                1120                1125

Phe Asn Thr Arg Lys Asn Asn Asp Phe Asn Glu Gly Tyr Lys
    1130                1135                1140

Ile Ile Ile Lys Arg Ile Arg Gly Asn Thr Asn Asp Thr Arg Val
    1145                1150                1155

Arg Gly Glu Asn Val Leu Tyr Phe Asn Thr Thr Ile Asp Asn Lys
    1160                1165                1170

Gln Tyr Ser Leu Gly Met Tyr Lys Pro Ser Arg Asn Leu Gly Thr
    1175                1180                1185

Asp Leu Val Pro Leu Gly Ala Leu Asp Gln Pro Met Asp Glu Ile
    1190                1195                1200

Arg Lys Tyr Gly Ser Phe Ile Ile Gln Pro Cys Asn Thr Phe Asp
    1205                1210                1215

Tyr Tyr Ala Ser Gln Leu Phe Leu Ser Ser Asn Ala Thr Thr Asn
    1220                1225                1230

Arg Leu Gly Ile Leu Ser Ile Gly Ser Tyr Ser Phe Lys Leu Gly
    1235                1240                1245

Asp Asp Tyr Trp Phe Asn His Glu Tyr Leu Ile Pro Val Ile Lys
    1250                1255                1260

Ile Glu His Tyr Ala Ser Leu Leu Glu Ser Thr Ser Thr His Trp
    1265                1270                1275

Val Phe Val Pro Ala Ser Glu
    1280                1285

<210> SEQ ID NO 9
<211> LENGTH: 3756
<212> TYPE: DNA
<213> ORGANISM: Clostridium botulinum

<400> SEQUENCE: 9
atgccaaaaa ttaatagttt taattataat gatcctgtta atgatagaac aattttatat      60
attaaaccag gcggttgtca agaattttat aaatcattta atattatgaa aaatatttgg     120
ataattccag agagaaatgt aattggtaca accccccaag attttcatcc gcctacttca     180
ttaaaaaatg gagatagtag ttattatgac cctaattatt acaaagtga tgaagaaaag     240 gatagatttt taaaaatagt cacaaaaata tttaatagaa taataataa tctttcagga     300 gggattttat tagaagaact gtcaaaagct aatccatatt tagggaatga ataatactcca     360 gataatcaat tccatattgg tgatgcatca gcagttgaga ttaaattctc aaatggtagc     420
caagacatac tattacctaa tgttattata atgggagcag agcctgattt atttgaaact     480
aacagttcca atatttctct aagaaataat tatatgccaa gcaatcaccg ttttggatca     540

```
atagctatag taacattctc acctgaatat tcttttagat ttaatgataa ttgtatgaat    600
gaatttattc aagatcctgc tcttacatta atgcatgaat taatacattc attacatgga    660
ctatatgggg ctaaagggat tactacaaag tatactataa cacaaaaaca aaatcccta     720 ataacaaata taagaggtac aaatattgaa gaattcttaa cttttggagg tactgattta    780
aacattatta ctagtgctca gtccaatgat atctatacta atcttctagc tgattataaa    840
aaaatagcgt ctaaacttag caaagtacaa gtatctaatc cactacttaa tccttataaa    900 gatgttttg aagcaaagta tggattagat aaagatgcta gcggaattta ttcggtaaat    960
ataaacaaat ttaatgatat ttttaaaaaa ttatacagct ttacggaatt tgatttacga   1020
actaaatttc aagttaaatg taggcaaact tatattggac agtataaata cttcaaactt   1080
tcaaacttgt taaatgattc tatttataat atatcagaag gctataatat aaataattta   1140
aaggtaaatt ttagaggaca gaatgcaaat ttaaatccta gaattattac accaattaca   1200
ggtagaggac tagtaaaaaa aatcattaga ttttgtaaaa atattgtttc tgtaaaaggc   1260
ataaggaaat caatatgtat cgaaataaat aatggtgagt tattttttgt ggcttccgag   1320
aatagttata atgatgataa tataaatact cctaaagaaa ttgacgatac agtaacttca   1380
aataataatt atgaaaatga tttagatcag gttattttaa attttaatag tgaatcagca   1440
cctggacttt cagatgaaaa attaaattta actatccaaa atgatgctta tataccaaaa   1500
tatgattcta atggaacaag tgatatagaa caacatgatg ttaatgaact taatgtatt   1560 ttctatttag atgcacagaa agtgcccgaa ggtgaaaata atgtcaatct cacctcttca   1620
attgatacag cattattaga acaacctaaa atatatacat tttttcatc agaatttatt    1680 aataatgtca ataaacctgt gcaagcagca ttatttgtaa gctggataca acaagtgtta   1740
gtagatttta ctactgaagc taaccaaaaa agtactgttg ataaaattgc agatatttct   1800
atagttgttc catatatagg tcttgcttta aatataggaa atgaagcaca aaaaggaaat   1860
tttaaagatg cacttgaatt attaggagca ggtatttat tagaatttga acccgagctt    1920
ttaattccta caattttagt attcacgata aaatctttt taggttcatc tgataataaa    1980
aataaagtta ttaaagcaat aaataatgca ttgaaagaaa gagatgaaaa atggaaagaa   2040
gtatatagtt ttatagtatc gaattggatg actaaaatta atacacaatt taataaaaga   2100
aaagaacaaa tgtatcaagc tttacaaaat caagtaaatg caattaaaac aataatagaa   2160
tctaagtata atagttatac tttagaggaa aaaaatgagc ttacaaataa atatgatatt   2220
aagcaaatag aaaatgaact taatcaaaag gtttctatag caatgaataa tatagacagg   2280
ttcttaactg aaagttctat atcctattta atgaaaataa taaatgaagt aaaaattaat   2340
aaattaagag aatatgatga gaatgtcaaa acgtatttat tgaattatat tatacaacat   2400
ggatcaatct tgggagagag tcagcaagaa ctaaattcta tggtaactga taccctaaat   2460
aatagtattc cttttaagct ttcttcttat acagatgata aaatttttaat ttcatattt    2520 aataaattct ttaagagaat taaagtagt tcagttttaa atatgagata taaaaatgat    2580
aaatacgtag atacttcagg atatgattca aatataaata ttaatggaga tgtatataaa   2640
tatccaacta ataaaaatca atttggaata tataatgata aacttagtga agttaatata   2700
tctcaaaatg attacattat atatgataat aaatataaaa attttagtat tagtttttgg   2760
gtaagaattc ctaactatga taataagata gtaaatgtta ataatgaata cactataata   2820
aattgtatga gagataataa ttcaggatgg aaagtatctc ttaatcataa tgaaataatt   2880
```

-continued

```
tggacattcg aagataatcg aggaattaat caaaaattag catttaacta tggtaacgca    2940
aatggtattt ctgattatat aaataagtgg attttttgtaa ctataactaa tgatagatta    3000
ggagattcta aactttatat taatggaaat ttaatagatc aaaaatcaat tttaaattta    3060
ggtaatattc atgttagtga caatatatta tttaaaatag ttaattgtag ttatacaaga    3120
tatattggta ttagatattt taatatttt gataaagaat tagatgaaac agaaattcaa    3180
actttatata gcaatgaacc taatacaaat attttgaagg attttggggg aaattatttg    3240
ctttatgaca agaatactta ttattaaat gtgttaaaac caaataactt tattgatagg    3300
agaaaagatt ctactttaag cattaataat ataagaagca ctattctttt agctaataga    3360
ttatatagtg gaataaaagt taaaatacaa agagttaata atagtagtac taacgataat    3420
cttgttagaa agaatgatca ggtatatatt aattttgtag ccagcaaaac tcacttattt    3480
ccattatatg ctgatacagc taccacaaat aaagagaaaa caataaaaat atcatcatct    3540
ggcaatagat taatcaagt agtagttatg aattcagtag gaaattgtac aatgaatttt    3600
aaaaataata atggaaataa tattgggttg ttaggtttca aggcagatac tgtcgttgct    3660
agtacttggt attatacaca tatgagagat catacaaaca gcaatggatg tttttggaac    3720
tttatttctg aagaacatgg atggcaagaa aaataa                             3756
```

<210> SEQ ID NO 10
<211> LENGTH: 1251
<212> TYPE: PRT
<213> ORGANISM: Clostridium botulinum

<400> SEQUENCE: 10

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Arg Phe Gly Ser Ile Ala Ile Val Thr Phe Ser Pro Glu Tyr Ser Phe
            180                 185                 190

Arg Phe Asn Asp Asn Cys Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220
```

```
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
            245                 250                 255

Gly Thr Asp Leu Asn Ile Ile Thr Ser Ala Gln Ser Asn Asp Ile Tyr
        260                 265                 270

Thr Asn Leu Leu Ala Asp Tyr Lys Lys Ile Ala Ser Lys Leu Ser Lys
    275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
            325                 330                 335

Phe Asp Leu Arg Thr Lys Phe Gln Val Lys Cys Arg Gln Thr Tyr Ile
        340                 345                 350

Gly Gln Tyr Lys Tyr Phe Lys Leu Ser Asn Leu Leu Asn Asp Ser Ile
    355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
            405                 410                 415

Ser Val Lys Gly Ile Arg Lys Ser Ile Cys Ile Glu Ile Asn Asn Gly
        420                 425                 430

Glu Leu Phe Phe Val Ala Ser Glu Asn Ser Tyr Asn Asp Asp Asn Ile
    435                 440                 445

Asn Thr Pro Lys Glu Ile Asp Asp Thr Val Thr Ser Asn Asn Asn Tyr
450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
            485                 490                 495

Tyr Ile Pro Lys Tyr Asp Ser Asn Gly Thr Ser Asp Ile Glu Gln His
        500                 505                 510

Asp Val Asn Glu Leu Asn Val Phe Phe Tyr Leu Asp Ala Gln Lys Val
    515                 520                 525

Pro Glu Gly Glu Asn Asn Val Asn Leu Thr Ser Ser Ile Asp Thr Ala
530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Ser Trp Ile
            565                 570                 575

Gln Gln Val Leu Val Asp Phe Thr Thr Glu Ala Asn Gln Lys Ser Thr
        580                 585                 590

Val Asp Lys Ile Ala Asp Ile Ser Ile Val Val Pro Tyr Ile Gly Leu
    595                 600                 605

Ala Leu Asn Ile Gly Asn Glu Ala Gln Lys Gly Asn Phe Lys Asp Ala
610                 615                 620

Leu Glu Leu Leu Gly Ala Gly Ile Leu Leu Glu Phe Glu Pro Glu Leu
625                 630                 635                 640
```

-continued

```
Leu Ile Pro Thr Ile Leu Val Phe Thr Ile Lys Ser Phe Leu Gly Ser
                645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
        675                 680                 685

Trp Met Thr Lys Ile Asn Thr Gln Phe Asn Lys Arg Lys Glu Gln Met
    690                 695                 700

Tyr Gln Ala Leu Gln Asn Gln Val Asn Ala Ile Lys Thr Ile Ile Glu
705                 710                 715                 720

Ser Lys Tyr Asn Ser Tyr Thr Leu Glu Glu Lys Asn Glu Leu Thr Asn
                725                 730                 735

Lys Tyr Asp Ile Lys Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
        755                 760                 765

Tyr Leu Met Lys Ile Ile Asn Glu Val Lys Ile Asn Lys Leu Arg Glu
    770                 775                 780

Tyr Asp Glu Asn Val Lys Thr Tyr Leu Leu Asn Tyr Ile Ile Gln His
785                 790                 795                 800

Gly Ser Ile Leu Gly Glu Ser Gln Gln Glu Leu Asn Ser Met Val Thr
                805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
        835                 840                 845

Ser Ser Ser Val Leu Asn Met Arg Tyr Lys Asn Asp Lys Tyr Val Asp
    850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
                885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
        915                 920                 925

Lys Ile Val Asn Val Asn Asn Glu Tyr Thr Ile Ile Asn Cys Met Arg
    930                 935                 940

Asp Asn Asn Ser Gly Trp Lys Val Ser Leu Asn His Asn Glu Ile Ile
945                 950                 955                 960

Trp Thr Phe Glu Asp Asn Arg Gly Ile Asn Gln Lys Leu Ala Phe Asn
                965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu  Gly Asp Ser Lys Leu  Tyr Ile Asn
        995                 1000                1005

Gly Asn Leu Ile Asp Gln Lys  Ser Ile Leu Asn Leu  Gly Asn Ile
    1010                1015                1020

His Val Ser Asp Asn Ile Leu  Phe Lys Ile Val Asn  Cys Ser Tyr
    1025                1030                1035

Thr Arg Tyr Ile Gly Ile Arg  Tyr Phe Asn Ile Phe  Asp Lys Glu
    1040                1045                1050

Leu Asp Glu Thr Glu Ile Gln  Thr Leu Tyr Ser Asn  Glu Pro Asn
```

-continued

| | | | | | | | | | |
|---|---|---|---|---|---|---|---|---|---|
| | | 1055 | | | 1060 | | | 1065 | |
| Thr | Asn | Ile | Leu | Lys | Asp | Phe | Trp | Gly | Asn | Tyr | Leu | Leu | Tyr | Asp |
| | 1070 | | | | 1075 | | | | 1080 | |

Thr Asn Ile Leu Lys Asp Phe Trp Gly Asn Tyr Leu Leu Tyr Asp
        1070                1075                1080

Lys Glu Tyr Tyr Leu Leu Asn Val Leu Lys Pro Asn Asn Phe Ile
        1085                1090                1095

Asp Arg Arg Lys Asp Ser Thr Leu Ser Ile Asn Asn Ile Arg Ser
        1100                1105                1110

Thr Ile Leu Leu Ala Asn Arg Leu Tyr Ser Gly Ile Lys Val Lys
        1115                1120                1125

Ile Gln Arg Val Asn Asn Ser Ser Thr Asn Asp Asn Leu Val Arg
        1130                1135                1140

Lys Asn Asp Gln Val Tyr Ile Asn Phe Val Ala Ser Lys Thr His
        1145                1150                1155

Leu Phe Pro Leu Tyr Ala Asp Thr Ala Thr Thr Asn Lys Glu Lys
        1160                1165                1170

Thr Ile Lys Ile Ser Ser Ser Gly Asn Arg Phe Asn Gln Val Val
        1175                1180                1185

Val Met Asn Ser Val Gly Asn Cys Thr Met Asn Phe Lys Asn Asn
        1190                1195                1200

Asn Gly Asn Asn Ile Gly Leu Leu Gly Phe Lys Ala Asp Thr Val
        1205                1210                1215

Val Ala Ser Thr Trp Tyr Tyr Thr His Met Arg Asp His Thr Asn
        1220                1225                1230

Ser Asn Gly Cys Phe Trp Asn Phe Ile Ser Glu Glu His Gly Trp
        1235                1240                1245

Gln Glu Lys
        1250

<210> SEQ ID NO 11
<211> LENGTH: 3843
<212> TYPE: DNA
<213> ORGANISM: Clostridium botulinum

<400> SEQUENCE: 11
atgccagttg taataaatag ttttaattat aatgaccctg ttaatgatga gacaatttta    60
tacatgcaga aaccatatga agaaagaagt agaaaatatt ataaagcttt tgagattatg   120
cctaatgttt ggataatgcc tgagagagat acaataggaa ctaagcctga tgagtttcag   180
gtgccggatt cattaagaa cggaagtagt gcttattatg atcctaatta tttaaccact   240
gatgctgaaa aagatagata tttaaaaaca atgataaaat tatttaatag aattaatagt   300
aatcctacag ggaaagtttt gttagaagaa gtatcaaatg ctagaccata tttaggagat   360
gatgacacgc taattaatga attccttcca gttaatgtaa ctacaagtgt aatataaaa    420 tttcaactg atgttgaaag ttcaataata tcgaatcttc ttgtattggg agcaggacct   480
gatatattta agcttactg taccccctt gtaaggttta ataagtcaga taaattaatt   540
gaaccaagta atcatggttt tggatcaatt aatatcttga cattttcacc tgagtatgaa   600
catattttta atgatattag tggagggaat cataatagta cagaatcatt tattgcagat   660
cctgcaattt cactagctca tgaattgata catgcactac atggattata cggggctaag   720
gcagttactc ataaagagtc tctagtagca gagcgaggac ctcttatgat agccgaaaag   780
cccataaggc tagaagaatt tttaactttt ggaggtgagg attaaatat cattcctagt   840 gctatgaagg aaaaaatata taacgatctt ttagctaact atgaaaaaat agctactaga   900

```
cttagagaag ttaatacggc tcctcctgga tatgatatta atgaatataa agattatttt    960
caatggaagt atggactaga tagaaatgca gatggaagtt atactgtgaa tagaaataaa   1020
tttaatgaaa tttataaaaa attatatagc tttacagaga ttgacttagc aaataaattt   1080
aaagtaaaat gtagaaatac ttattttatt aaatatggat ttgtaaaagt tccaaatttg   1140
ttagatgatg atatttatac tgtatcagag gggtttaata taggtaattt agcagtaaac   1200
aatcgcggac aaaatataaa tttaaatcct aaaattattg attccattcc agataaaggt   1260
ttagtggaaa agattattaa attttgtaag agcattattc ctagaaaagg tacgaagcag   1320
tcaccgtcac tatgcattag agtaaataat agggagttat tttttgtagc ttcagaaagt   1380
agctataatg aaagtgatat taatacacct aaagaaattg acgatacaac aaatctaaat   1440
aataattata gaataatttt agatgaagtt atttttagatt ataatagtga gacaatacct   1500
caaatatcaa atcgaacatt aaatacactt gtacaagaca atagttatgt gccaagatat   1560
gattctaatg gaacaagtga aatagaggaa tatgatgttg ttgactttaa tgtattttc    1620
tatttacatg cacaaaaagt accagaaggt gaaaccaata taagtttaac ttcttcaatt   1680
gatacagcat tattagaaga atccaaagta tatacatttt tttcttcaga gtttatcgat   1740
actatcaata aacctgtaaa tgcagcacta tttatagatt ggataagcaa agtaataaga   1800
gattttacca ctgaagctac acaaaaaagt actgttgata agattgcaga catatcttta   1860
attgtaccct atgtaggtct tgctttgaat atagttattg aggcagaaaa aggaaatttt   1920
gaggaggcat ttgaattatt aggagcgggt attttattag aatttgtgcc agagcttaca   1980
attcctgtaa ttttagtgtt tacgataaaa tcctatatag attcatatga gaataaaaat   2040
aaagcaatta aagcaataaa taattcatta atcgaaagag aagcaaagtg gaaagaaata   2100
tatagttgga tagtatcaaa ttggcttact agaattaata cgcaatttaa taaaagaaaa   2160
gagcaaatgt atcaggcttt acaaaatcaa gtagatgcaa taaaaacagc aatagaatat   2220
aaatataata attatacttc agatgagaaa aatagacttg aatctaaata taatatcaat   2280
aatatagaag aagaattgaa taaaaaagtt tctttagcaa tgaaaaatat agaaagattt   2340
atgcacagaaa gttctatatc ttattttaatg aaattaataa atgaagccga agttggtaaa   2400
ttaaaagaat atgataaaca tgttaagagc gatttattag actatattct ctaccataaa   2460
ttaatcttag gagagcagac aaaggaatta attgatttgg tgactagtac tttgaatagt   2520
agtattccat ttgaactttc ttcatatact aatgataaaa ttctaattat atattttaat   2580
agattatata aaaaaattaa agatagttct attttagata tgcgatatga aaataataaa   2640
tttatagata tctctggata tggttcaaat ataagcatta atggaaacgt atatatttat   2700
tcaacaaata gaaatcaatt tggaatatat agtggtaggc ttagtgaagt taatatagct   2760
caaaataatg atattatata caatagtaga tatcaaaatt ttagtattag tttctgggta   2820
accattccta aacactacag acctatgaat cgtaatcggg aatacactat aataaattgt   2880
atggggaata taattcggg atggaaaata tcacttagaa ctattagaga ttgtgaaata    2940
atttggactt tacaagatac ttccggaaat aaggaaaaat taatttttag gtatgaagaa   3000
cttgctagta tatctgatta tataaataaa tggattttttg taactattac taataataga   3060
ttaggcaatt ctagaattta catcaatgga aatttaatag ttgaaaaatc aatttcgaat   3120
ttaggtgata ttcatgttag tgataatata ttatttaaaa ttgttggttg tgatgatgaa   3180
acgtatgttg gtataagata tttttaaagtt tttaatacgg aattagataa aacagaaatt   3240
gagacttat atagtaatga gccagatcca agtatcttaa aagactattg gggaaattat   3300
```

-continued

```
ttgctatata ataaaaaata ttatttattc aatttactaa gaaaagataa gtatattact   3360
cggaattcag gcatttaaa tattaatcaa caaagaggtg ttactggagg catatctgtt   3420
tttttgaact ataaattata tgaaggagta gaagttatta taagaaaaaa tgctcctata   3480
gatatatcta atacagataa ttttgttaga aaaaacgatc tagcatacat taatgtagta   3540
gatcatggtg tagaatatcg gttatatgct gatatatcaa ttacaaaatc agagaaaata   3600
ataaaattaa taagaacatc taatccaaac gatagcttag gtcaaattat agttatggat   3660
tcaataggaa ataattgcac aatgaatttt caaaacaatg atgggagcaa tataggatta   3720
ctaggttttc attcagatga tttggttgct agtagttggt attataacca tatacgaaga   3780
aacactagca gtaatggatg cttttggagt tttatttcta aagagcatgg ttggaaagaa   3840
taa                                                                  3843
```

<210> SEQ ID NO 12
<211> LENGTH: 1280
<212> TYPE: PRT
<213> ORGANISM: Clostridium botulinum

<400> SEQUENCE: 12

```
Met Pro Val Val Ile Asn Ser Phe Asn Tyr Asn Asp Pro Val Asn Asp
1               5                   10                  15

Glu Thr Ile Leu Tyr Met Gln Lys Pro Tyr Glu Glu Arg Ser Arg Lys
            20                  25                  30

Tyr Tyr Lys Ala Phe Glu Ile Met Pro Asn Val Trp Ile Met Pro Glu
        35                  40                  45

Arg Asp Thr Ile Gly Thr Lys Pro Asp Glu Phe Gln Val Pro Asp Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Met Ile Lys Leu Phe Asn
                85                  90                  95

Arg Ile Asn Ser Asn Pro Thr Gly Lys Val Leu Leu Glu Glu Val Ser
            100                 105                 110

Asn Ala Arg Pro Tyr Leu Gly Asp Asp Thr Leu Ile Asn Glu Phe
        115                 120                 125

Leu Pro Val Asn Val Thr Thr Ser Val Asn Ile Lys Phe Ser Thr Asp
    130                 135                 140

Val Glu Ser Ser Ile Ile Ser Asn Leu Leu Val Leu Gly Ala Gly Pro
145                 150                 155                 160

Asp Ile Phe Lys Ala Tyr Cys Thr Pro Leu Val Arg Phe Asn Lys Ser
                165                 170                 175

Asp Lys Leu Ile Glu Pro Ser Asn His Gly Phe Gly Ser Ile Asn Ile
            180                 185                 190

Leu Thr Phe Ser Pro Glu Tyr Glu His Ile Phe Asn Asp Ile Ser Gly
        195                 200                 205

Gly Asn His Asn Ser Thr Glu Ser Phe Ile Ala Asp Pro Ala Ile Ser
    210                 215                 220

Leu Ala His Glu Leu Ile His Ala Leu His Gly Leu Tyr Gly Ala Lys
225                 230                 235                 240

Ala Val Thr His Lys Glu Ser Leu Val Ala Glu Arg Gly Pro Leu Met
                245                 250                 255

Ile Ala Glu Lys Pro Ile Arg Leu Glu Glu Phe Leu Thr Phe Gly Gly
            260                 265                 270
```

```
Glu Asp Leu Asn Ile Ile Pro Ser Ala Met Lys Glu Lys Ile Tyr Asn
        275                 280                 285

Asp Leu Leu Ala Asn Tyr Glu Lys Ile Ala Thr Arg Leu Arg Glu Val
    290                 295                 300

Asn Thr Ala Pro Pro Gly Tyr Asp Ile Asn Glu Tyr Lys Asp Tyr Phe
305                 310                 315                 320

Gln Trp Lys Tyr Gly Leu Asp Arg Asn Ala Asp Gly Ser Tyr Thr Val
                325                 330                 335

Asn Arg Asn Lys Phe Asn Glu Ile Tyr Lys Lys Leu Tyr Ser Phe Thr
            340                 345                 350

Glu Ile Asp Leu Ala Asn Lys Phe Lys Val Lys Cys Arg Asn Thr Tyr
        355                 360                 365

Phe Ile Lys Tyr Gly Phe Val Lys Val Pro Asn Leu Leu Asp Asp Asp
    370                 375                 380

Ile Tyr Thr Val Ser Glu Gly Phe Asn Ile Gly Asn Leu Ala Val Asn
385                 390                 395                 400

Asn Arg Gly Gln Asn Ile Asn Leu Asn Pro Lys Ile Ile Asp Ser Ile
                405                 410                 415

Pro Asp Lys Gly Leu Val Glu Lys Ile Ile Lys Phe Cys Lys Ser Ile
            420                 425                 430

Ile Pro Arg Lys Gly Thr Lys Gln Ser Pro Ser Leu Cys Ile Arg Val
        435                 440                 445

Asn Asn Arg Glu Leu Phe Phe Val Ala Ser Glu Ser Ser Tyr Asn Glu
    450                 455                 460

Ser Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Glu Thr Ile Pro Gln Ile Ser Asn Arg Thr Leu Asn Thr Leu Val Gln
            500                 505                 510

Asp Asn Ser Tyr Val Pro Arg Tyr Asp Ser Asn Gly Thr Ser Glu Ile
        515                 520                 525

Glu Glu Tyr Asp Val Val Asp Phe Asn Val Phe Phe Tyr Leu His Ala
    530                 535                 540

Gln Lys Val Pro Glu Gly Glu Thr Asn Ile Ser Leu Thr Ser Ser Ile
545                 550                 555                 560

Asp Thr Ala Leu Leu Glu Glu Ser Lys Val Tyr Thr Phe Phe Ser Ser
                565                 570                 575

Glu Phe Ile Asp Thr Ile Asn Lys Pro Val Asn Ala Ala Leu Phe Ile
            580                 585                 590

Asp Trp Ile Ser Lys Val Ile Arg Asp Phe Thr Thr Glu Ala Thr Gln
        595                 600                 605

Lys Ser Thr Val Asp Lys Ile Ala Asp Ile Ser Leu Ile Val Pro Tyr
    610                 615                 620

Val Gly Leu Ala Leu Asn Ile Val Ile Glu Ala Glu Lys Gly Asn Phe
625                 630                 635                 640

Glu Glu Ala Phe Glu Leu Leu Gly Ala Gly Ile Leu Leu Glu Phe Val
                645                 650                 655

Pro Glu Leu Thr Ile Pro Val Ile Leu Val Phe Thr Ile Lys Ser Tyr
            660                 665                 670

Ile Asp Ser Tyr Glu Asn Lys Asn Lys Ala Ile Lys Ala Ile Asn Asn
        675                 680                 685
```

```
Ser Leu Ile Glu Arg Glu Ala Lys Trp Lys Glu Ile Tyr Ser Trp Ile
690                 695                 700

Val Ser Asn Trp Leu Thr Arg Ile Asn Thr Gln Phe Asn Lys Arg Lys
705                 710                 715                 720

Glu Gln Met Tyr Gln Ala Leu Gln Asn Gln Val Asp Ala Ile Lys Thr
            725                 730                 735

Ala Ile Glu Tyr Lys Tyr Asn Asn Tyr Thr Ser Asp Glu Lys Asn Arg
        740                 745                 750

Leu Glu Ser Lys Tyr Asn Ile Asn Ile Glu Glu Leu Asn Lys
        755                 760                 765

Lys Val Ser Leu Ala Met Lys Asn Ile Glu Arg Phe Met Thr Glu Ser
770                 775                 780

Ser Ile Ser Tyr Leu Met Lys Leu Ile Asn Glu Ala Glu Val Gly Lys
785                 790                 795                 800

Leu Lys Glu Tyr Asp Lys His Val Lys Ser Asp Leu Leu Asp Tyr Ile
            805                 810                 815

Leu Tyr His Lys Leu Ile Leu Gly Glu Gln Thr Lys Glu Leu Ile Asp
        820                 825                 830

Leu Val Thr Ser Thr Leu Asn Ser Ser Ile Pro Phe Glu Leu Ser Ser
        835                 840                 845

Tyr Thr Asn Asp Lys Ile Leu Ile Tyr Phe Asn Arg Leu Tyr Lys
850                 855                 860

Lys Ile Lys Asp Ser Ser Ile Leu Asp Met Arg Tyr Glu Asn Asn Lys
865                 870                 875                 880

Phe Ile Asp Ile Ser Gly Tyr Gly Ser Asn Ile Ser Ile Asn Gly Asn
            885                 890                 895

Val Tyr Ile Tyr Ser Thr Asn Arg Asn Gln Phe Gly Ile Tyr Ser Gly
        900                 905                 910

Arg Leu Ser Glu Val Asn Ile Ala Gln Asn Asn Asp Ile Ile Tyr Asn
        915                 920                 925

Ser Arg Tyr Gln Asn Phe Ser Ile Ser Phe Trp Val Thr Ile Pro Lys
930                 935                 940

His Tyr Arg Pro Met Asn Arg Asn Arg Glu Tyr Thr Ile Ile Asn Cys
945                 950                 955                 960

Met Gly Asn Asn Asn Ser Gly Trp Lys Ile Ser Leu Arg Thr Ile Arg
            965                 970                 975

Asp Cys Glu Ile Ile Trp Thr Leu Gln Asp Thr Ser Gly Asn Lys Glu
        980                 985                 990

Lys Leu Ile Phe Arg Tyr Glu Glu Leu Ala Ser Ile Ser Asp Tyr Ile
        995                 1000                1005

Asn Lys Trp Ile Phe Val Thr Ile Thr Asn Asn Arg Leu Gly Asn
    1010                1015                1020

Ser Arg Ile Tyr Ile Asn Gly Asn Leu Ile Val Glu Lys Ser Ile
    1025                1030                1035

Ser Asn Leu Gly Asp Ile His Val Ser Asp Asn Ile Leu Phe Lys
    1040                1045                1050

Ile Val Gly Cys Asp Asp Glu Thr Tyr Val Gly Ile Arg Tyr Phe
    1055                1060                1065

Lys Val Phe Asn Thr Glu Leu Asp Lys Thr Glu Ile Glu Thr Leu
    1070                1075                1080

Tyr Ser Asn Glu Pro Asp Pro Ser Ile Leu Lys Asp Tyr Trp Gly
    1085                1090                1095

Asn Tyr Leu Leu Tyr Asn Lys Lys Tyr Tyr Leu Phe Asn Leu Leu
```

-continued

```
                        1100              1105                1110
Arg  Lys  Asp  Lys  Tyr  Ile  Thr  Arg  Asn  Ser  Gly  Ile  Leu  Asn  Ile
         1115                     1120                     1125

Asn  Gln  Gln  Arg  Gly  Val  Thr  Gly  Gly  Ile  Ser  Val  Phe  Leu  Asn
         1130                     1135                     1140

Tyr  Lys  Leu  Tyr  Glu  Gly  Val  Glu  Val  Ile  Ile  Arg  Lys  Asn  Ala
         1145                     1150                     1155

Pro  Ile  Asp  Ile  Ser  Asn  Thr  Asp  Asn  Phe  Val  Arg  Lys  Asn  Asp
         1160                     1165                     1170

Leu  Ala  Tyr  Ile  Asn  Val  Val  Asp  His  Gly  Val  Glu  Tyr  Arg  Leu
         1175                     1180                     1185

Tyr  Ala  Asp  Ile  Ser  Ile  Thr  Lys  Ser  Glu  Lys  Ile  Ile  Lys  Leu
         1190                     1195                     1200

Ile  Arg  Thr  Ser  Asn  Pro  Asn  Asp  Ser  Leu  Gly  Gln  Ile  Ile  Val
         1205                     1210                     1215

Met  Asp  Ser  Ile  Gly  Asn  Asn  Cys  Thr  Met  Asn  Phe  Gln  Asn  Asn
         1220                     1225                     1230

Asp  Gly  Ser  Asn  Ile  Gly  Leu  Leu  Gly  Phe  His  Ser  Asp  Asp  Leu
         1235                     1240                     1245

Val  Ala  Ser  Ser  Trp  Tyr  Tyr  Asn  His  Ile  Arg  Arg  Asn  Thr  Ser
         1250                     1255                     1260

Ser  Asn  Gly  Cys  Phe  Trp  Ser  Phe  Ile  Ser  Lys  Glu  His  Gly  Trp
         1265                     1270                     1275

Lys  Glu
     1280
```

<210> SEQ ID NO 13
<211> LENGTH: 3894
<212> TYPE: DNA
<213> ORGANISM: Clostridium botulinum
<220> FEATURE:
<221> NAME/KEY: misc_feature
<222> LOCATION: (20)..(20)
<223> OTHER INFORMATION: n is a, c, g, or t

<400> SEQUENCE: 13

```
atgccagtta atataaaaan ctttaattat aatgacccta ttaataatga tgacattatt      60
atgatggaac cattcaatga cccagggcca ggaacatatt ataaagcttt taggattata     120
gatcgtattt ggatagtacc agaaaggttt acttatggat tcaacctga ccaatttaat      180 gccagtacag gagttttag taaagatgtc tacgaatatt acgatccaac ttatttaaaa      240
accgatgctg aaaaagataa attttttaaaa acaatgatta aattatttaa tagaattaat    300
tcaaaaccat caggacagag attactggat atgatagtag atgctatacc ttatcttgga    360
aatgcatcta caccgcccga caatttgca gcaaatgttg caaatgtatc tattaataaa     420
aaaattatcc aacctggagc tgaagatcaa ataaaaggtt aatgacaaa tttaataata    480 tttggaccag gaccagttct aagtgataat tttactgata gtatgattat gaatggccat    540
tccccaatat cagaaggatt tggtgcaaga atgatgataa gattttgtcc tagttgttta   600
aatgtattta ataatgttca ggaaaataaa gatacatcta tattagtag acgcgcgtat     660 tttgcagatc cagctctaac gttaatgcat gaacttatac atgtgttaca tggattatat    720
ggaattaaga taagtaattt accaattact ccaaatacaa agaattttt catgcaacat    780 agcgatcctg tacaagcaga gaactatat acattcggag acatgatcc tagtgtata     840 agtccttcta cggatatgaa atatttaat aaagcgttac aaaatttca agatatagct     900
```

```
aataggctta atattgtttc aagtgcccaa gggagtggaa ttgatatttc cttatataaa     960
caaatatata aaaataaata tgattttgtt gaagatccta atggaaaata tagtgtagat    1020
aaggataagt ttgataaatt atataaggcc ttaatgtttg gctttactga aactaatcta    1080
gctggtgaat atggaataaa aactaggtat tcttatttta gtgaatattt gccaccgata    1140
aaaactgaaa aattgttaga caatacaatt tatactcaaa atgaaggctt taacatagct    1200
agtaaaaatc tcaaaacgga atttaatggt cagaataagg cggtaaataa agaggcttat    1260
gaagaaatca gcctagaaca tctcgttata tatagaatag caatgtgcaa gcctgtaatg    1320
tacaaaaata ccgtaaatc tgaacagtgt attattgtta ataatgagga tttattttc    1380 atagctaata aagatagttt ttcaaaagat ttagctaaag cagaaactat agcatataat    1440
acacaaaata atactataga aaataatttt tctatagatc agttgatttt agataatgat    1500
ttaagcagtg gcatagactt accaaatgaa aacacagaac catttacaaa ttttgacgac    1560
atagatatcc ctgtgtatat taaacaatct gctttaaaaa aaattttgt ggatggagat    1620 agccttttg aatatttaca tgctcaaaca tttccttcta atatagaaaa tctacaacta    1680
acgaattcat taaatgatgc tttaagaaat aataataaag tctatacttt tttttctaca    1740
aaccttgttg aaaaagctaa tacagttgta ggtgcttcac tttttgtaaa ctgggtaaaa    1800
ggagtaatag atgattttac atctgaatcc acacaaaaaa gtactataga taaagtttca    1860
gatgtatcca taattattcc ctatatagga cctgctttga atgtaggaaa tgaaacagct    1920
aaagaaaatt ttaaaaatgc ttttgaaata ggtggagccg ctatcttaat ggagtttatt    1980
ccagaactta ttgtacctat agttggattt tttacattag aatcatatgt aggaaataaa    2040
gggcatatta ttatgacgat atccaatgct ttaaagaaaa gggatcaaaa atggacagat    2100
atgtatggtt tgatagtatc gcagtggctc tcaacggtta atactcaatt ttatacaata    2160
aaagaaagaa tgtacaatgc tttaaataat caatcacaag caatagaaaa aataatagaa    2220
gatcaatata atagatatag tgaagaagat aaaatgaata ttaacattga ttttaatgat    2280
atagatttta aacttaatca aagtataaat ttagcaataa acaatataga tgatttata    2340 aaccaatgtt ctatatcata tctaatgaat agaatgattc cattagctgt aaaaaagtta    2400
aaagactttg atgataatct taagagagat ttattggagt atatagatac aaatgaacta    2460
tatttacttg atgaagtaaa tattctaaaa tcaaaagtaa atagacacct aaaagacagt    2520
ataccatttg atctttcact atataccaag gacacaattt taatacaagt ttttaataat    2580
tatattagta atattagtag taatgctatt ttaagtttaa gttatagagg tgggcgttta    2640
atagattcat ctggatatgg tgcaactatg aatgtaggtt cagatgttat ctttaatgat    2700
ataggaaatg gtcaatttaa attaaataat tctgaaaata gtaatattac ggcacatcaa    2760
agtaaattcg ttgtatatga tagtatgttt gataatttta gcattaactt ttgggtaagg    2820
actcctaaat ataataataa tgatatacaa acttatcttc aaaatgagta tacaataatt    2880
agttgtataa aaaatgactc aggatggaaa gtatctatta agggaaatag aataatatgg    2940
acattaatag atgttaatgc aaaatctaaa tcaatatttt tcgaatatag tataaaagat    3000
aatatatcag attatataaa taaatggttt tccataacta ttactaatga tagattaggt    3060
aacgcaaata tttatataaa tggaagtttg aaaaaaagtg aaaaaatttt aaacttagat    3120
agaattaatt ctagtaatga tatagacttc aaattaatta attgtacaga tactactaaa    3180
tttgtttgga ttaaggattt taatattttt ggtagagaat taaatgctac agaagtatct    3240
```

-continued

```
tcactatatt ggattcaatc atctacaaat actttaaaag attttggggg gaatcccttta   3300 agatacgata cacaaatacta tctgtttaat caaggtatgc aaaatatcta tataaagtat   3360
tttagtaaag cttctatggg ggaaactgca ccacgtacaa actttaataa tgcagcaata   3420
aattatcaaa atttatatct tggtttacga tttattataa aaaaagcatc aaattctcgg   3480
aatataaata atgataatat agtcagagaa ggagattata tatatcttaa tattgataat   3540
atttctgatg aatcttacag agtatatgtt ttggtgaatt ctaaagaaat tcaaactcaa   3600
ttatttttag cacccataaa tgatgatcct acgttctatg atgtactaca aataaaaaaa   3660
tattatgaaa aaacaacata taattgtcag atactttgcg aaaaagatac taaaacattt   3720
gggctgtttg gaattggtaa atttgttaaa gattatggat atgtttggga tacctatgat   3780
aattattttt gcataagtca gtggtatctc agaagaatat ctgaaaatat aaataaatta   3840
aggttgggat gtaattggca attcattccc gtggatgaag gatggacaga ataa         3894
```

<210> SEQ ID NO 14
<211> LENGTH: 1297
<212> TYPE: PRT
<213> ORGANISM: Clostridium botulinum
<220> FEATURE:
<221> NAME/KEY: misc_feature
<222> LOCATION: (7)..(7)
<223> OTHER INFORMATION: Xaa can be any naturally occurring amino acid

<400> SEQUENCE: 14

```
Met Pro Val Asn Ile Lys Xaa Phe Asn Tyr Asn Asp Pro Ile Asn Asn
1               5                   10                  15

Asp Asp Ile Ile Met Met Glu Pro Phe Asn Asp Pro Gly Pro Gly Thr
            20                  25                  30

Tyr Tyr Lys Ala Phe Arg Ile Ile Asp Arg Ile Trp Ile Val Pro Glu
        35                  40                  45

Arg Phe Thr Tyr Gly Phe Gln Pro Asp Gln Phe Asn Ala Ser Thr Gly
    50                  55                  60

Val Phe Ser Lys Asp Val Tyr Glu Tyr Tyr Asp Pro Thr Tyr Leu Lys
65                  70                  75                  80

Thr Asp Ala Glu Lys Asp Lys Phe Leu Lys Thr Met Ile Lys Leu Phe
                85                  90                  95

Asn Arg Ile Asn Ser Lys Pro Ser Gly Gln Arg Leu Leu Asp Met Ile
            100                 105                 110

Val Asp Ala Ile Pro Tyr Leu Gly Asn Ala Ser Thr Pro Pro Asp Lys
        115                 120                 125

Phe Ala Ala Asn Val Ala Asn Val Ser Ile Asn Lys Lys Ile Ile Gln
    130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
            180                 185                 190

Ile Arg Phe Cys Pro Ser Cys Leu Asn Val Phe Asn Asn Val Gln Glu
        195                 200                 205

Asn Lys Asp Thr Ser Ile Phe Ser Arg Arg Ala Tyr Phe Ala Asp Pro
    210                 215                 220

Ala Leu Thr Leu Met His Glu Leu Ile His Val Leu His Gly Leu Tyr
225                 230                 235                 240
```

-continued

```
Gly Ile Lys Ile Ser Asn Leu Pro Ile Thr Pro Asn Thr Lys Glu Phe
                245                 250                 255
Phe Met Gln His Ser Asp Pro Val Gln Ala Glu Glu Leu Tyr Thr Phe
            260                 265                 270
Gly Gly His Asp Pro Ser Val Ile Ser Pro Ser Thr Asp Met Asn Ile
        275                 280                 285
Tyr Asn Lys Ala Leu Gln Asn Phe Gln Asp Ile Ala Asn Arg Leu Asn
    290                 295                 300
Ile Val Ser Ser Ala Gln Gly Ser Gly Ile Asp Ile Ser Leu Tyr Lys
305                 310                 315                 320
Gln Ile Tyr Lys Asn Lys Tyr Asp Phe Val Glu Asp Pro Asn Gly Lys
                325                 330                 335
Tyr Ser Val Asp Lys Asp Lys Phe Asp Lys Leu Tyr Lys Ala Leu Met
            340                 345                 350
Phe Gly Phe Thr Glu Thr Asn Leu Ala Gly Glu Tyr Gly Ile Lys Thr
        355                 360                 365
Arg Tyr Ser Tyr Phe Ser Glu Tyr Leu Pro Pro Ile Lys Thr Glu Lys
    370                 375                 380
Leu Leu Asp Asn Thr Ile Tyr Thr Gln Asn Glu Gly Phe Asn Ile Ala
385                 390                 395                 400
Ser Lys Asn Leu Lys Thr Glu Phe Asn Gly Gln Asn Lys Ala Val Asn
                405                 410                 415
Lys Glu Ala Tyr Glu Glu Ile Ser Leu Glu His Leu Val Ile Tyr Arg
            420                 425                 430
Ile Ala Met Cys Lys Pro Val Met Tyr Lys Asn Thr Gly Lys Ser Glu
        435                 440                 445
Gln Cys Ile Ile Val Asn Asn Glu Asp Leu Phe Phe Ile Ala Asn Lys
    450                 455                 460
Asp Ser Phe Ser Lys Asp Leu Ala Lys Ala Glu Thr Ile Ala Tyr Asn
465                 470                 475                 480
Thr Gln Asn Asn Thr Ile Glu Asn Asn Phe Ser Ile Asp Gln Leu Ile
                485                 490                 495
Leu Asp Asn Asp Leu Ser Ser Gly Ile Asp Leu Pro Asn Glu Asn Thr
            500                 505                 510
Glu Pro Phe Thr Asn Phe Asp Asp Ile Asp Ile Pro Val Tyr Ile Lys
        515                 520                 525
Gln Ser Ala Leu Lys Lys Ile Phe Val Asp Gly Asp Ser Leu Phe Glu
    530                 535                 540
Tyr Leu His Ala Gln Thr Phe Pro Ser Asn Ile Glu Asn Leu Gln Leu
545                 550                 555                 560
Thr Asn Ser Leu Asn Asp Ala Leu Arg Asn Asn Asn Lys Val Tyr Thr
                565                 570                 575
Phe Phe Ser Thr Asn Leu Val Glu Lys Ala Asn Thr Val Val Gly Ala
            580                 585                 590
Ser Leu Phe Val Asn Trp Val Lys Gly Val Ile Asp Asp Phe Thr Ser
        595                 600                 605
Glu Ser Thr Gln Lys Ser Thr Ile Asp Lys Val Ser Asp Val Ser Ile
    610                 615                 620
Ile Ile Pro Tyr Ile Gly Pro Ala Leu Asn Val Gly Asn Glu Thr Ala
625                 630                 635                 640
Lys Glu Asn Phe Lys Asn Ala Phe Glu Ile Gly Gly Ala Ala Ile Leu
                645                 650                 655
Met Glu Phe Ile Pro Glu Leu Ile Val Pro Ile Val Gly Phe Phe Thr
```

-continued

```
              660              665              670
Leu Glu Ser Tyr Val Gly Asn Lys Gly His Ile Ile Met Thr Ile Ser
            675              680              685

Asn Ala Leu Lys Lys Arg Asp Gln Lys Trp Thr Asp Met Tyr Gly Leu
            690              695              700

Ile Val Ser Gln Trp Leu Ser Thr Val Asn Thr Gln Phe Tyr Thr Ile
705              710              715              720

Lys Glu Arg Met Tyr Asn Ala Leu Asn Asn Gln Ser Gln Ala Ile Glu
            725              730              735

Lys Ile Ile Glu Asp Gln Tyr Asn Arg Tyr Ser Glu Glu Asp Lys Met
            740              745              750

Asn Ile Asn Ile Asp Phe Asn Asp Ile Asp Phe Lys Leu Asn Gln Ser
            755              760              765

Ile Asn Leu Ala Ile Asn Asn Ile Asp Asp Phe Ile Asn Gln Cys Ser
            770              775              780

Ile Ser Tyr Leu Met Asn Arg Met Ile Pro Leu Ala Val Lys Lys Leu
785              790              795              800

Lys Asp Phe Asp Asp Asn Leu Lys Arg Asp Leu Leu Glu Tyr Ile Asp
            805              810              815

Thr Asn Glu Leu Tyr Leu Leu Asp Glu Val Asn Ile Leu Lys Ser Lys
            820              825              830

Val Asn Arg His Leu Lys Asp Ser Ile Pro Phe Asp Leu Ser Leu Tyr
            835              840              845

Thr Lys Asp Thr Ile Leu Ile Gln Val Phe Asn Asn Tyr Ile Ser Asn
            850              855              860

Ile Ser Ser Asn Ala Ile Leu Ser Leu Ser Tyr Arg Gly Gly Arg Leu
865              870              875              880

Ile Asp Ser Ser Gly Tyr Gly Ala Thr Met Asn Val Gly Ser Asp Val
            885              890              895

Ile Phe Asn Asp Ile Gly Asn Gly Gln Phe Lys Leu Asn Asn Ser Glu
            900              905              910

Asn Ser Asn Ile Thr Ala His Gln Ser Lys Phe Val Val Tyr Asp Ser
            915              920              925

Met Phe Asp Asn Phe Ser Ile Asn Phe Trp Val Arg Thr Pro Lys Tyr
            930              935              940

Asn Asn Asn Asp Ile Gln Thr Tyr Leu Gln Asn Glu Tyr Thr Ile Ile
945              950              955              960

Ser Cys Ile Lys Asn Asp Ser Gly Trp Lys Val Ser Ile Lys Gly Asn
            965              970              975

Arg Ile Ile Trp Thr Leu Ile Asp Val Asn Ala Lys Ser Lys Ser Ile
            980              985              990

Phe Phe Glu Tyr Ser Ile Lys Asp Asn Ile Ser Asp Tyr Ile Asn Lys
            995              1000             1005

Trp Phe Ser Ile Thr Ile Thr Asn Asp Arg Leu Gly Asn Ala Asn
            1010             1015             1020

Ile Tyr Ile Asn Gly Ser Leu Lys Lys Ser Glu Lys Ile Leu Asn
            1025             1030             1035

Leu Asp Arg Ile Asn Ser Ser Asn Asp Ile Asp Phe Lys Leu Ile
            1040             1045             1050

Asn Cys Thr Asp Thr Thr Lys Phe Val Trp Ile Lys Asp Phe Asn
            1055             1060             1065

Ile Phe Gly Arg Glu Leu Asn Ala Thr Glu Val Ser Ser Leu Tyr
            1070             1075             1080
```

| Trp | Ile | Gln | Ser | Ser | Thr | Asn | Thr | Leu | Lys | Asp | Phe | Trp | Gly | Asn |
|-----|-----|-----|-----|-----|-----|-----|-----|-----|-----|-----|-----|-----|-----|-----|
| 1085 | | | | | 1090 | | | | | 1095 | | | | |

Pro Leu Arg Tyr Asp Thr Gln Tyr Tyr Leu Phe Asn Gln Gly Met
    1100                1105                1110

Gln Asn Ile Tyr Ile Lys Tyr Phe Ser Lys Ala Ser Met Gly Glu
    1115                1120                1125

Thr Ala Pro Arg Thr Asn Phe Asn Asn Ala Ala Ile Asn Tyr Gln
    1130                1135                1140

Asn Leu Tyr Leu Gly Leu Arg Phe Ile Ile Lys Lys Ala Ser Asn
    1145                1150                1155

Ser Arg Asn Ile Asn Asn Asp Asn Ile Val Arg Glu Gly Asp Tyr
    1160                1165                1170

Ile Tyr Leu Asn Ile Asp Asn Ile Ser Asp Glu Ser Tyr Arg Val
    1175                1180                1185

Tyr Val Leu Val Asn Ser Lys Glu Ile Gln Thr Gln Leu Phe Leu
    1190                1195                1200

Ala Pro Ile Asn Asp Asp Pro Thr Phe Tyr Asp Val Leu Gln Ile
    1205                1210                1215

Lys Lys Tyr Tyr Glu Lys Thr Thr Tyr Asn Cys Gln Ile Leu Cys
    1220                1225                1230

Glu Lys Asp Thr Lys Thr Phe Gly Leu Phe Gly Ile Gly Lys Phe
    1235                1240                1245

Val Lys Asp Tyr Gly Tyr Val Trp Asp Thr Tyr Asp Asn Tyr Phe
    1250                1255                1260

Cys Ile Ser Gln Trp Tyr Leu Arg Arg Ile Ser Glu Asn Ile Asn
    1265                1270                1275

Lys Leu Arg Leu Gly Cys Asn Trp Gln Phe Ile Pro Val Asp Glu
    1280                1285                1290

Gly Trp Thr Glu
    1295

<210> SEQ ID NO 15
<211> LENGTH: 4400
<212> TYPE: DNA
<213> ORGANISM: Clostridium tetani

<400> SEQUENCE: 15
tagcattaaa aaaattagaa cctatagtaa ataaattaat taatatatag tttttataat     60
ttaattatga ataatattct taagataaaa agtaaatttt taaaaattta aatttcagt    120 ttacaaaaaa taacctgatt atgttatatg taattgtaaa aaacatataa aaaatcagaa    180
aaatttagga ggtatattat taatggatta ataataatt ttttaattta cttttgatta    240
ataaatatta aatgtttatt ttaattagga gatgatacgt atgccaataa ccataaataa    300
ttttagatat agtgatcctg ttaataatga tacaattatt atgatggagc caccatactg    360
taagggtcta gatatctatt ataaggcttt caaaataaca gatcgtattt ggatagtgcc    420
ggaaaggtat gaatttggga caaaacctga agattttaac ccaccatctt cattaataga    480
aggtgcatct gagtattacg atccaaatta tttaaggact gattctgata agatagatt    540 tttacaaacc atggtaaaac tgtttaacag aattaaaaac aatgtagcag gtgaagcctt    600
attagataag ataataaatg ccatacctta ccttggaaat tcatattcct tactagacaa    660
gtttgataca aactctaatt cagtatcttt taatttatta gaacaagacc ccagtggagc    720
aactacaaaa tcagcaatgc tgacaaattt aataatattt ggacctgggc ctgttttaaa    780

| | |
|---|---|
| taaaaatgag gttagaggta ttgtattgag ggtagataat aaaaattact tcccatgtag | 840 |
| agatggtttt ggctcaataa tgcaaatggc attttgccca gaatatgtac ctacctttga | 900 |
| taatgtaata gaaaatatta cgtcactcac tattggcaaa agcaaatatt ttcaagatcc | 960 |
| agcattacta ttaatgcacg aacttataca tgtactacat ggtttatacg gaatgcaggt | 1020 |
| atcaagccat gaaattattc catccaaaca agaaatttat atgcagcata catatccaat | 1080 |
| aagtgctgaa gaactattca cttttggcgg acaggatgct aatcttataa gtattgatat | 1140 |
| aaaaaacgat ttatatgaaa aaactttaaa tgattataaa gctatagcta acaaacttag | 1200 |
| tcaagtcact agctgcaatg atcccaacat tgatattgat agctacaaac aaatatatca | 1260 |
| acaaaaatat caattcgata agatagcaa tggacaatat attgtaaatg aggataaatt | 1320 |
| tcagatacta tataatagca taatgtatgg ttttacagag attgaattgg gaaaaaaatt | 1380 |
| taatataaaa actagacttt cttatttag tatgaatcat gaccctgtaa aaattccaaa | 1440 |
| tttattagat gatacaattt acaatgatac agaaggattt aatatagaaa gcaaagatct | 1500 |
| gaaatctgaa tataaaggac aaaatatgag ggtaaataca aatgctttta gaaatgttga | 1560 |
| tggatcaggc ctagtttcaa aacttattgg cttatgtaaa aaaattatac caccaacaaa | 1620 |
| tataagagaa aatttatata atagaactgc atcattaaca gatttaggag gagaattatg | 1680 |
| tataaaaatt aaaaatgaag atttaacttt tatagctgaa aaaaatagct ttcagaagaa | 1740 |
| accatttcaa gatgaaatag ttagttataa tacaaaaaat aaaccattaa atttaattaa | 1800 |
| ttcgctagat aaaattattg tagattataa tctacaaagt aaaattacat tacctaatga | 1860 |
| taggacaacc ccagttacaa aaggaattcc atatgctcca gaatataaaa gtaatgctgc | 1920 |
| aagtacaata gaaatacata atattgatga caatacaata tatcaatatt tgtatgctca | 1980 |
| aaaatctcct acaactctac aaagaataac tatgactaat tctgttgatg acgcattaat | 2040 |
| aaattccacc aaaatatatt catattttcc atctgtaatc agtaaagtta accaaggtgc | 2100 |
| acaaggaatt ttattcttac agtgggtgag agatataatt gatgattta ccaatgaatc | 2160 |
| ttcacaaaaa actactattg ataaaatttc agatgtatcc actattgttc cttatatagg | 2220 |
| acccgcatta acattgtaa aacaaggcta tgagggaaac tttataggcg ctttagaaac | 2280 |
| taccggagtg gtttattat tagaatatat tccagaaatt actttaccag taattgcagc | 2340 |
| tttatctata gcagaaagta gcacacaaaa agaaaagata ataaaaacaa tagataactt | 2400 |
| tttagaaaaa agatatgaaa aatggattga agtatataaa ctagtaaaag caaaatggtt | 2460 |
| aggcacagtt aatacgcaat tccaaaaaag aagttatcaa atgtatagat ctttagaata | 2520 |
| tcaagtagat gcaataaaaa aaataataga ctatgaatat aaaatatatt caggacctga | 2580 |
| taaggaacaa attgccgacg aaattaataa tctgaaaaac aaacttgaag aaaaggctaa | 2640 |
| taaagcaatg ataaacataa atatatttat gagggaaagt tctagatcat ttttagttaa | 2700 |
| tcaaatgatt aacgaagcta aaaagcagtt attagagttt gatactcaaa gcaaaaatat | 2760 |
| tttaatgcag tatataaaag caaattctaa atttataggt ataactgaac taaaaaaatt | 2820 |
| agaatcaaaa ataaacaaag ttttttcaac accaattcca ttttcttatt ctaaaaatct | 2880 |
| ggattgttgg gttgataatg aagaagatat agatgttata ttaaaaaaga gtacaatttt | 2940 |
| aaatttagat attaataatg atattatatc agatatatct gggtttaatt catctgtaat | 3000 |
| aacatatcca gatgctcaat tggtgcccgg aataaatggc aaagcaatac atttagtaaa | 3060 |
| caatgaatct tctgaagtta tagtgcataa agctatggat attgaatata atgatatgtt | 3120 |

```
taataatttt  accgttagct  tttggttgag  ggttcctaaa  gtatctgcta  gtcatttaga  3180
acaatatggc  acaaatgagt  attcaataat  tagctctatg  aaaaaacata  gtctatcaat  3240
aggatctggt  tggagtgtat  cacttaaagg  taataactta  atatggactt  taaaagattc  3300
cgcgggagaa  gttagacaaa  taacttttag  ggatttacct  gataaattta  atgcttattt  3360
agcaaataaa  tgggttttta  taactattac  taatgataga  ttatcttctg  cтaaттттgтa 3420

tataaatgga  gtacttatgg  gaagtgcaga  aattactggt  ttaggagcta  ttagagagga  3480

taataatata  acattaaaac  tagatagatg  taataataat  aatcaatacg  tttctattga  3540

taaatttagg  atattttgca  aagcattaaa  tccaaaagag  attgaaaaat  tatacacaag  3600

ттаттташ   aтaaccттттт  тaagagacтт  ctggggaaac  cctttacgat  atgatacaga  3660 atattatta  ataccagtag  cttctagttc  taaagatgtt  cattgaaaaa atataacaga 3720

ttatatgtat  ttgacaaatg  cgccatcgta  tactaacgga  aaattgaata  tatattatag  3780
aaggttatat  aatggactaa  aatttattat  aaaaagatat  acacctaata  atgaaataga  3840

ttcttttgtt  aaatcaggtg  aтттттaттaa  attatatgta  tcatataaca  ataatgagca  3900
cattgtaggt  tatccgaaag  atggaaatgc  ctttaataat  cttgatagaa  ttctaagagt  3960
aggttataat  gccccaggta  tccctcttta  taaaaaaatg  gaagcagtaa  aattgcgtga  4020

tttaaaaacc  tattctgtac  aacttaaaat  tatgatgat  aaaaatgcat  ctttaggact  4080
agtaggtacc  cataatggtc  aaataggcaa  cgatccaaat  agggatatat  taattgcaag  4140
caactggtac  tttaatcatt  taaaagataa  aaтттттagga  tgtgattggt  actttgtacc  4200

tacagatgaa  ggatggacaa  atgattaaac  agattgatat  gttcatgatt  actctatata  4260
aaaaattaaa  taatataaca  atctagctat  aттaттттттg  aттaтттттcт  taatatatac 4320

taataaaata  atcaaaatag  agcctatctt  aaattactga  agggctgtgt  caaaataaga  4380

ttttgacaca  gcctctactt                                                  4400
```

<210> SEQ ID NO 16
<211> LENGTH: 1315
<212> TYPE: PRT
<213> ORGANISM: Clostridium tetani

<400> SEQUENCE: 16

Met Pro Ile Thr Ile Asn Asn Phe Arg Tyr Ser Asp Pro Val Asn Asn
1               5                   10                  15

Asp Thr Ile Ile Met Met Glu Pro Pro Tyr Cys Lys Gly Leu Asp Ile
            20                  25                  30

Tyr Tyr Lys Ala Phe Lys Ile Thr Asp Arg Ile Trp Ile Val Pro Glu
        35                  40                  45

Arg Tyr Glu Phe Gly Thr Lys Pro Glu Asp Phe Asn Pro Pro Ser Ser
    50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

-continued

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
            165                 170                 175

Arg Val Asp Asn Lys Asn Tyr Phe Pro Cys Arg Asp Gly Phe Gly Ser
        180                 185                 190

Ile Met Gln Met Ala Phe Cys Pro Glu Tyr Val Pro Thr Phe Asp Asn
    195                 200                 205

Val Ile Glu Asn Ile Thr Ser Leu Thr Ile Gly Lys Ser Lys Tyr Phe
210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
            245                 250                 255

Gln Glu Ile Tyr Met Gln His Thr Tyr Pro Ile Ser Ala Glu Glu Leu
        260                 265                 270

Phe Thr Phe Gly Gly Gln Asp Ala Asn Leu Ile Ser Ile Asp Ile Lys
    275                 280                 285

Asn Asp Leu Tyr Glu Lys Thr Leu Asn Asp Tyr Lys Ala Ile Ala Asn
290                 295                 300

Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
        340                 345                 350

Ser Ile Met Tyr Gly Phe Thr Glu Ile Glu Leu Gly Lys Lys Phe Asn
    355                 360                 365

Ile Lys Thr Arg Leu Ser Tyr Phe Ser Met Asn His Asp Pro Val Lys
370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
            405                 410                 415

Arg Val Asn Thr Asn Ala Phe Arg Asn Val Asp Gly Ser Gly Leu Val
        420                 425                 430

Ser Lys Leu Ile Gly Leu Cys Lys Lys Ile Ile Pro Thr Asn Ile
    435                 440                 445

Arg Glu Asn Leu Tyr Asn Arg Thr Ala Ser Leu Thr Asp Leu Gly Gly
450                 455                 460

Glu Leu Cys Ile Lys Ile Lys Asn Glu Asp Leu Thr Phe Ile Ala Glu
465                 470                 475                 480

Lys Asn Ser Phe Ser Glu Glu Pro Phe Gln Asp Glu Ile Val Ser Tyr
            485                 490                 495

Asn Thr Lys Asn Lys Pro Leu Asn Phe Asn Tyr Ser Leu Asp Lys Ile
        500                 505                 510

Ile Val Asp Tyr Asn Leu Gln Ser Lys Ile Thr Leu Pro Asn Asp Arg
    515                 520                 525

Thr Thr Pro Val Thr Lys Gly Ile Pro Tyr Ala Pro Glu Tyr Lys Ser
530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile

```
                565                 570                 575
Thr Met Thr Asn Ser Val Asp Asp Ala Leu Ile Asn Ser Thr Lys Ile
            580                 585                 590
Tyr Ser Tyr Phe Pro Ser Val Ile Ser Lys Val Asn Gln Gly Ala Gln
            595                 600                 605
Gly Ile Leu Phe Leu Gln Trp Val Arg Asp Ile Ile Asp Asp Phe Thr
            610                 615                 620
Asn Glu Ser Ser Gln Lys Thr Thr Ile Asp Lys Ile Ser Asp Val Ser
625                 630                 635                 640
Thr Ile Val Pro Tyr Ile Gly Pro Ala Leu Asn Ile Val Lys Gln Gly
            645                 650                 655
Tyr Glu Gly Asn Phe Ile Gly Ala Leu Glu Thr Thr Gly Val Val Leu
            660                 665                 670
Leu Leu Glu Tyr Ile Pro Glu Ile Thr Leu Pro Val Ile Ala Ala Leu
            675                 680                 685
Ser Ile Ala Glu Ser Ser Thr Gln Lys Glu Lys Ile Ile Lys Thr Ile
            690                 695                 700
Asp Asn Phe Leu Glu Lys Arg Tyr Glu Lys Trp Ile Glu Val Tyr Lys
705                 710                 715                 720
Leu Val Lys Ala Lys Trp Leu Gly Thr Val Asn Thr Gln Phe Gln Lys
            725                 730                 735
Arg Ser Tyr Gln Met Tyr Arg Ser Leu Glu Tyr Gln Val Asp Ala Ile
            740                 745                 750
Lys Lys Ile Ile Asp Tyr Glu Tyr Lys Ile Tyr Ser Gly Pro Asp Lys
            755                 760                 765
Glu Gln Ile Ala Asp Glu Ile Asn Asn Leu Lys Asn Lys Leu Glu Glu
            770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
            805                 810                 815
Leu Leu Glu Phe Asp Thr Gln Ser Lys Asn Ile Leu Met Gln Tyr Ile
            820                 825                 830
Lys Ala Asn Ser Lys Phe Ile Gly Ile Thr Glu Leu Lys Lys Leu Glu
            835                 840                 845
Ser Lys Ile Asn Lys Val Phe Ser Thr Pro Ile Pro Phe Ser Tyr Ser
            850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
            885                 890                 895
Ser Asp Ile Ser Gly Phe Asn Ser Ser Val Ile Thr Tyr Pro Asp Ala
            900                 905                 910
Gln Leu Val Pro Gly Ile Asn Gly Lys Ala Ile His Leu Val Asn Asn
            915                 920                 925
Glu Ser Ser Glu Val Ile Val His Lys Ala Met Asp Ile Glu Tyr Asn
            930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
            965                 970                 975
Ile Ser Ser Met Lys Lys His Ser Leu Ser Ile Gly Ser Gly Trp Ser
            980                 985                 990
```

```
Val Ser Leu Lys Gly Asn Asn Leu Ile Trp Thr Leu Lys Asp Ser Ala
        995                 1000                1005

Gly Glu Val Arg Gln Ile Thr Phe Arg Asp Leu Pro Asp Lys Phe
    1010                1015                1020

Asn Ala Tyr Leu Ala Asn Lys Trp Val Phe Ile Thr Ile Thr Asn
    1025                1030                1035

Asp Arg Leu Ser Ser Ala Asn Leu Tyr Ile Asn Gly Val Leu Met
    1040                1045                1050

Gly Ser Ala Glu Ile Thr Gly Leu Gly Ala Ile Arg Glu Asp Asn
    1055                1060                1065

Asn Ile Thr Leu Lys Leu Asp Arg Cys Asn Asn Asn Asn Gln Tyr
    1070                1075                1080

Val Ser Ile Asp Lys Phe Arg Ile Phe Cys Lys Ala Leu Asn Pro
    1085                1090                1095

Lys Glu Ile Glu Lys Leu Tyr Thr Ser Tyr Leu Ser Ile Thr Phe
    1100                1105                1110

Leu Arg Asp Phe Trp Gly Asn Pro Leu Arg Tyr Asp Thr Glu Tyr
    1115                1120                1125

Tyr Leu Ile Pro Val Ala Ser Ser Ser Lys Asp Val Gln Leu Lys
    1130                1135                1140

Asn Ile Thr Asp Tyr Met Tyr Leu Thr Asn Ala Pro Ser Tyr Thr
    1145                1150                1155

Asn Gly Lys Leu Asn Ile Tyr Tyr Arg Arg Leu Tyr Asn Gly Leu
    1160                1165                1170

Lys Phe Ile Ile Lys Arg Tyr Thr Pro Asn Asn Glu Ile Asp Ser
    1175                1180                1185

Phe Val Lys Ser Gly Asp Phe Ile Lys Leu Tyr Val Ser Tyr Asn
    1190                1195                1200

Asn Asn Glu His Ile Val Gly Tyr Pro Lys Asp Gly Asn Ala Phe
    1205                1210                1215

Asn Asn Leu Asp Arg Ile Leu Arg Val Gly Tyr Asn Ala Pro Gly
    1220                1225                1230

Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala
    1250                1255                1260

Ser Leu Gly Leu Val Gly Thr His Asn Gly Gln Ile Gly Asn Asp
    1265                1270                1275

Pro Asn Arg Asp Ile Leu Ile Ala Ser Asn Trp Tyr Phe Asn His
    1280                1285                1290

Leu Lys Asp Lys Ile Leu Gly Cys Asp Trp Tyr Phe Val Pro Thr
    1295                1300                1305

Asp Glu Gly Trp Thr Asn Asp
    1310                1315

<210> SEQ ID NO 17
<211> LENGTH: 31
<212> TYPE: PRT
<213> ORGANISM: Clostridium botulinum

<400> SEQUENCE: 17

Lys Leu Leu Cys Val Arg Gly Ile Ile Thr Ser Lys Thr Lys Ser Leu
1               5                   10                  15

Asp Lys Gly Tyr Asn Lys Ala Leu Asn Asp Leu Cys Ile Lys Val
```

```
                    20                  25                  30

<210> SEQ ID NO 18
<211> LENGTH: 16
<212> TYPE: PRT
<213> ORGANISM: Clostridium botulinum

<400> SEQUENCE: 18

Ile Gln Met Cys Lys Ser Val Lys Ala Pro Gly Ile Cys Ile Asp Val
1               5                   10                  15

<210> SEQ ID NO 19
<211> LENGTH: 25
<212> TYPE: PRT
<213> ORGANISM: Clostridium botulinum

<400> SEQUENCE: 19

Thr Lys Phe Cys His Lys Ala Ile Asp Gly Arg Ser Leu Tyr Asn Lys
1               5                   10                  15

Thr Leu Asp Cys Arg Glu Leu Leu Val
            20                  25

<210> SEQ ID NO 20
<211> LENGTH: 20
<212> TYPE: PRT
<213> ORGANISM: Clostridium botulinum

<400> SEQUENCE: 20

Thr Lys Val Cys Leu Arg Leu Thr Lys Asn Ser Arg Asp Asp Ser Thr
1               5                   10                  15

Cys Ile Lys Val
            20

<210> SEQ ID NO 21
<211> LENGTH: 21
<212> TYPE: PRT
<213> ORGANISM: Clostridium botulinum

<400> SEQUENCE: 21

Ile Arg Phe Cys Lys Asn Ile Val Ser Val Lys Gly Ile Arg Lys Ser
1               5                   10                  15

Ile Cys Ile Glu Ile
            20

<210> SEQ ID NO 22
<211> LENGTH: 23
<212> TYPE: PRT
<213> ORGANISM: Clostridium botulinum

<400> SEQUENCE: 22

Val Lys Phe Cys Lys Ser Val Ile Pro Arg Lys Gly Thr Lys Ala Pro
1               5                   10                  15

Pro Arg Leu Cys Ile Arg Val
            20

<210> SEQ ID NO 23
<211> LENGTH: 21
<212> TYPE: PRT
<213> ORGANISM: Clostridium botulinum

<400> SEQUENCE: 23

Ile Ala Met Cys Lys Pro Val Met Tyr Lys Asn Thr Gly Lys Ser Glu
1               5                   10                  15
```

-continued

```
Gln Cys Ile Ile Val
            20

<210> SEQ ID NO 24
<211> LENGTH: 35
<212> TYPE: PRT
<213> ORGANISM: Clostridium tetani

<400> SEQUENCE: 24

Ile Gly Leu Cys Lys Lys Ile Ile Pro Pro Thr Asn Ile Arg Glu Asn
1               5                   10                  15

Leu Tyr Asn Arg Thr Ala Ser Leu Thr Asp Leu Gly Gly Glu Leu Cys
            20                  25                  30

Ile Lys Ile
        35

<210> SEQ ID NO 25
<211> LENGTH: 7
<212> TYPE: PRT
<213> ORGANISM: artificial sequence
<220> FEATURE:
<223> OTHER INFORMATION: ligase recognition motif

<400> SEQUENCE: 25

Ala Leu Ala Pro Tyr Ile Pro
1               5

<210> SEQ ID NO 26
<211> LENGTH: 12
<212> TYPE: PRT
<213> ORGANISM: artificial sequence
<220> FEATURE:
<223> OTHER INFORMATION: ligase recognition motif

<400> SEQUENCE: 26

Glu Thr Phe Ser Asp Leu Trp Lys Leu Leu Pro Glu
1               5                   10

<210> SEQ ID NO 27
<211> LENGTH: 12
<212> TYPE: PRT
<213> ORGANISM: artificial sequence
<220> FEATURE:
<223> OTHER INFORMATION: ligase recognition motif

<400> SEQUENCE: 27

Thr Ser Phe Ala Glu Tyr Trp Asn Leu Leu Ser Pro
1               5                   10

<210> SEQ ID NO 28
<211> LENGTH: 12
<212> TYPE: PRT
<213> ORGANISM: artificial sequence
<220> FEATURE:
<223> OTHER INFORMATION: ligase recognition motif

<400> SEQUENCE: 28

Leu Thr Phe Glu His Tyr Trp Ala Gln Leu Thr Ser
1               5                   10

<210> SEQ ID NO 29
<211> LENGTH: 12
<212> TYPE: PRT
<213> ORGANISM: artificial sequence
<220> FEATURE:
```

<223> OTHER INFORMATION: ligase recognition motif

<400> SEQUENCE: 29

Leu Thr Phe Glu His Trp Trp Ala Gln Leu Thr Ser
1               5                   10

<210> SEQ ID NO 30
<211> LENGTH: 12
<212> TYPE: PRT
<213> ORGANISM: artificial sequence
<220> FEATURE:
<223> OTHER INFORMATION: ligase recognition motif

<400> SEQUENCE: 30

Leu Thr Phe Glu His Ser Trp Ala Gln Leu Thr Ser
1               5                   10

<210> SEQ ID NO 31
<211> LENGTH: 12
<212> TYPE: PRT
<213> ORGANISM: artificial sequence
<220> FEATURE:
<223> OTHER INFORMATION: ligase recognition motif

<400> SEQUENCE: 31

Glu Thr Phe Glu His Asn Trp Ala Gln Leu Thr Ser
1               5                   10

<210> SEQ ID NO 32
<211> LENGTH: 12
<212> TYPE: PRT
<213> ORGANISM: artificial sequence
<220> FEATURE:
<223> OTHER INFORMATION: ligase recognition motif

<400> SEQUENCE: 32

Leu Thr Phe Glu His Asn Trp Ala Gln Leu Thr Ser
1               5                   10

<210> SEQ ID NO 33
<211> LENGTH: 12
<212> TYPE: PRT
<213> ORGANISM: artificial sequence
<220> FEATURE:
<223> OTHER INFORMATION: ligase recognition motif

<400> SEQUENCE: 33

Leu Thr Phe Glu His Trp Trp Ala Ser Leu Thr Ser
1               5                   10

<210> SEQ ID NO 34
<211> LENGTH: 12
<212> TYPE: PRT
<213> ORGANISM: artificial sequence
<220> FEATURE:
<223> OTHER INFORMATION: ligase recognition motif

<400> SEQUENCE: 34

Leu Thr Phe Glu His Trp Trp Ser Ser Leu Thr Ser
1               5                   10

<210> SEQ ID NO 35
<211> LENGTH: 12
<212> TYPE: PRT
<213> ORGANISM: artificial sequence
<220> FEATURE:
<223> OTHER INFORMATION: ligase recognition motif

```
<400> SEQUENCE: 35

Leu Thr Phe Thr His Trp Trp Ala Gln Leu Thr Ser
1               5                   10

<210> SEQ ID NO 36
<211> LENGTH: 12
<212> TYPE: PRT
<213> ORGANISM: artificial sequence
<220> FEATURE:
<223> OTHER INFORMATION: ligase recognition motif

<400> SEQUENCE: 36

Glu Thr Phe Glu His Trp Trp Ala Gln Leu Thr Ser
1               5                   10

<210> SEQ ID NO 37
<211> LENGTH: 12
<212> TYPE: PRT
<213> ORGANISM: artificial sequence
<220> FEATURE:
<223> OTHER INFORMATION: ligase recognition motif

<400> SEQUENCE: 37

Leu Thr Phe Glu His Trp Trp Ser Gln Leu Thr Ser
1               5                   10

<210> SEQ ID NO 38
<211> LENGTH: 12
<212> TYPE: PRT
<213> ORGANISM: artificial sequence
<220> FEATURE:
<223> OTHER INFORMATION: ligase recognition motif

<400> SEQUENCE: 38

Leu Thr Phe Glu His Trp Trp Ala Gln Leu Leu Ser
1               5                   10

<210> SEQ ID NO 39
<211> LENGTH: 12
<212> TYPE: PRT
<213> ORGANISM: artificial sequence
<220> FEATURE:
<223> OTHER INFORMATION: ligase recognition motif

<400> SEQUENCE: 39

Glu Thr Phe Glu His Trp Trp Ser Gln Leu Leu Ser
1               5                   10

<210> SEQ ID NO 40
<211> LENGTH: 9
<212> TYPE: PRT
<213> ORGANISM: artificial sequence
<220> FEATURE:
<223> OTHER INFORMATION: ligase recognition motif

<400> SEQUENCE: 40

Arg Phe Met Asp Tyr Trp Glu Gly Leu
1               5

<210> SEQ ID NO 41
<211> LENGTH: 12
<212> TYPE: PRT
<213> ORGANISM: artificial sequence
<220> FEATURE:
<223> OTHER INFORMATION: ligase recognition motif
```

```
<400> SEQUENCE: 41

Met Pro Arg Phe Met Asp Tyr Trp Glu Gly Leu Asn
1               5                   10

<210> SEQ ID NO 42
<211> LENGTH: 15
<212> TYPE: PRT
<213> ORGANISM: artificial sequence
<220> FEATURE:
<223> OTHER INFORMATION: ligase recognition motif

<400> SEQUENCE: 42

Ser Gln Glu Thr Phe Ser Asp Leu Trp Lys Leu Leu Pro Glu Asn
1               5                   10                  15

<210> SEQ ID NO 43
<211> LENGTH: 12
<212> TYPE: PRT
<213> ORGANISM: artificial sequence
<220> FEATURE:
<223> OTHER INFORMATION: ligase recognition motif
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (4)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 43

Xaa Xaa Phe Xaa Xaa Xaa Trp Xaa Xaa Leu Xaa Xaa
1               5                   10

<210> SEQ ID NO 44
<211> LENGTH: 14
<212> TYPE: PRT
<213> ORGANISM: artificial sequence
<220> FEATURE:
<223> OTHER INFORMATION: ligase recognition motif

<400> SEQUENCE: 44

Glu Leu Glu Ser Pro Pro Pro Pro Tyr Ser Arg Tyr Pro Met
1               5                   10

<210> SEQ ID NO 45
<211> LENGTH: 7
<212> TYPE: PRT
<213> ORGANISM: artificial sequence
<220> FEATURE:
<223> OTHER INFORMATION: ligase recognition motif

<400> SEQUENCE: 45

Lys Val Gly Phe Phe Lys Arg
1               5

<210> SEQ ID NO 46
<211> LENGTH: 10
<212> TYPE: PRT
<213> ORGANISM: artificial sequence
<220> FEATURE:
```

```
<223> OTHER INFORMATION: ligase recognition motif

<400> SEQUENCE: 46

Leu Leu Val Arg Gly Arg Thr Leu Val Val
1               5                   10

<210> SEQ ID NO 47
<211> LENGTH: 10
<212> TYPE: PRT
<213> ORGANISM: artificial sequence
<220> FEATURE:
<223> OTHER INFORMATION: ligase recognition motif

<400> SEQUENCE: 47

Asp Arg His Asp Ser Gly Leu Asp Ser Met
1               5                   10

<210> SEQ ID NO 48
<211> LENGTH: 7
<212> TYPE: PRT
<213> ORGANISM: artificial sequence
<220> FEATURE:
<223> OTHER INFORMATION: ligase recognition motif
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 48

Pro Xaa Ala Xaa Val Xaa Pro
1               5

<210> SEQ ID NO 49
<211> LENGTH: 7
<212> TYPE: PRT
<213> ORGANISM: artificial sequence
<220> FEATURE:
<223> OTHER INFORMATION: ligase recognition motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 49

Pro Pro Xaa Tyr Xaa Xaa Met
1               5

<210> SEQ ID NO 50
<211> LENGTH: 4
<212> TYPE: PRT
<213> ORGANISM: artificial sequence
<220> FEATURE:
<223> OTHER INFORMATION: ligase recognition motif
<220> FEATURE:
<221> NAME/KEY: misc_feature
<222> LOCATION: (3)..(3)
<223> OTHER INFORMATION: Xaa can be any naturally occurring amino acid

<400> SEQUENCE: 50
```

```
Pro Pro Xaa Tyr
1

<210> SEQ ID NO 51
<211> LENGTH: 3819
<212> TYPE: DNA
<213> ORGANISM: Artificial sequence
<220> FEATURE:
<223> OTHER INFORMATION: recombinant protein BONT/E with MDM2 binding
      motif

<400> SEQUENCE: 51
atgccgaaaa tcaacagctt caactataac gatccggtga acgatcgtac catcctgtat     60
attaaaccgg gcggttgcca ggaattttac aaaagcttca acatcatgaa aaacatctgg    120
attattccgg aacgtaacgt gattggcacc accccgcagg attttcatcc gccgaccagc    180
ctgaaaaacg gcgatagcag ctattatgat ccgaactatc tgcagtctga tgaagaaaaa    240
gatcgcttcc tgaaaatcgt gaccaaaatc ttcaaccgca tcaacaacaa cctgagcggc    300
ggcattctgc tggaagaact gagcaaagcg aatccgtatc tgggcaacga taacactcca    360
gataaccagt ttcatattgg tgatgcgagc gcggtggaaa ttaaatttag caacggctct    420
caggacattc tgctgccgaa cgtgattatt atgggcgcgg aaccggacct gtttgaaacc    480
aacagcagca acattagcct gcgtaacaac tatatgccga gcaaccatgg ttttggcagc    540
attgcgattg tgacctttag cccggaatat agctttcgct tcaacgataa cagcatgaac    600
gaatttattc aggacccggc gctgaccctg atgcacgagc tgattcatag cctgcatggc    660
ctgtatggcg cgaaaggcat taccaccaaa tataccatca cccagaaaca gaatccgctg    720
attaccaaca ttcgtggcac caacattgaa gaatttctga cctttggcgg caccgatctg    780
aacattatta ccagcgcgca gagcaacgat atctatacca acctgctggc cgattataaa    840
aaaatcgcgt ctaaactgag caaagtgcag gtgagcaatc cgctgctgaa tccgtataaa    900
gatgtgtttg aagcgaaata tggcctggat aaagatgcta gcggcattta tagcgtgaac    960
atcaacaaat tcaacgacat cttcaaaaaa ctgtatagct ttaccgaatt tgatctggcc   1020
accaaatttc aggtgaaatg ccgccagacc tatattggcc agtataaata ttttaaactg   1080
agcaacctgc tgaacgatag catttacaac atcagcgaag gctataacat caacaacctg   1140
aaagtgaact ttcgtggcca gaacgcgaat ttaaatccgc gtattattac cccgattacc   1200
ggccgtggac tagtgaaaaa aattatccgt tttgcgtgc gtggcattat caccagcctg   1260
acctttgaac ataattgggc acagctgacc agcaaaagcc tggtgccgcg tggcagcaaa   1320
gcgttaaatg atttatgcat cgaaatcaac aacggcgaac tgttttttgt ggcgagcgaa   1380
aacagctata acgatgataa catcaacacc ccgaaagaaa ttgatgatac cgtgaccagc   1440
aataacaact acgaaaacga tctggatcag gtgattctga actttaacag cgaaagcgca   1500
ccgggcctgt ctgatgaaaa actgaacctg accattcaga acgatgcgta tatcccgaaa   1560
tatgatagca acggcaccag cgatattgaa cagcatgatg tgaacgaact gaacgtgttt   1620
ttttatctgg atgcgcagaa agtgccggaa ggcgaaaaca acgtgaatct gaccagctca   1680
attgataccg cgctgctgga acagccgaaa atctatacct tttttagcag cgaattcatc   1740
aacaacgtga acaaaccggt gcaggcggcg ctgtttgtga gctggattca gcaggtgctg   1800
gttgatttta ccaccgaagc gaaccagaaa agcaccgtgg ataaaattgc ggatattagc   1860
attgtggtgc cgtatattgg cctggccctg aacattggca acgaagcgca gaaaggcaac   1920
```

```
tttaaagatg cgctggaact gctgggtgcg ggcattctgc tggaatttga accggaactg    1980
ctgattccga ccattctggt gtttaccatc aaaagctttc tgggcagcag cgataacaaa    2040
aacaaagtga tcaaagcgat taacaacgcg ctgaaagaac gtgatgaaaa atggaaagaa    2100
gtgtatagct tcattgtgtc taactggatg accaaaatca cacccagtt caacaaacgt     2160 aaagaacaaa tgtatcaggc gctgcagaac caggtgaacg cgattaaaac catcatcgaa    2220
agcaaataca acagctacac cctggaagaa aaaacgaac tgaccaacaa atatgacatc     2280
aaacaaatcg aaatgaact gaaccagaaa gtgagcattg ccatgaacaa cattgatcgc     2340
tttctgaccg aaagcagcat tagctacctg atgaaactga tcaacgaagt gaaaatcaac    2400
aaactgcgcg aatatgatga aaacgtgaaa acctacctgc tgaactatat tattcagcat    2460
ggcagcattc tgggcgaaag ccagcaagaa ctgaacagca tggttaccga tacccctgaac   2520 aacagcattc cgtttaaact gagcagctac accgatgata aatcctgat cagctacttc     2580 aacaaattct tcaaacgcat caaaagcagc agcgtgctga acatgcgtta taaaaacgat    2640
aaatacgtag ataccagcgg ctatgatagc aatatcaaca ttaacggtga tgtgtataaa    2700
tacccgacca acaaaaacca gttcggcatc tacaacgata aactgagcga agtgaacatt    2760
agccagaacg attatatcat ctacgataat aaatataaaa acttcagcat cagcttttgg    2820
gtgcgtattc cgaactacga taacaaaatc gtgaacgtga acaacgaata caccatcatt    2880
aactgcatgc gtgataacaa cagcggctgg aaagtgagcc tgaaccataa cgaaatcatc    2940
tggaccctgc aggataacgc cggcattaac cagaaactgg cctttaacta tggcaacgcg    3000
aacggcatta gcgattacat caacaaatgg atctttgtga ccattaccaa cgatcgtctg    3060
ggcgatagca aactgtatat taacggcaac ctgatcgacc agaaaagcat tctgaacctg    3120
ggcaacattc atgtgagcga taacatcctg ttcaaaattg tgaactgcag ctataccgt     3180 tatattggca tccgctattt caacatcttc gataaagaac tggatgaaac cgaaattcag    3240
accctgtata gcaacgaacc gaacaccaac atcctgaaag atttctgggg caactatctg    3300
ctgtacgata agaatatta tctgctgaac gtgctgaaac cgaacaactt tattgatcgc     3360
cgtaaagata gcaccctgag cattaacaac attcgtagca ccattctgct ggccaaccgt    3420
ctgtatagcg gcattaaagt gaaaattcag cgcgtgaaca atagcagcac caacgataac    3480
ctggtgcgta aaaacgatca ggtgtatatc aactttgtgg ccagcaaaac ccacctgttt    3540
ccgctgtatg cggataccgc gaccaccaac aaagaaaaaa ccattaaaat cagcagcagc    3600
ggcaaccgtt ttaaccaggt ggtggtgatg aacagcgtgg gcaacaactg tacaatgaac    3660
ttcaaaaaca caacggcaa caacattggc ctgctgggct taaagcgga taccgtggtg     3720 gcgagcacct ggtattatac ccacatgcgt gatcatacca acagcaacgg ctgctttttgg   3780 aactttatta gcgaagaaca tggctggcag gaaaaatga                          3819
```

<210> SEQ ID NO 52
<211> LENGTH: 1272
<212> TYPE: PRT
<213> ORGANISM: artificial sequence
<220> FEATURE:
<223> OTHER INFORMATION: recombinant protein BONT/E with MDM2 binding
      motif

<400> SEQUENCE: 52

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser

-continued

```
                20                  25                  30
Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
 50                  55                  60

Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
                    85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
                115                 120                 125

Ala Ser Ala Val Glu Ile Lys Phe Ser Asn Gly Ser Gln Asp Ile Leu
            130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                    165                 170                 175

Gly Phe Gly Ser Ile Ala Ile Val Thr Phe Ser Pro Glu Tyr Ser Phe
                180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
            210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                    245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                    325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                    405                 410                 415

Ile Thr Ser Leu Thr Phe Glu His Asn Trp Ala Gln Leu Thr Ser Lys
                420                 425                 430

Ser Leu Val Pro Arg Gly Ser Lys Ala Leu Asn Asp Leu Cys Ile Glu
            435                 440                 445
```

-continued

```
Ile Asn Asn Gly Glu Leu Phe Phe Val Ala Ser Glu Asn Ser Tyr Asn
450                 455                 460
Asp Asp Asn Ile Asn Thr Pro Lys Glu Ile Asp Asp Thr Val Thr Ser
465                 470                 475                 480
Asn Asn Asn Tyr Glu Asn Asp Leu Asp Gln Val Ile Leu Asn Phe Asn
                485                 490                 495
Ser Glu Ser Ala Pro Gly Leu Ser Asp Glu Lys Leu Asn Leu Thr Ile
            500                 505                 510
Gln Asn Asp Ala Tyr Ile Pro Lys Tyr Asp Ser Asn Gly Thr Ser Asp
            515                 520                 525
Ile Glu Gln His Asp Val Asn Glu Leu Asn Val Phe Phe Tyr Leu Asp
530                 535                 540
Ala Gln Lys Val Pro Glu Gly Glu Asn Val Asn Leu Thr Ser Ser
545                 550                 555                 560
Ile Asp Thr Ala Leu Leu Glu Gln Pro Lys Ile Tyr Thr Phe Phe Ser
                565                 570                 575
Ser Glu Phe Ile Asn Asn Val Asn Lys Pro Val Gln Ala Ala Leu Phe
                580                 585                 590
Val Ser Trp Ile Gln Gln Val Leu Val Asp Phe Thr Thr Glu Ala Asn
            595                 600                 605
Gln Lys Ser Thr Val Asp Lys Ile Ala Asp Ile Ser Ile Val Val Pro
            610                 615                 620
Tyr Ile Gly Leu Ala Leu Asn Ile Gly Asn Glu Ala Gln Lys Gly Asn
625                 630                 635                 640
Phe Lys Asp Ala Leu Glu Leu Leu Gly Ala Gly Ile Leu Leu Glu Phe
                645                 650                 655
Glu Pro Glu Leu Leu Ile Pro Thr Ile Leu Val Phe Thr Ile Lys Ser
            660                 665                 670
Phe Leu Gly Ser Ser Asp Asn Lys Asn Lys Val Ile Lys Ala Ile Asn
            675                 680                 685
Asn Ala Leu Lys Glu Arg Asp Glu Lys Trp Lys Glu Val Tyr Ser Phe
690                 695                 700
Ile Val Ser Asn Trp Met Thr Lys Ile Asn Thr Gln Phe Asn Lys Arg
705                 710                 715                 720
Lys Glu Gln Met Tyr Gln Ala Leu Gln Asn Gln Val Asn Ala Ile Lys
                725                 730                 735
Thr Ile Ile Glu Ser Lys Tyr Asn Ser Tyr Thr Leu Glu Glu Lys Asn
                740                 745                 750
Glu Leu Thr Asn Lys Tyr Asp Ile Lys Gln Ile Glu Asn Glu Leu Asn
            755                 760                 765
Gln Lys Val Ser Ile Ala Met Asn Asn Ile Asp Arg Phe Leu Thr Glu
            770                 775                 780
Ser Ser Ile Ser Tyr Leu Met Lys Leu Ile Asn Glu Val Lys Ile Asn
785                 790                 795                 800
Lys Leu Arg Glu Tyr Asp Glu Asn Val Lys Thr Tyr Leu Leu Asn Tyr
                805                 810                 815
Ile Ile Gln His Gly Ser Ile Leu Gly Glu Ser Gln Gln Glu Leu Asn
                820                 825                 830
Ser Met Val Thr Asp Thr Leu Asn Asn Ser Ile Pro Phe Lys Leu Ser
            835                 840                 845
Ser Tyr Thr Asp Asp Lys Ile Leu Ile Ser Tyr Phe Asn Lys Phe Phe
            850                 855                 860
```

-continued

```
Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
```

```
              1265                1270
```

<210> SEQ ID NO 53
<211> LENGTH: 1272
<212> TYPE: PRT
<213> ORGANISM: Clostridium botulinum

<400> SEQUENCE: 53

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Lys Lys Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365
```

```
Tyr Asn Ile Ser Glu Gly Tyr Asn Ile Asn Asn Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
                420                 425                 430

Ser Leu Val Pro Arg Gly Ser Lys Ala Leu Asn Asp Leu Cys Ile Glu
                435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
                500                 505                 510

Gln Asn Asp Ala Tyr Ile Pro Lys Tyr Asp Ser Asn Gly Thr Ser Asp
                515                 520                 525

Ile Glu Gln His Asp Val Asn Glu Leu Asn Val Phe Phe Tyr Leu Asp
                530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
                595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
                675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
                755                 760                 765

Gln Lys Val Ser Ile Ala Met Asn Asn Ile Asp Arg Phe Leu Thr Glu
                770                 775                 780

Ser Ser Ile Ser Tyr Leu Met Lys Leu Ile Asn Glu Val Lys Ile Asn
```

-continued

```
            785                 790                 795                 800
Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
        850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
        930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala  Asn Gly Ile Ser Asp Tyr Ile Asn
        995                 1000                1005

Lys Trp  Ile Phe Val Thr Ile  Thr Asn Asp Arg Leu  Gly Asp Ser
        1010                1015                1020

Lys Leu  Tyr Ile Asn Gly Asn  Leu Ile Asp Gln Lys  Ser Ile Leu
        1025                1030                1035

Asn Leu  Gly Asn Ile His Val  Ser Asp Asn Ile Leu  Phe Lys Ile
        1040                1045                1050

Val Asn  Cys Ser Tyr Thr Arg  Tyr Ile Gly Ile Arg  Tyr Phe Asn
        1055                1060                1065

Ile Phe  Asp Lys Glu Leu Asp  Glu Thr Glu Ile Gln  Thr Leu Tyr
        1070                1075                1080

Ser Asn  Glu Pro Asn Thr Asn  Ile Leu Lys Asp Phe  Trp Gly Asn
        1085                1090                1095

Tyr Leu  Leu Tyr Asp Lys Glu  Tyr Tyr Leu Leu Asn  Val Leu Lys
        1100                1105                1110

Pro Asn  Asn Phe Ile Asp Arg  Arg Lys Asp Ser Thr  Leu Ser Ile
        1115                1120                1125

Asn Asn  Ile Arg Ser Thr Ile  Leu Leu Ala Asn Arg  Leu Tyr Ser
        1130                1135                1140

Gly Ile  Lys Val Lys Ile Gln  Arg Val Asn Asn Ser  Ser Thr Asn
        1145                1150                1155

Asp Asn  Leu Val Arg Lys Asn  Asp Gln Val Tyr Ile  Asn Phe Val
        1160                1165                1170

Ala Ser  Lys Thr His Leu Phe  Pro Leu Tyr Ala Asp  Thr Ala Thr
        1175                1180                1185

Thr Asn  Lys Glu Lys Thr Ile  Lys Ile Ser Ser Ser  Gly Asn Arg
        1190                1195                1200
```

```
Phe Asn Gln Val Val Met Asn Ser Val Gly Asn Asn Cys Thr
    1205                1210                1215

Met Asn Phe Lys Asn Asn Asn Gly Asn Asn Ile Gly Leu Leu Gly
1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270
```

<210> SEQ ID NO 54
<211> LENGTH: 1272
<212> TYPE: PRT
<213> ORGANISM: Clostridium botulinum

<400> SEQUENCE: 54

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Lys Lys Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Lys Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
```

-continued

```
                290                 295                 300
Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
                420                 425                 430

Ser Leu Val Pro Arg Gly Ser Lys Ala Leu Asn Asp Leu Cys Ile Glu
                435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
                500                 505                 510

Gln Asn Asp Ala Tyr Ile Pro Lys Tyr Asp Ser Asn Gly Thr Ser Asp
                515                 520                 525

Ile Glu Gln His Asp Val Asn Glu Leu Asn Val Phe Phe Tyr Leu Asp
                530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
                595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
                675                 680                 685

Asn Ala Leu Lys Glu Arg Asp Glu Lys Trp Lys Glu Val Tyr Ser Phe
                690                 695                 700

Ile Val Ser Asn Trp Met Thr Lys Ile Asn Thr Gln Phe Asn Lys Arg
705                 710                 715                 720
```

```
Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
            850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
            930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala Asn Gly Ile Ser Asp Tyr Ile Asn
                995                 1000                1005

Lys Trp Ile Phe Val Thr Ile Thr Asn Asp Arg Leu Gly Asp Ser
            1010                1015                1020

Lys Leu Tyr Ile Asn Gly Asn Leu Ile Asp Gln Lys Ser Ile Leu
            1025                1030                1035

Asn Leu Gly Asn Ile His Val Ser Asp Asn Ile Leu Phe Lys Ile
            1040                1045                1050

Val Asn Cys Ser Tyr Thr Arg Tyr Ile Gly Ile Arg Tyr Phe Asn
            1055                1060                1065

Ile Phe Asp Lys Glu Leu Asp Glu Thr Glu Ile Gln Thr Leu Tyr
            1070                1075                1080

Ser Asn Glu Pro Asn Thr Asn Ile Leu Lys Asp Phe Trp Gly Asn
            1085                1090                1095

Tyr Leu Leu Tyr Asp Lys Glu Tyr Tyr Leu Leu Asn Val Leu Lys
            1100                1105                1110

Pro Asn Asn Phe Ile Asp Arg Arg Lys Asp Ser Thr Leu Ser Ile
            1115                1120                1125
```

-continued

```
Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asp Gln Val Tyr Ile Asn Phe Val
1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 55
<211> LENGTH: 1272
<212> TYPE: PRT
<213> ORGANISM: Clostridium botulinum

<400> SEQUENCE: 55

Met Pro Lys Ile Asn Ser Phe Asn Tyr Asn Asp Pro Val Asn Asp Arg
1                5                   10                  15

Thr Ile Leu Tyr Ile Lys Pro Gly Gly Cys Lys Lys Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Lys Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Gly Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220
```

```
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
        530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
        580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640
```

-continued

```
Phe Lys Asp Ala Leu Glu Leu Leu Gly Ala Gly Ile Leu Leu Glu Phe
                645                 650                 655
Glu Pro Glu Leu Leu Ile Pro Thr Ile Leu Val Phe Thr Ile Lys Ser
            660                 665                 670
Phe Leu Gly Ser Ser Asp Asn Lys Asn Lys Val Ile Lys Ala Ile Asn
        675                 680                 685
Asn Ala Leu Lys Glu Arg Asp Glu Lys Trp Lys Glu Val Tyr Ser Phe
690                 695                 700
Ile Val Ser Asn Trp Met Thr Lys Ile Asn Thr Gln Phe Asn Lys Arg
705                 710                 715                 720
Lys Glu Gln Met Tyr Gln Ala Leu Gln Asn Gln Val Asn Ala Ile Lys
                725                 730                 735
Thr Ile Ile Glu Ser Lys Tyr Asn Ser Tyr Thr Leu Glu Glu Lys Asn
            740                 745                 750
Glu Leu Thr Asn Lys Tyr Asp Ile Lys Gln Ile Glu Asn Glu Leu Asn
        755                 760                 765
Gln Lys Val Ser Ile Ala Met Asn Asn Ile Asp Arg Phe Leu Thr Glu
770                 775                 780
Ser Ser Ile Ser Tyr Leu Met Lys Leu Ile Asn Glu Val Lys Ile Asn
785                 790                 795                 800
Lys Leu Arg Glu Tyr Asp Glu Asn Val Lys Thr Tyr Leu Leu Asn Tyr
                805                 810                 815
Ile Ile Gln His Gly Ser Ile Leu Gly Glu Ser Gln Gln Glu Leu Asn
            820                 825                 830
Ser Met Val Thr Asp Thr Leu Asn Asn Ser Ile Pro Phe Lys Leu Ser
        835                 840                 845
Ser Tyr Thr Asp Asp Lys Ile Leu Ile Ser Tyr Phe Asn Lys Phe Phe
850                 855                 860
Lys Arg Ile Lys Ser Ser Ser Val Leu Asn Met Arg Tyr Lys Asn Asp
865                 870                 875                 880
Lys Tyr Val Asp Thr Ser Gly Tyr Asp Ser Asn Ile Asn Ile Asn Gly
                885                 890                 895
Asp Val Tyr Lys Tyr Pro Thr Asn Lys Asn Gln Phe Gly Ile Tyr Asn
            900                 905                 910
Asp Lys Leu Ser Glu Val Asn Ile Ser Gln Asn Asp Tyr Ile Ile Tyr
        915                 920                 925
Asp Asn Lys Tyr Lys Asn Phe Ser Ile Ser Phe Trp Val Arg Ile Pro
930                 935                 940
Asn Tyr Asp Asn Lys Ile Val Asn Val Asn Asn Glu Tyr Thr Ile Ile
945                 950                 955                 960
Asn Cys Met Arg Asp Asn Asn Ser Gly Trp Lys Val Ser Leu Asn His
                965                 970                 975
Asn Glu Ile Ile Trp Thr Leu Gln Asp Asn Ala Gly Ile Asn Gln Lys
            980                 985                 990
Leu Ala Phe Asn Tyr Gly Asn Ala Asn Gly Ile Ser Asp Tyr Ile Asn
        995                 1000                1005
Lys Trp Ile Phe Val Thr Ile Thr Asn Asp Arg Leu Gly Asp Ser
    1010                1015                1020
Lys Leu Tyr Ile Asn Gly Asn Leu Ile Asp Gln Lys Ser Ile Leu
    1025                1030                1035
Asn Leu Gly Asn Ile His Val Ser Asp Asn Ile Leu Phe Lys Ile
    1040                1045                1050
Val Asn Cys Ser Tyr Thr Arg Tyr Ile Gly Ile Arg Tyr Phe Asn
```

```
                1055                1060                1065
Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 56
<211> LENGTH: 1272
<212> TYPE: PRT
<213> ORGANISM: Clostridium botulinum

<400> SEQUENCE: 56

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Lys Asp Phe His Pro Pro Thr Ser Leu Lys Asn Gly
        50                  55                  60

Asp Ser Ser Tyr Tyr Asp Pro Lys Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140
```

```
Leu Pro Asn Val Ile Ile Met Gly Ala Glu Pro Asp Leu Phe Glu Thr
145                 150                 155                 160

Asn Ser Ser Asn Ile Ser Leu Arg Asn Tyr Met Pro Ser Asn His
            165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
            210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
            245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
            325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Lys Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
            405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
            485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Val Asn Leu Thr Ser Ser
545                 550                 555                 560

Ile Asp Thr Ala Leu Leu Glu Gln Pro Lys Ile Tyr Thr Phe Phe Ser
```

```
                565                 570                 575
Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
                595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
                675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
                755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
                850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
                930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990
```

```
Leu Ala Phe Asn Tyr Gly Asn Ala  Asn Gly Ile Ser Asp  Tyr Ile Asn
         995                 1000                 1005

Lys Trp  Ile Phe Val Thr Ile  Thr Asn Asp Arg Leu  Gly Asp Ser
    1010                 1015                 1020

Lys Leu  Tyr Ile Asn Gly Asn  Leu Ile Asp Gln Lys  Ser Ile Leu
    1025                 1030                 1035

Asn Leu  Gly Asn Ile His Val  Ser Asp Asn Ile Leu  Phe Lys Ile
    1040                 1045                 1050

Val Asn  Cys Ser Tyr Thr Arg  Tyr Ile Gly Ile Arg  Tyr Phe Asn
    1055                 1060                 1065

Ile Phe  Asp Lys Glu Leu Asp  Glu Thr Glu Ile Gln  Thr Leu Tyr
    1070                 1075                 1080

Ser Asn  Glu Pro Asn Thr Asn  Ile Leu Lys Asp Phe  Trp Gly Asn
    1085                 1090                 1095

Tyr Leu  Leu Tyr Asp Lys Glu  Tyr Tyr Leu Leu Asn  Val Leu Lys
    1100                 1105                 1110

Pro Asn  Asn Phe Ile Asp Arg  Arg Lys Asp Ser Thr  Leu Ser Ile
    1115                 1120                 1125

Asn Asn  Ile Arg Ser Thr Ile  Leu Leu Ala Asn Arg  Leu Tyr Ser
    1130                 1135                 1140

Gly Ile  Lys Val Lys Ile Gln  Arg Val Asn Asn Ser  Ser Thr Asn
    1145                 1150                 1155

Asp Asn  Leu Val Arg Lys Asn  Asp Gln Val Tyr Ile  Asn Phe Val
    1160                 1165                 1170

Ala Ser  Lys Thr His Leu Phe  Pro Leu Tyr Ala Asp  Thr Ala Thr
    1175                 1180                 1185

Thr Asn  Lys Glu Lys Thr Ile  Lys Ile Ser Ser Ser  Gly Asn Arg
    1190                 1195                 1200

Phe Asn  Gln Val Val Val Met  Asn Ser Val Gly Asn  Asn Cys Thr
    1205                 1210                 1215

Met Asn  Phe Lys Asn Asn Asn  Gly Asn Ile Gly Leu  Leu Gly
    1220                 1225                 1230

Phe Lys  Ala Asp Thr Val Val  Ala Ser Thr Trp Tyr  Tyr Thr His
    1235                 1240                 1245

Met Arg  Asp His Thr Asn Ser  Asn Gly Cys Phe Trp  Asn Phe Ile
    1250                 1255                 1260

Ser Glu  Glu His Gly Trp Gln  Glu Lys
    1265                 1270

<210> SEQ ID NO 57
<211> LENGTH: 1272
<212> TYPE: PRT
<213> ORGANISM: Clostridium botulinum

<400> SEQUENCE: 57

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Lys Asp Phe His Pro Pro Thr Ser Leu Lys Asn Gly
    50                  55                  60

Asp Ser Ser Tyr Tyr Asp Pro Lys Tyr Leu Gln Ser Asp Glu Glu Lys
```

```
                65                  70                  75                  80
Asp Arg Phe Leu Lys Ile Val Thr Lys Ile Phe Asn Arg Ile Asn Asn
                        85                  90                  95
Asn Leu Ser Gly Gly Ile Leu Glu Glu Leu Ser Lys Ala Asn Pro
                100                 105                 110
Tyr Leu Gly Asn Asp Asn Thr Pro Asp Asn Gln Phe His Ile Gly Asp
                115                 120                 125
Ala Ser Ala Val Glu Ile Lys Phe Ser Asn Gly Ser Gln Asp Ile Leu
            130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                    165                 170                 175
Gly Phe Gly Ser Ile Ala Ile Val Thr Phe Ser Pro Glu Tyr Ser Phe
                180                 185                 190
Arg Phe Asn Asp Asn Ser Met Asn Glu Phe Ile Gln Asp Pro Ala Leu
            195                 200                 205
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                    245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
    275                 280                 285
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
                340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Lys Lys Leu Lys Val Asn Phe
    370                 375                 380
Arg Gly Gln Asn Ala Asn Leu Asn Pro Lys Ile Ile Thr Pro Ile Lys
385                 390                 395                 400
Gly Arg Gly Leu Val Lys Lys Ile Ile Arg Phe Cys Val Arg Gly Ile
                405                 410                 415
Ile Thr Ser Leu Thr Phe Glu His Asn Trp Ala Gln Leu Thr Ser Lys
            420                 425                 430
Ser Leu Val Pro Arg Gly Ser Lys Ala Leu Asn Asp Leu Cys Ile Glu
        435                 440                 445
Ile Asn Asn Gly Glu Leu Phe Phe Val Ala Ser Glu Asn Ser Tyr Asn
        450                 455                 460
Asp Asp Asn Ile Asn Thr Pro Lys Glu Ile Asp Thr Val Thr Ser
465                 470                 475                 480
Asn Asn Asn Tyr Glu Asn Asp Leu Asp Gln Val Ile Leu Asn Phe Asn
                485                 490                 495
```

```
Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
530                 535                 540

Ala Gln Lys Val Pro Glu Gly Glu Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
            610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
            690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
            725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
            805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
            850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
            885                 890                 895

Asp Val Tyr Lys Tyr Pro Thr Asn Lys Asn Gln Phe Gly Ile Tyr Asn
            900                 905                 910
```

```
Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
            965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
            995                 1000                1005

Lys Trp Ile Phe Val Thr Ile Thr Asn Asp Arg Leu Gly Asp Ser
        1010                1015                1020

Lys Leu Tyr Ile Asn Gly Asn Leu Ile Asp Gln Lys Ser Ile Leu
        1025                1030                1035

Asn Leu Gly Asn Ile His Val Ser Asp Asn Ile Leu Phe Lys Ile
        1040                1045                1050

Val Asn Cys Ser Tyr Thr Arg Tyr Ile Gly Ile Arg Tyr Phe Asn
        1055                1060                1065

Ile Phe Asp Lys Glu Leu Asp Glu Thr Glu Ile Gln Thr Leu Tyr
        1070                1075                1080

Ser Asn Glu Pro Asn Thr Asn Ile Leu Lys Asp Phe Trp Gly Asn
        1085                1090                1095

Tyr Leu Leu Tyr Asp Lys Glu Tyr Tyr Leu Leu Asn Val Leu Lys
        1100                1105                1110

Pro Asn Asn Phe Ile Asp Arg Arg Lys Asp Ser Thr Leu Ser Ile
        1115                1120                1125

Asn Asn Ile Arg Ser Thr Ile Leu Leu Ala Asn Arg Leu Tyr Ser
        1130                1135                1140

Gly Ile Lys Val Lys Ile Gln Arg Val Asn Asn Ser Ser Thr Asn
        1145                1150                1155

Asp Asn Leu Val Arg Lys Asn Asp Gln Val Tyr Ile Asn Phe Val
        1160                1165                1170

Ala Ser Lys Thr His Leu Phe Pro Leu Tyr Ala Asp Thr Ala Thr
        1175                1180                1185

Thr Asn Lys Glu Lys Thr Ile Lys Ile Ser Ser Ser Gly Asn Arg
        1190                1195                1200

Phe Asn Gln Val Val Val Met Asn Ser Val Gly Asn Asn Cys Thr
        1205                1210                1215

Met Asn Phe Lys Asn Asn Asn Gly Asn Asn Ile Gly Leu Leu Gly
        1220                1225                1230

Phe Lys Ala Asp Thr Val Val Ala Ser Thr Trp Tyr Tyr Thr His
        1235                1240                1245

Met Arg Asp His Thr Asn Ser Asn Gly Cys Phe Trp Asn Phe Ile
        1250                1255                1260

Ser Glu Glu His Gly Trp Gln Glu Lys
        1265                1270

<210> SEQ ID NO 58
<211> LENGTH: 1272
<212> TYPE: PRT
<213> ORGANISM: Clostridium botulinum

<400> SEQUENCE: 58
```

-continued

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Lys Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65              70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Lys Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415
```

```
Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
            450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
            485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
            725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
            805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
```

```
           835                 840                 845
Ser Tyr Thr Asp Asp Lys Ile Leu Ile Ser Tyr Phe Asn Lys Phe Phe
850                 855                 860
Lys Arg Ile Lys Ser Ser Val Leu Asn Met Arg Tyr Lys Asn Asp
865                 870                 875                 880
Lys Tyr Val Asp Thr Ser Gly Tyr Asp Ser Asn Ile Asn Ile Asn Gly
                    885                 890                 895
Asp Val Tyr Lys Tyr Pro Thr Asn Lys Asn Gln Phe Gly Ile Tyr Asn
                    900                 905                 910
Asp Lys Leu Ser Glu Val Asn Ile Ser Gln Asn Asp Tyr Ile Ile Tyr
                    915                 920                 925
Asp Asn Lys Tyr Lys Asn Phe Ser Ile Ser Phe Trp Val Arg Ile Pro
930                 935                 940
Asn Tyr Asp Asn Lys Ile Val Asn Val Asn Asn Glu Tyr Thr Ile Ile
945                 950                 955                 960
Asn Cys Met Arg Asp Asn Asn Ser Gly Trp Lys Val Ser Leu Asn His
                    965                 970                 975
Asn Glu Ile Ile Trp Thr Leu Gln Asp Asn Ala Gly Ile Asn Gln Lys
                    980                 985                 990
Leu Ala Phe Asn Tyr Gly Asn Ala  Asn Gly Ile Ser Asp  Tyr Ile Asn
                    995                 1000                1005
Lys Trp  Ile Phe Val Thr Ile  Thr Asn Asp Arg Leu  Gly Asp Ser
1010                1015                1020
Lys Leu  Tyr Ile Asn Gly Asn  Leu Ile Asp Gln Lys  Ser Ile Leu
1025                1030                1035
Asn Leu  Gly Asn Ile His Val  Ser Asp Asn Ile Leu  Phe Lys Ile
1040                1045                1050
Val Asn  Cys Ser Tyr Thr Arg  Tyr Ile Gly Ile Arg  Tyr Phe Asn
1055                1060                1065
Ile Phe  Asp Lys Glu Leu Asp  Glu Thr Glu Ile Gln  Thr Leu Tyr
1070                1075                1080
Ser Asn  Glu Pro Asn Thr Asn  Ile Leu Lys Asp Phe  Trp Gly Asn
1085                1090                1095
Tyr Leu  Leu Tyr Asp Lys Glu  Tyr Tyr Leu Leu Asn  Val Leu Lys
1100                1105                1110
Pro Asn  Asn Phe Ile Asp Arg  Arg Lys Asp Ser Thr  Leu Ser Ile
1115                1120                1125
Asn Asn  Ile Arg Ser Thr Ile  Leu Leu Ala Asn Arg  Leu Tyr Ser
1130                1135                1140
Gly Ile  Lys Val Lys Ile Gln  Arg Val Asn Asn Ser  Ser Thr Asn
1145                1150                1155
Asp Asn  Leu Val Arg Lys Asn  Asp Gln Val Tyr Ile  Asn Phe Val
1160                1165                1170
Ala Ser  Lys Thr His Leu Phe  Pro Leu Tyr Ala Asp  Thr Ala Thr
1175                1180                1185
Thr Asn  Lys Glu Lys Thr Ile  Lys Ile Ser Ser Ser  Gly Asn Arg
1190                1195                1200
Phe Asn  Gln Val Val Val Met  Asn Ser Val Gly Asn  Asn Cys Thr
1205                1210                1215
Met Asn  Phe Lys Asn Asn Asn  Gly Asn Asn Ile Gly  Leu Leu Gly
1220                1225                1230
Phe Lys  Ala Asp Thr Val Val  Ala Ser Thr Trp Tyr  Tyr Thr His
1235                1240                1245
```

```
Met Arg Asp His Thr Asn Ser Asn Gly Cys Phe Trp Asn Phe Ile
    1250                1255                1260

Ser Glu Glu His Gly Trp Gln Glu Lys
    1265                1270
```

<210> SEQ ID NO 59
<211> LENGTH: 1272
<212> TYPE: PRT
<213> ORGANISM: Clostridium botulinum

<400> SEQUENCE: 59

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Lys Asp Phe His Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
    130                 135                 140

Leu Pro Asn Val Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
```

```
              340                 345                 350
Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Lys Leu Lys Val Asn Phe
        370                 375                 380

Arg Gly Gln Asn Ala Asn Leu Asn Pro Arg Ile Ile Thr Pro Ile Lys
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
    450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765
```

```
Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
    835                 840                 845

Ser Tyr Thr Asp Asp Lys Ile Leu Ile Ser Tyr Phe Asn Lys Phe Phe
    850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
    915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala Asn Gly Ile Ser Asp Tyr Ile Asn
                995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170
```

-continued

```
Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 60
<211> LENGTH: 1272
<212> TYPE: PRT
<213> ORGANISM: Clostridium botulinum

<400> SEQUENCE: 60

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Lys Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270
```

```
Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
            325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Asn Asn Leu Lys Val Asn Phe
            370                 375                 380

Arg Gly Gln Asn Ala Asn Leu Asn Pro Arg Ile Ile Thr Pro Ile Lys
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685
```

-continued

```
Asn Ala Leu Lys Glu Arg Asp Glu Lys Trp Lys Glu Val Tyr Ser Phe
    690             695             700

Ile Val Ser Asn Trp Met Thr Lys Ile Asn Thr Gln Phe Asn Lys Arg
705             710             715             720

Lys Glu Gln Met Tyr Gln Ala Leu Gln Asn Gln Val Asn Ala Ile Lys
                725             730             735

Thr Ile Ile Glu Ser Lys Tyr Asn Ser Tyr Thr Leu Glu Glu Lys Asn
            740             745             750

Glu Leu Thr Asn Lys Tyr Asp Ile Lys Gln Ile Glu Asn Glu Leu Asn
        755             760             765

Gln Lys Val Ser Ile Ala Met Asn Asn Ile Asp Arg Phe Leu Thr Glu
770             775             780

Ser Ser Ile Ser Tyr Leu Met Lys Leu Ile Asn Glu Val Lys Ile Asn
785             790             795             800

Lys Leu Arg Glu Tyr Asp Glu Asn Val Lys Thr Tyr Leu Leu Asn Tyr
                805             810             815

Ile Ile Gln His Gly Ser Ile Leu Gly Glu Ser Gln Asn Glu Leu Asn
            820             825             830

Ser Met Val Thr Asp Thr Leu Asn Asn Ser Ile Pro Phe Lys Leu Ser
        835             840             845

Ser Tyr Thr Asp Asp Lys Ile Leu Ile Ser Tyr Phe Asn Lys Phe Phe
850             855             860

Lys Arg Ile Lys Ser Ser Ser Val Leu Asn Met Arg Tyr Lys Asn Asp
865             870             875             880

Lys Tyr Val Asp Thr Ser Gly Tyr Asp Ser Asn Ile Asn Ile Asn Gly
                885             890             895

Asp Val Tyr Lys Tyr Pro Thr Asn Lys Asn Gln Phe Gly Ile Tyr Asn
            900             905             910

Asp Lys Leu Ser Glu Val Asn Ile Ser Gln Asn Asp Tyr Ile Ile Tyr
        915             920             925

Asp Asn Lys Tyr Lys Asn Phe Ser Ile Ser Phe Trp Val Arg Ile Pro
930             935             940

Asn Tyr Asp Asn Lys Ile Val Asn Val Asn Asn Glu Tyr Thr Ile Ile
945             950             955             960

Asn Cys Met Arg Asp Asn Asn Ser Gly Trp Lys Val Ser Leu Asn His
                965             970             975

Asn Glu Ile Ile Trp Thr Leu Gln Asp Asn Ala Gly Ile Asn Gln Lys
            980             985             990

Leu Ala Phe Asn Tyr Gly Asn Ala  Asn Gly Ile Ser Asp  Tyr Ile Asn
        995             1000             1005

Lys Trp  Ile Phe Val Thr Ile  Thr Asn Asp Arg Leu  Gly Asp Ser
    1010             1015             1020

Lys Leu  Tyr Ile Asn Gly Asn  Leu Ile Asp Gln Lys  Ser Ile Leu
    1025             1030             1035

Asn Leu  Gly Asn Ile His Val  Ser Asp Asn Ile Leu  Phe Lys Ile
    1040             1045             1050

Val Asn  Cys Ser Tyr Thr Arg  Tyr Ile Gly Ile Arg  Tyr Phe Asn
    1055             1060             1065

Ile Phe  Asp Lys Glu Leu Asp  Glu Thr Glu Ile Gln  Thr Leu Tyr
    1070             1075             1080

Ser Asn  Glu Pro Asn Thr Asn  Ile Leu Lys Asp Phe  Trp Gly Asn
    1085             1090             1095

Tyr Leu  Leu Tyr Asp Lys Glu  Tyr Tyr Leu Leu Asn  Val Leu Lys
```

```
                    1100                1105                1110
Pro  Asn  Asn  Phe  Ile  Asp  Arg  Arg  Lys  Asp  Ser  Thr  Leu  Ser  Ile
            1115                1120                1125

Asn  Asn  Ile  Arg  Ser  Thr  Ile  Leu  Leu  Ala  Asn  Arg  Leu  Tyr  Ser
       1130                1135                1140

Gly  Ile  Lys  Val  Lys  Ile  Gln  Arg  Val  Asn  Asn  Ser  Ser  Thr  Asn
  1145                1150                1155

Asp  Asn  Leu  Val  Arg  Lys  Asp  Gln  Val  Tyr  Ile  Asn  Phe  Val
       1160                1165                1170

Ala  Ser  Lys  Thr  His  Leu  Phe  Pro  Leu  Tyr  Ala  Asp  Thr  Ala  Thr
  1175                1180                1185

Thr  Asn  Lys  Glu  Lys  Thr  Ile  Lys  Ile  Ser  Ser  Ser  Gly  Asn  Arg
  1190                1195                1200

Phe  Asn  Gln  Val  Val  Val  Met  Asn  Ser  Val  Gly  Asn  Asn  Cys  Thr
  1205                1210                1215

Met  Asn  Phe  Lys  Asn  Asn  Gly  Asn  Asn  Ile  Gly  Leu  Leu  Gly
  1220                1225                1230

Phe  Lys  Ala  Asp  Thr  Val  Val  Ala  Ser  Thr  Trp  Tyr  Tyr  Thr  His
  1235                1240                1245

Met  Arg  Asp  His  Thr  Asn  Ser  Asn  Gly  Cys  Phe  Trp  Asn  Phe  Ile
  1250                1255                1260

Ser  Glu  Glu  His  Gly  Trp  Gln  Glu  Lys
  1265                1270

<210> SEQ ID NO 61
<211> LENGTH: 1272
<212> TYPE: PRT
<213> ORGANISM: Clostridium botulinum

<400> SEQUENCE: 61

Met  Pro  Lys  Ile  Asn  Ser  Phe  Asn  Tyr  Asn  Asp  Pro  Val  Asn  Asp  Arg
 1                   5                   10                  15

Thr  Ile  Leu  Tyr  Ile  Lys  Pro  Gly  Gly  Cys  Gln  Glu  Phe  Tyr  Lys  Ser
            20                  25                  30

Phe  Asn  Ile  Met  Lys  Asn  Ile  Trp  Ile  Ile  Pro  Glu  Arg  Asn  Val  Ile
        35                  40                  45

Gly  Thr  Thr  Pro  Gln  Asp  Phe  His  Pro  Pro  Thr  Ser  Leu  Lys  Asn  Gly
    50                  55                  60

Asp  Ser  Ser  Tyr  Tyr  Asp  Pro  Lys  Tyr  Leu  Gln  Ser  Asp  Glu  Glu  Lys
65                  70                  75                  80

Asp  Arg  Phe  Leu  Lys  Ile  Val  Thr  Lys  Ile  Phe  Asn  Arg  Ile  Asn  Asn
                85                  90                  95

Asn  Leu  Ser  Gly  Gly  Ile  Leu  Leu  Glu  Glu  Leu  Ser  Lys  Ala  Asn  Pro
            100                 105                 110

Tyr  Leu  Gly  Asn  Asp  Asn  Thr  Pro  Asp  Asn  Gln  Phe  His  Ile  Gly  Asp
        115                 120                 125

Ala  Ser  Ala  Val  Glu  Ile  Lys  Phe  Ser  Asn  Gly  Ser  Gln  Asp  Ile  Leu
    130                 135                 140

Leu  Pro  Asn  Val  Ile  Ile  Met  Gly  Ala  Glu  Pro  Asp  Leu  Phe  Glu  Thr
145                 150                 155                 160

Asn  Ser  Ser  Asn  Ile  Ser  Leu  Arg  Asn  Asn  Tyr  Met  Pro  Ser  Asn  His
                165                 170                 175

Gly  Phe  Gly  Ser  Ile  Ala  Ile  Val  Thr  Phe  Ser  Pro  Glu  Tyr  Ser  Phe
            180                 185                 190
```

-continued

```
Arg Phe Asn Asp Asn Ser Met Asn Glu Phe Ile Gln Asp Pro Ala Leu
            195                 200                 205
Thr Leu Met His Glu Leu Ile His Ser Leu His Gly Leu Tyr Gly Ala
210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
            245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
            325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Lys Lys Leu Lys Val Asn Phe
            370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Val Arg Gly Ile
            405                 410                 415
Ile Thr Ser Leu Thr Phe Glu His Asn Trp Ala Gln Leu Thr Ser Lys
            420                 425                 430
Ser Leu Val Pro Arg Gly Ser Lys Ala Leu Asn Asp Leu Cys Ile Glu
            435                 440                 445
Ile Asn Asn Gly Glu Leu Phe Phe Val Ala Ser Glu Asn Ser Tyr Asn
450                 455                 460
Asp Asp Asn Ile Asn Thr Pro Lys Glu Ile Asp Asp Thr Val Thr Ser
465                 470                 475                 480
Asn Asn Asn Tyr Glu Asn Asp Leu Asp Gln Val Ile Leu Asn Phe Asn
            485                 490                 495
Ser Glu Ser Ala Pro Gly Leu Ser Asp Glu Lys Leu Asn Leu Thr Ile
            500                 505                 510
Gln Asn Asp Ala Tyr Ile Pro Lys Tyr Asp Ser Asn Gly Thr Ser Asp
            515                 520                 525
Ile Glu Gln His Asp Val Asn Glu Leu Asn Val Phe Phe Tyr Leu Asp
            530                 535                 540
Ala Gln Lys Val Pro Glu Gly Asn Asn Val Asn Leu Thr Ser Ser
545                 550                 555                 560
Ile Asp Thr Ala Leu Leu Glu Gln Pro Lys Ile Tyr Thr Phe Phe Ser
            565                 570                 575
Ser Glu Phe Ile Asn Asn Val Asn Lys Pro Val Gln Ala Ala Leu Phe
            580                 585                 590
Val Ser Trp Ile Gln Gln Val Leu Val Asp Phe Thr Thr Glu Ala Asn
            595                 600                 605
Gln Lys Ser Thr Val Asp Lys Ile Ala Asp Ile Ser Ile Val Val Pro
```

-continued

```
            610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                    645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala  Asn Gly Ile Ser Asp Tyr Ile Asn
                995                 1000                1005

Lys Trp Ile Phe Val Thr Ile  Thr Asn Asp Arg Leu  Gly Asp Ser
    1010                1015                1020

Lys Leu Tyr Ile Asn Gly Asn  Leu Ile Asp Gln Lys  Ser Ile Leu
    1025                1030                1035
```

-continued

```
Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270
```

<210> SEQ ID NO 62
<211> LENGTH: 1272
<212> TYPE: PRT
<213> ORGANISM: Clostridium botulinum

<400> SEQUENCE: 62

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Lys Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
```

-continued

```
            115                 120                 125
Ala Ser Ala Val Glu Ile Lys Phe Ser Asn Gly Ser Gln Asp Ile Leu
130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                    165                 170                 175
Gly Phe Gly Ser Ile Ala Ile Val Thr Phe Ser Pro Glu Tyr Ser Phe
                180                 185                 190
Arg Phe Asn Asp Asn Ser Met Asn Glu Phe Ile Gln Asp Pro Ala Leu
            195                 200                 205
Thr Leu Met His Glu Leu Ile His Ser Leu His Gly Leu Tyr Gly Ala
210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
                260                 265                 270
Thr Asn Leu Leu Ala Asp Tyr Lys Lys Ile Ala Ser Lys Leu Ser Lys
            275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
                340                 345                 350
Gly Gln Tyr Lys Tyr Phe Lys Leu Ser Asn Leu Leu Asn Asp Ser Ile
            355                 360                 365
Tyr Asn Ile Ser Glu Gly Tyr Asn Ile Lys Lys Leu Lys Val Asn Phe
370                 375                 380
Arg Gly Gln Asn Ala Asn Leu Asn Pro Arg Ile Ile Thr Pro Ile Lys
385                 390                 395                 400
Gly Arg Gly Leu Val Lys Lys Ile Ile Arg Phe Cys Val Arg Gly Ile
                405                 410                 415
Ile Thr Ser Leu Thr Phe Glu His Asn Trp Ala Gln Leu Thr Ser Lys
                420                 425                 430
Ser Leu Val Pro Arg Gly Ser Lys Ala Leu Asn Asp Leu Cys Ile Glu
            435                 440                 445
Ile Asn Asn Gly Glu Leu Phe Phe Val Ala Ser Glu Asn Ser Tyr Asn
450                 455                 460
Asp Asp Asn Ile Asn Thr Pro Lys Glu Ile Asp Asp Thr Val Thr Ser
465                 470                 475                 480
Asn Asn Asn Tyr Glu Asn Asp Leu Asp Gln Val Ile Leu Asn Phe Asn
                485                 490                 495
Ser Glu Ser Ala Pro Gly Leu Ser Asp Glu Lys Leu Asn Leu Thr Ile
                500                 505                 510
Gln Asn Asp Ala Tyr Ile Pro Lys Tyr Asp Ser Asn Gly Thr Ser Asp
            515                 520                 525
Ile Glu Gln His Asp Val Asn Glu Leu Asn Val Phe Phe Tyr Leu Asp
530                 535                 540
```

```
Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960
```

-continued

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 63
<211> LENGTH: 1272
<212> TYPE: PRT
<213> ORGANISM: Clostridium botulinum

<400> SEQUENCE: 63

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

```
Gly Thr Thr Pro Gln Asp Phe His Pro Pro Thr Ser Leu Lys Asn Gly
    50                  55                  60

Asp Ser Ser Tyr Tyr Asp Pro Lys Tyr Leu Gln Ser Asp Glu Glu Lys
65                   70                  75                   80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
                100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Lys Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
450                 455                 460
```

-continued

Asp Asp Asn Ile Asn Thr Pro Lys Glu Ile Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
        610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly

```
                        885                 890                 895
Asp Val Tyr Lys Tyr Pro Thr Asn Lys Asn Gln Phe Gly Ile Tyr Asn
                    900                 905                 910
Asp Lys Leu Ser Glu Val Asn Ile Ser Gln Asn Asp Tyr Ile Ile Tyr
                    915                 920                 925
Asp Asn Lys Tyr Lys Asn Phe Ser Ile Ser Phe Trp Val Arg Ile Pro
                    930                 935                 940
Asn Tyr Asp Asn Lys Ile Val Asn Val Asn Asn Glu Tyr Thr Ile Ile
945                 950                 955                 960
Asn Cys Met Arg Asp Asn Asn Ser Gly Trp Lys Val Ser Leu Asn His
                    965                 970                 975
Asn Glu Ile Ile Trp Thr Leu Gln Asp Asn Ala Gly Ile Asn Gln Lys
                    980                 985                 990
Leu Ala Phe Asn Tyr Gly Asn Ala  Asn Gly Ile Ser Asp  Tyr Ile Asn
                    995                 1000                 1005
Lys Trp  Ile Phe Val Thr Ile  Thr Asn Asp Arg Leu  Gly Asp Ser
1010                 1015                 1020
Lys Leu  Tyr Ile Asn Gly Asn  Leu Ile Asp Gln Lys  Ser Ile Leu
                    1025                 1030                 1035
Asn Leu  Gly Asn Ile His Val  Ser Asp Asn Ile Leu  Phe Lys Ile
                    1040                 1045                 1050
Val Asn  Cys Ser Tyr Thr Arg  Tyr Ile Gly Ile Arg  Tyr Phe Asn
                    1055                 1060                 1065
Ile Phe  Asp Lys Glu Leu Asp  Glu Thr Glu Ile Gln  Thr Leu Tyr
                    1070                 1075                 1080
Ser Asn  Glu Pro Asn Thr Asn  Ile Leu Lys Asp Phe  Trp Gly Asn
                    1085                 1090                 1095
Tyr Leu  Leu Tyr Asp Lys Glu  Tyr Tyr Leu Leu Asn  Val Leu Lys
                    1100                 1105                 1110
Pro Asn  Asn Phe Ile Asp Arg  Arg Lys Asp Ser Thr  Leu Ser Ile
                    1115                 1120                 1125
Asn Asn  Ile Arg Ser Thr Ile  Leu Leu Ala Asn Arg  Leu Tyr Ser
                    1130                 1135                 1140
Gly Ile  Lys Val Lys Ile Gln  Arg Val Asn Asn Ser  Ser Thr Asn
                    1145                 1150                 1155
Asp Asn  Leu Val Arg Lys Asn  Asp Gln Val Tyr Ile  Asn Phe Val
                    1160                 1165                 1170
Ala Ser  Lys Thr His Leu Phe  Pro Leu Tyr Ala Asp  Thr Ala Thr
                    1175                 1180                 1185
Thr Asn  Lys Glu Lys Thr Ile  Lys Ile Ser Ser Ser  Gly Asn Arg
                    1190                 1195                 1200
Phe Asn  Gln Val Val Val Met  Asn Ser Val Gly Asn  Asn Cys Thr
                    1205                 1210                 1215
Met Asn  Phe Lys Asn Asn Asn  Gly Asn Asn Ile Gly  Leu Leu Gly
                    1220                 1225                 1230
Phe Lys  Ala Asp Thr Val Val  Ala Ser Thr Trp Tyr  Tyr Thr His
                    1235                 1240                 1245
Met Arg  Asp His Thr Asn Ser  Asn Gly Cys Phe Trp  Asn Phe Ile
                    1250                 1255                 1260
Ser Glu  Glu His Gly Trp Gln  Glu Lys
                    1265                 1270

<210> SEQ ID NO 64
```

<211> LENGTH: 1272
<212> TYPE: PRT
<213> ORGANISM: Clostridium botulinum

<400> SEQUENCE: 64

```
Met Pro Lys Ile Asn Ser Phe Asn Tyr Asn Asp Pro Val Asn Asp Arg
1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Lys Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
    370                 375                 380

Arg Gly Gln Asn Ala Asn Leu Asn Pro Lys Ile Ile Thr Pro Ile Lys
```

```
                385                 390                 395                 400

Gly Arg Gly Leu Val Lys Lys Ile Ile Arg Phe Cys Val Arg Gly Ile
                            405                 410                 415

Ile Thr Ser Leu Thr Phe Glu His Asn Trp Ala Gln Leu Thr Ser Lys
                            420                 425                 430

Ser Leu Val Pro Arg Gly Ser Lys Ala Leu Asn Asp Leu Cys Ile Glu
                            435                 440                 445

Ile Asn Asn Gly Glu Leu Phe Phe Val Ala Ser Glu Asn Ser Tyr Asn
                    450                 455                 460

Asp Asp Asn Ile Asn Thr Pro Lys Glu Ile Asp Thr Val Thr Ser
        465                 470                 475                 480

Asn Asn Asn Tyr Glu Asn Asp Leu Asp Gln Val Ile Leu Asn Phe Asn
                            485                 490                 495

Ser Glu Ser Ala Pro Gly Leu Ser Asp Glu Lys Leu Asn Leu Thr Ile
                        500                 505                 510

Gln Asn Asp Ala Tyr Ile Pro Lys Tyr Asp Ser Asn Gly Thr Ser Asp
                    515                 520                 525

Ile Glu Gln His Asp Val Asn Glu Leu Asn Val Phe Phe Tyr Leu Asp
                    530                 535                 540

Ala Gln Lys Val Pro Glu Gly Glu Asn Asn Val Asn Leu Thr Ser Ser
        545                 550                 555                 560

Ile Asp Thr Ala Leu Leu Glu Gln Pro Lys Ile Tyr Thr Phe Phe Ser
                            565                 570                 575

Ser Glu Phe Ile Asn Asn Val Asn Lys Pro Val Gln Ala Ala Leu Phe
                        580                 585                 590

Val Ser Trp Ile Gln Gln Val Leu Val Asp Phe Thr Thr Glu Ala Asn
                    595                 600                 605

Gln Lys Ser Thr Val Asp Lys Ile Ala Asp Ile Ser Ile Val Val Pro
        610                 615                 620

Tyr Ile Gly Leu Ala Leu Asn Ile Gly Asn Glu Ala Gln Lys Gly Asn
        625                 630                 635                 640

Phe Lys Asp Ala Leu Glu Leu Leu Gly Ala Gly Ile Leu Leu Glu Phe
                            645                 650                 655

Glu Pro Glu Leu Leu Ile Pro Thr Ile Leu Val Phe Thr Ile Lys Ser
                        660                 665                 670

Phe Leu Gly Ser Ser Asp Asn Lys Asn Lys Val Ile Lys Ala Ile Asn
                    675                 680                 685

Asn Ala Leu Lys Glu Arg Asp Glu Lys Trp Lys Glu Val Tyr Ser Phe
                    690                 695                 700

Ile Val Ser Asn Trp Met Thr Lys Ile Asn Thr Gln Phe Asn Lys Arg
        705                 710                 715                 720

Lys Glu Gln Met Tyr Gln Ala Leu Gln Asn Val Asn Ala Ile Lys
                            725                 730                 735

Thr Ile Ile Glu Ser Lys Tyr Asn Ser Tyr Thr Leu Glu Glu Lys Asn
                        740                 745                 750

Glu Leu Thr Asn Lys Tyr Asp Ile Lys Gln Ile Glu Asn Glu Leu Asn
                    755                 760                 765

Gln Lys Val Ser Ile Ala Met Asn Asn Ile Asp Arg Phe Leu Thr Glu
                    770                 775                 780

Ser Ser Ile Ser Tyr Leu Met Lys Leu Ile Asn Glu Val Lys Ile Asn
        785                 790                 795                 800

Lys Leu Arg Glu Tyr Asp Glu Asn Val Lys Thr Tyr Leu Leu Asn Tyr
                            805                 810                 815
```

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
        850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
        900                 905                 910

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
        930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
            995                1000                1005

Lys Trp Ile Phe Val Thr Ile Thr Asn Asp Arg Leu Gly Asp Ser
       1010                1015                1020

Lys Leu Tyr Ile Asn Gly Asn Leu Ile Asp Gln Lys Ser Ile Leu
       1025                1030                1035

Asn Leu Gly Asn Ile His Val Ser Asp Asn Ile Leu Phe Lys Ile
       1040                1045                1050

Val Asn Cys Ser Tyr Thr Arg Tyr Ile Gly Ile Arg Tyr Phe Asn
       1055                1060                1065

Ile Phe Asp Lys Glu Leu Asp Glu Thr Glu Ile Gln Thr Leu Tyr
       1070                1075                1080

Ser Asn Glu Pro Asn Thr Asn Ile Leu Lys Asp Phe Trp Gly Asn
       1085                1090                1095

Tyr Leu Leu Tyr Asp Lys Glu Tyr Tyr Leu Leu Asn Val Leu Lys
       1100                1105                1110

Pro Asn Asn Phe Ile Asp Arg Arg Lys Asp Ser Thr Leu Ser Ile
       1115                1120                1125

Asn Asn Ile Arg Ser Thr Ile Leu Leu Ala Asn Arg Leu Tyr Ser
       1130                1135                1140

Gly Ile Lys Val Lys Ile Gln Arg Val Asn Asn Ser Ser Thr Asn
       1145                1150                1155

Asp Asn Leu Val Arg Lys Asn Asp Gln Val Tyr Ile Asn Phe Val
       1160                1165                1170

Ala Ser Lys Thr His Leu Phe Pro Leu Tyr Ala Asp Thr Ala Thr
       1175                1180                1185

Thr Asn Lys Glu Lys Thr Ile Lys Ile Ser Ser Ser Gly Asn Arg
       1190                1195                1200

Phe Asn Gln Val Val Val Met Asn Ser Val Gly Asn Asn Cys Thr
       1205                1210                1215

-continued

```
Met Asn Phe Lys Asn Asn Asn Gly Asn Asn Ile Gly Leu Leu Gly
1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 65
<211> LENGTH: 1272
<212> TYPE: PRT
<213> ORGANISM: Clostridium botulinum

<400> SEQUENCE: 65

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320
```

-continued

```
Ile Asn Lys Phe Asn Asp Ile Phe Lys Lys Leu Tyr Ser Phe Thr Glu
            325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Asn Leu Lys Val Asn Phe
        370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
            405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
        450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
            485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
        610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
        690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
            725                 730                 735
```

-continued

```
Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
        850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser
        1010                1015                1020

Lys Leu Tyr Ile Asn Gly Asn Leu Ile Asp Gln Lys Ser Ile Leu
        1025                1030                1035

Asn Leu Gly Asn Ile His Val Ser Asp Asn Ile Leu Phe Lys Ile
        1040                1045                1050

Val Asn Cys Ser Tyr Thr Arg Tyr Ile Gly Ile Arg Tyr Phe Asn
        1055                1060                1065

Ile Phe Asp Lys Glu Leu Asp Glu Thr Glu Ile Gln Thr Leu Tyr
        1070                1075                1080

Ser Asn Glu Pro Asn Thr Asn Ile Leu Lys Asp Phe Trp Gly Asn
        1085                1090                1095

Tyr Leu Leu Tyr Asp Lys Glu Tyr Tyr Leu Leu Asn Val Leu Lys
        1100                1105                1110

Pro Asn Asn Phe Ile Asp Arg Arg Lys Asp Ser Thr Leu Ser Ile
        1115                1120                1125

Asn Asn Ile Arg Ser Thr Ile Leu Leu Ala Asn Arg Leu Tyr Ser
        1130                1135                1140

Gly Ile Lys Val Lys Ile Gln Arg Val Asn Asn Ser Ser Thr Asn
```

```
                    1145                1150                1155

Asp  Asn  Leu  Val  Arg  Lys  Asn  Asp  Gln  Val  Tyr  Ile  Asn  Phe  Val
         1160                1165                1170

Ala  Ser  Lys  Thr  His  Leu  Phe  Pro  Leu  Tyr  Ala  Asp  Thr  Ala  Thr
         1175                1180                1185

Thr  Asn  Lys  Glu  Lys  Thr  Ile  Lys  Ile  Ser  Ser  Ser  Gly  Asn  Arg
         1190                1195                1200

Phe  Asn  Gln  Val  Val  Val  Met  Asn  Ser  Val  Gly  Asn  Asn  Cys  Thr
         1205                1210                1215

Met  Asn  Phe  Lys  Asn  Asn  Gly  Asn  Asn  Ile  Gly  Leu  Leu  Gly
         1220                1225                1230

Phe  Lys  Ala  Asp  Thr  Val  Val  Ala  Ser  Thr  Trp  Tyr  Tyr  Thr  His
         1235                1240                1245

Met  Arg  Asp  His  Thr  Asn  Ser  Asn  Gly  Cys  Phe  Trp  Asn  Phe  Ile
         1250                1255                1260

Ser  Glu  Glu  His  Gly  Trp  Gln  Glu  Lys
         1265                1270

<210> SEQ ID NO 66
<211> LENGTH: 1272
<212> TYPE: PRT
<213> ORGANISM: Clostridium botulinum

<400> SEQUENCE: 66

Met  Pro  Lys  Ile  Asn  Ser  Phe  Asn  Tyr  Asn  Asp  Pro  Val  Asn  Asp  Arg
1              5                  10                 15

Thr  Ile  Leu  Tyr  Ile  Lys  Pro  Gly  Gly  Cys  Gln  Glu  Phe  Tyr  Lys  Ser
                20                 25                 30

Phe  Asn  Ile  Met  Lys  Asn  Ile  Trp  Ile  Ile  Pro  Glu  Arg  Asn  Val  Ile
                35                 40                 45

Gly  Thr  Thr  Pro  Gln  Asp  Phe  His  Pro  Pro  Thr  Ser  Leu  Lys  Asn  Gly
       50                  55                 60

Asp  Ser  Ser  Tyr  Tyr  Asp  Pro  Asn  Tyr  Leu  Gln  Ser  Asp  Glu  Glu  Lys
65                  70                 75                 80

Asp  Arg  Phe  Leu  Lys  Ile  Val  Thr  Lys  Ile  Phe  Asn  Arg  Ile  Asn  Asn
                85                 90                 95

Asn  Leu  Ser  Gly  Gly  Ile  Leu  Leu  Glu  Glu  Leu  Ser  Lys  Ala  Asn  Pro
            100                 105                110

Tyr  Leu  Gly  Asn  Asp  Asn  Thr  Pro  Asp  Asn  Gln  Phe  His  Ile  Gly  Asp
            115                 120                125

Ala  Ser  Ala  Val  Glu  Ile  Lys  Phe  Ser  Asn  Gly  Ser  Gln  Asp  Ile  Leu
       130                 135                140

Leu  Pro  Asn  Val  Ile  Ile  Met  Gly  Ala  Glu  Pro  Asp  Leu  Phe  Glu  Thr
145                 150                 155                160

Asn  Ser  Ser  Asn  Ile  Ser  Leu  Arg  Asn  Asn  Tyr  Met  Pro  Ser  Asn  His
                165                170                 175

Gly  Phe  Gly  Ser  Ile  Ala  Ile  Val  Thr  Phe  Ser  Pro  Glu  Tyr  Ser  Phe
            180                 185                190

Arg  Phe  Asn  Asp  Asn  Ser  Met  Asn  Glu  Phe  Ile  Gln  Asp  Pro  Ala  Leu
            195                 200                205

Thr  Leu  Met  His  Glu  Leu  Ile  His  Ser  Leu  His  Gly  Leu  Tyr  Gly  Ala
       210                 215                 220

Lys  Gly  Ile  Thr  Thr  Lys  Tyr  Thr  Ile  Thr  Gln  Lys  Gln  Asn  Pro  Leu
225                 230                 235                240
```

```
Ile Thr Asn Ile Arg Gly Thr Asn Ile Glu Glu Phe Leu Thr Phe Gly
            245                 250                 255

Gly Thr Asp Leu Asn Ile Ile Thr Ser Ala Gln Ser Asn Asp Ile Tyr
        260                 265                 270

Thr Asn Leu Leu Ala Asp Tyr Lys Lys Ile Ala Ser Lys Leu Ser Lys
    275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Lys Lys Leu Lys Val Asn Phe
    370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
    450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
    530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
```

```
                    660                 665                 670
Phe Leu Gly Ser Ser Asp Asn Lys Asn Lys Val Ile Lys Ala Ile Asn
                675                 680                 685
Asn Ala Leu Lys Glu Arg Asp Glu Lys Trp Lys Glu Val Tyr Ser Phe
            690                 695                 700
Ile Val Ser Asn Trp Met Thr Lys Ile Asn Thr Gln Phe Asn Lys Arg
705                 710                 715                 720
Lys Glu Gln Met Tyr Gln Ala Leu Gln Asn Gln Val Asn Ala Ile Lys
                725                 730                 735
Thr Ile Ile Glu Ser Lys Tyr Asn Ser Tyr Thr Leu Glu Glu Lys Asn
                740                 745                 750
Glu Leu Thr Asn Lys Tyr Asp Ile Lys Gln Ile Glu Asn Glu Leu Asn
            755                 760                 765
Gln Lys Val Ser Ile Ala Met Asn Asn Ile Asp Arg Phe Leu Thr Glu
            770                 775                 780
Ser Ser Ile Ser Tyr Leu Met Lys Leu Ile Asn Glu Val Lys Ile Asn
785                 790                 795                 800
Lys Leu Arg Glu Tyr Asp Glu Asn Val Lys Thr Tyr Leu Leu Asn Tyr
                805                 810                 815
Ile Ile Gln His Gly Ser Ile Leu Gly Glu Ser Gln Gln Glu Leu Asn
                820                 825                 830
Ser Met Val Thr Asp Thr Leu Asn Asn Ser Ile Pro Phe Lys Leu Ser
            835                 840                 845
Ser Tyr Thr Asp Asp Lys Ile Leu Ile Ser Tyr Phe Asn Lys Phe Phe
            850                 855                 860
Lys Arg Ile Lys Ser Ser Ser Val Leu Asn Met Arg Tyr Lys Asn Asp
865                 870                 875                 880
Lys Tyr Val Asp Thr Ser Gly Tyr Asp Ser Asn Ile Asn Ile Asn Gly
                885                 890                 895
Asp Val Tyr Lys Tyr Pro Thr Asn Lys Asn Gln Phe Gly Ile Tyr Asn
                900                 905                 910
Asp Lys Leu Ser Glu Val Asn Ile Ser Gln Asn Asp Tyr Ile Ile Tyr
            915                 920                 925
Asp Asn Lys Tyr Lys Asn Phe Ser Ile Ser Phe Trp Val Arg Ile Pro
            930                 935                 940
Asn Tyr Asp Asn Lys Ile Val Asn Val Asn Asn Glu Tyr Thr Ile Ile
945                 950                 955                 960
Asn Cys Met Arg Asp Asn Asn Ser Gly Trp Lys Val Ser Leu Asn His
                965                 970                 975
Asn Glu Ile Ile Trp Thr Leu Gln Asp Asn Ala Gly Ile Asn Gln Lys
            980                 985                 990
Leu Ala Phe Asn Tyr Gly Asn Ala  Asn Gly Ile Ser Asp Tyr Ile Asn
            995                 1000                1005
Lys Trp Ile Phe Val Thr Ile Thr Asn Asp Arg Leu Gly Asp Ser
        1010                1015                1020
Lys Leu Tyr Ile Asn Gly Asn Leu Ile Asp Gln Lys Ser Ile Leu
        1025                1030                1035
Asn Leu Gly Asn Ile His Val Ser Asp Asn Ile Leu Phe Lys Ile
        1040                1045                1050
Val Asn Cys Ser Tyr Thr Arg Tyr Ile Gly Ile Arg Tyr Phe Asn
        1055                1060                1065
Ile Phe Asp Lys Glu Leu Asp Glu Thr Glu Ile Gln Thr Leu Tyr
        1070                1075                1080
```

-continued

```
Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
        1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270
```

<210> SEQ ID NO 67
<211> LENGTH: 1272
<212> TYPE: PRT
<213> ORGANISM: Clostridium botulinum

<400> SEQUENCE: 67

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
```

```
                165                 170                 175
Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
            245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
            290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
            325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Lys Leu Lys Lys Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
            405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
            485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590
```

-continued

```
Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
            610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
            850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
            930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala  Asn Gly Ile Ser Asp Tyr Ile Asn
            995                 1000                1005
```

Lys Trp Ile Phe Val Thr Ile Thr Asn Asp Arg Leu Gly Asp Ser
1010                1015                1020

Lys Leu Tyr Ile Asn Gly Asn Leu Ile Asp Gln Lys Ser Ile Leu
1025                1030                1035

Asn Leu Gly Asn Ile His Val Ser Asp Asn Ile Leu Phe Lys Ile
1040                1045                1050

Val Asn Cys Ser Tyr Thr Arg Tyr Ile Gly Ile Arg Tyr Phe Asn
1055                1060                1065

Ile Phe Asp Lys Glu Leu Asp Glu Thr Glu Ile Gln Thr Leu Tyr
1070                1075                1080

Ser Asn Glu Pro Asn Thr Asn Ile Leu Lys Asp Phe Trp Gly Asn
1085                1090                1095

Tyr Leu Leu Tyr Asp Lys Glu Tyr Tyr Leu Leu Asn Val Leu Lys
1100                1105                1110

Pro Asn Asn Phe Ile Asp Arg Arg Lys Asp Ser Thr Leu Ser Ile
1115                1120                1125

Asn Asn Ile Arg Ser Thr Ile Leu Leu Ala Asn Arg Leu Tyr Ser
1130                1135                1140

Gly Ile Lys Val Lys Ile Gln Arg Val Asn Asn Ser Ser Thr Asn
1145                1150                1155

Asp Asn Leu Val Arg Lys Asn Asp Gln Val Tyr Ile Asn Phe Val
1160                1165                1170

Ala Ser Lys Thr His Leu Phe Pro Leu Tyr Ala Asp Thr Ala Thr
1175                1180                1185

Thr Asn Lys Glu Lys Thr Ile Lys Ile Ser Ser Ser Gly Asn Arg
1190                1195                1200

Phe Asn Gln Val Val Val Met Asn Ser Val Gly Asn Asn Cys Thr
1205                1210                1215

Met Asn Phe Lys Asn Asn Asn Gly Asn Asn Ile Gly Leu Leu Gly
1220                1225                1230

Phe Lys Ala Asp Thr Val Val Ala Ser Thr Trp Tyr Tyr Thr His
1235                1240                1245

Met Arg Asp His Thr Asn Ser Asn Gly Cys Phe Trp Asn Phe Ile
1250                1255                1260

Ser Glu Glu His Gly Trp Gln Glu Lys
1265                1270

<210> SEQ ID NO 68
<211> LENGTH: 1272
<212> TYPE: PRT
<213> ORGANISM: Clostridium botulinum

<400> SEQUENCE: 68

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

```
Asn Leu Ser Gly Gly Ile Leu Glu Glu Leu Ser Lys Ala Asn Pro
            100                 105                 110
Tyr Leu Gly Asn Asp Asn Thr Pro Asp Asn Gln Phe His Ile Gly Asp
        115                 120                 125
Ala Ser Ala Val Glu Ile Lys Phe Ser Asn Gly Ser Gln Asp Ile Leu
    130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
            180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Lys Lys Leu Lys Lys Lys Phe
    370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Val Arg Gly Ile
                405                 410                 415
Ile Thr Ser Leu Thr Phe Glu His Asn Trp Ala Gln Leu Thr Ser Lys
            420                 425                 430
Ser Leu Val Pro Arg Gly Ser Lys Ala Leu Asn Asp Leu Cys Ile Glu
        435                 440                 445
Ile Asn Asn Gly Glu Leu Phe Phe Val Ala Ser Glu Asn Ser Tyr Asn
    450                 455                 460
Asp Asp Asn Ile Asn Thr Pro Lys Glu Ile Asp Asp Thr Val Thr Ser
465                 470                 475                 480
Asn Asn Asn Tyr Glu Asn Asp Leu Asp Gln Val Ile Leu Asn Phe Asn
                485                 490                 495
Ser Glu Ser Ala Pro Gly Leu Ser Asp Glu Lys Leu Asn Leu Thr Ile
            500                 505                 510
```

```
Gln Asn Asp Ala Tyr Ile Pro Lys Tyr Asp Ser Asn Gly Thr Ser Asp
            515                 520                 525
Ile Glu Gln His Asp Val Asn Glu Leu Asn Val Phe Phe Tyr Leu Asp
530                 535                 540
Ala Gln Lys Val Pro Glu Gly Glu Asn Val Asn Leu Thr Ser Ser
545                 550                 555                 560
Ile Asp Thr Ala Leu Leu Glu Gln Pro Lys Ile Tyr Thr Phe Phe Ser
                565                 570                 575
Ser Glu Phe Ile Asn Asn Val Asn Lys Pro Val Gln Ala Ala Leu Phe
            580                 585                 590
Val Ser Trp Ile Gln Gln Val Leu Val Asp Phe Thr Thr Glu Ala Asn
        595                 600                 605
Gln Lys Ser Thr Val Asp Lys Ile Ala Asp Ile Ser Ile Val Val Pro
    610                 615                 620
Tyr Ile Gly Leu Ala Leu Asn Ile Gly Asn Glu Ala Gln Lys Gly Asn
625                 630                 635                 640
Phe Lys Asp Ala Leu Glu Leu Leu Gly Ala Gly Ile Leu Leu Glu Phe
                645                 650                 655
Glu Pro Glu Leu Leu Ile Pro Thr Ile Leu Val Phe Thr Ile Lys Ser
            660                 665                 670
Phe Leu Gly Ser Ser Asp Asn Lys Asn Lys Val Ile Lys Ala Ile Asn
        675                 680                 685
Asn Ala Leu Lys Glu Arg Asp Glu Lys Trp Lys Glu Val Tyr Ser Phe
    690                 695                 700
Ile Val Ser Asn Trp Met Thr Lys Ile Asn Thr Gln Phe Asn Lys Arg
705                 710                 715                 720
Lys Glu Gln Met Tyr Gln Ala Leu Gln Asn Gln Val Asn Ala Ile Lys
                725                 730                 735
Thr Ile Ile Glu Ser Lys Tyr Asn Ser Tyr Thr Leu Glu Glu Lys Asn
            740                 745                 750
Glu Leu Thr Asn Lys Tyr Asp Ile Lys Gln Ile Glu Asn Glu Leu Asn
        755                 760                 765
Gln Lys Val Ser Ile Ala Met Asn Asn Ile Asp Arg Phe Leu Thr Glu
    770                 775                 780
Ser Ser Ile Ser Tyr Leu Met Lys Leu Ile Asn Glu Val Lys Ile Asn
785                 790                 795                 800
Lys Leu Arg Glu Tyr Asp Glu Asn Val Lys Thr Tyr Leu Leu Asn Tyr
                805                 810                 815
Ile Ile Gln His Gly Ser Ile Leu Gly Glu Ser Gln Gln Glu Leu Asn
            820                 825                 830
Ser Met Val Thr Asp Thr Leu Asn Asn Ser Ile Pro Phe Lys Leu Ser
        835                 840                 845
Ser Tyr Thr Asp Asp Lys Ile Leu Ile Ser Tyr Phe Asn Lys Phe Phe
    850                 855                 860
Lys Arg Ile Lys Ser Ser Val Leu Asn Met Arg Tyr Lys Asn Asp
865                 870                 875                 880
Lys Tyr Val Asp Thr Ser Gly Tyr Asp Ser Asn Ile Asn Ile Asn Gly
                885                 890                 895
Asp Val Tyr Lys Tyr Pro Thr Asn Lys Asn Gln Phe Gly Ile Tyr Asn
            900                 905                 910
Asp Lys Leu Ser Glu Val Asn Ile Ser Gln Asn Asp Tyr Ile Ile Tyr
        915                 920                 925
Asp Asn Lys Tyr Lys Asn Phe Ser Ile Ser Phe Trp Val Arg Ile Pro
```

```
                930                 935                 940
Asn Tyr Asp Asn Lys Ile Val Asn Val Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 69
<211> LENGTH: 1272
<212> TYPE: PRT
<213> ORGANISM: Clostridium botulinum

<400> SEQUENCE: 69

Met Pro Lys Ile Asn Ser Phe Asn Tyr Asn Asp Pro Val Asn Asp Arg
1               5                   10                  15
```

```
Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Lys Lys Leu Lys Lys Lys Phe
    370                 375                 380

Arg Gly Gln Asn Ala Asn Lys Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
```

```
            435                 440                 445
Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Thr Val Thr Ser
465                 470                 475             480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
                675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
850                 855                 860
```

-continued

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
            930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala Asn Gly Ile Ser Asp Tyr Ile Asn
            995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 70
<211> LENGTH: 1272
<212> TYPE: PRT
<213> ORGANISM: Clostridium botulinum

<400> SEQUENCE: 70

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
        340                 345                 350

Gly Gln Tyr Lys Tyr Phe Lys Leu Ser Asn Leu Leu Asn Asp Ser Ile
    355                 360                 365

```
Tyr Asn Ile Ser Glu Gly Tyr Asn Ile Lys Lys Leu Lys Lys Asn Phe
        370                 375                 380

Arg Gly Gln Asn Ala Asn Lys Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
770                 775                 780
```

```
Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
        995                 1000                1005

Lys Trp Ile Phe Val Thr Ile Thr Asn Asp Arg Leu Gly Asp Ser
    1010                1015                1020

Lys Leu Tyr Ile Asn Gly Asn Leu Ile Asp Gln Lys Ser Ile Leu
    1025                1030                1035

Asn Leu Gly Asn Ile His Val Ser Asp Asn Ile Leu Phe Lys Ile
    1040                1045                1050

Val Asn Cys Ser Tyr Thr Arg Tyr Ile Gly Ile Arg Tyr Phe Asn
    1055                1060                1065

Ile Phe Asp Lys Glu Leu Asp Glu Thr Glu Ile Gln Thr Leu Tyr
    1070                1075                1080

Ser Asn Glu Pro Asn Thr Asn Ile Leu Lys Asp Phe Trp Gly Asn
    1085                1090                1095

Tyr Leu Leu Tyr Asp Lys Glu Tyr Tyr Leu Leu Asn Val Leu Lys
    1100                1105                1110

Pro Asn Asn Phe Ile Asp Arg Arg Lys Asp Ser Thr Leu Ser Ile
    1115                1120                1125

Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asn Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
```

```
                1190                1195                1200
Phe Asn Gln Val Val Met Asn Ser Val Gly Asn Asn Cys Thr
    1205                1210                1215
Met Asn Phe Lys Asn Asn Asn Gly Asn Ile Gly Leu Leu Gly
    1220                1225                1230
Phe Lys Ala Asp Thr Val Val Ala Ser Thr Trp Tyr Tyr Thr His
    1235                1240                1245
Met Arg Asp His Thr Asn Ser Asn Gly Cys Phe Trp Asn Phe Ile
    1250                1255                1260
Ser Glu Glu His Gly Trp Gln Glu Lys
    1265                1270

<210> SEQ ID NO 71
<211> LENGTH: 1272
<212> TYPE: PRT
<213> ORGANISM: Clostridium botulinum

<400> SEQUENCE: 71

Met Pro Lys Ile Asn Ser Phe Asn Tyr Asn Asp Pro Val Asn Asp Arg
1               5                   10                  15
Thr Ile Leu Tyr Ile Lys Pro Gly Gly Cys Gln Glu Phe Tyr Lys Ser
            20                  25                  30
Phe Asn Ile Met Lys Asn Ile Trp Ile Ile Pro Glu Arg Asn Val Ile
        35                  40                  45
Gly Thr Thr Pro Gln Asp Phe His Pro Pro Thr Ser Leu Lys Asn Gly
    50                  55                  60
Asp Ser Ser Tyr Tyr Asp Pro Asn Tyr Leu Gln Ser Asp Glu Glu Lys
65                  70                  75                  80
Asp Arg Phe Leu Lys Ile Val Thr Lys Ile Phe Asn Arg Ile Asn Asn
                85                  90                  95
Asn Leu Ser Gly Gly Ile Leu Leu Glu Glu Leu Ser Lys Ala Asn Pro
            100                 105                 110
Tyr Leu Gly Asn Asp Asn Thr Pro Asp Asn Gln Phe His Ile Gly Asp
        115                 120                 125
Ala Ser Ala Val Glu Ile Lys Phe Ser Asn Gly Ser Gln Asp Ile Leu
    130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
                165                 170                 175
Gly Phe Gly Ser Ile Ala Ile Val Thr Phe Ser Pro Glu Tyr Ser Phe
            180                 185                 190
Arg Phe Asn Asp Asn Ser Met Asn Glu Phe Ile Gln Asp Pro Ala Leu
        195                 200                 205
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
                245                 250                 255
Gly Thr Asp Leu Asn Ile Ile Thr Ser Ala Gln Ser Asn Asp Ile Tyr
            260                 265                 270
Thr Asn Leu Leu Ala Asp Tyr Lys Lys Ile Ala Ser Lys Leu Ser Lys
        275                 280                 285
```

```
Val Gln Val Ser Asn Pro Leu Leu Asn Pro Tyr Lys Asp Val Phe Glu
    290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
                    325                 330                 335
Phe Asp Leu Ala Thr Lys Phe Gln Val Lys Cys Arg Gln Thr Tyr Ile
            340                 345                 350
Gly Gln Tyr Lys Tyr Phe Lys Leu Ser Asn Leu Leu Asn Asp Ser Ile
        355                 360                 365
Tyr Asn Ile Ser Glu Gly Tyr Asn Ile Lys Lys Leu Lys Val Lys Phe
370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Val Arg Gly Ile
                    405                 410                 415
Ile Thr Ser Leu Thr Phe Glu His Asn Trp Ala Gln Leu Thr Ser Lys
            420                 425                 430
Ser Leu Val Pro Arg Gly Ser Lys Ala Leu Asn Asp Leu Cys Ile Glu
        435                 440                 445
Ile Asn Asn Gly Glu Leu Phe Phe Val Ala Ser Glu Asn Ser Tyr Asn
450                 455                 460
Asp Asp Asn Ile Asn Thr Pro Lys Glu Ile Asp Asp Thr Val Thr Ser
465                 470                 475                 480
Asn Asn Asn Tyr Glu Asn Asp Leu Asp Gln Val Ile Leu Asn Phe Asn
                    485                 490                 495
Ser Glu Ser Ala Pro Gly Leu Ser Asp Glu Lys Leu Asn Leu Thr Ile
            500                 505                 510
Gln Asn Asp Ala Tyr Ile Pro Lys Tyr Asp Ser Asn Gly Thr Ser Asp
        515                 520                 525
Ile Glu Gln His Asp Val Asn Glu Leu Asn Val Phe Phe Tyr Leu Asp
530                 535                 540
Ala Gln Lys Val Pro Glu Gly Glu Asn Asn Val Asn Leu Thr Ser Ser
545                 550                 555                 560
Ile Asp Thr Ala Leu Leu Glu Gln Pro Lys Ile Tyr Thr Phe Phe Ser
                    565                 570                 575
Ser Glu Phe Ile Asn Asn Val Asn Lys Pro Val Gln Ala Ala Leu Phe
            580                 585                 590
Val Ser Trp Ile Gln Gln Val Leu Val Asp Phe Thr Thr Glu Ala Asn
        595                 600                 605
Gln Lys Ser Thr Val Asp Lys Ile Ala Asp Ile Ser Ile Val Val Pro
610                 615                 620
Tyr Ile Gly Leu Ala Leu Asn Ile Gly Asn Glu Ala Gln Lys Gly Asn
625                 630                 635                 640
Phe Lys Asp Ala Leu Glu Leu Leu Gly Ala Gly Ile Leu Leu Glu Phe
                    645                 650                 655
Glu Pro Glu Leu Leu Ile Pro Thr Ile Leu Val Phe Thr Ile Lys Ser
            660                 665                 670
Phe Leu Gly Ser Ser Asp Asn Lys Asn Lys Val Ile Lys Ala Ile Asn
        675                 680                 685
Asn Ala Leu Lys Glu Arg Asp Glu Lys Trp Lys Glu Val Tyr Ser Phe
690                 695                 700
Ile Val Ser Asn Trp Met Thr Lys Ile Asn Thr Gln Phe Asn Lys Arg
```

```
           705                 710                 715                 720
Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
                755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
                820                 825                 830

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
                850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
                930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala Asn Gly Ile Ser Asp Tyr Ile Asn
                995                1000                1005

Lys Trp Ile Phe Val Thr Ile Thr Asn Asp Arg Leu Gly Asp Ser
            1010                1015                1020

Lys Leu Tyr Ile Asn Gly Asn Leu Ile Asp Gln Lys Ser Ile Leu
            1025                1030                1035

Asn Leu Gly Asn Ile His Val Ser Asp Asn Ile Leu Phe Lys Ile
            1040                1045                1050

Val Asn Cys Ser Tyr Thr Arg Tyr Ile Gly Ile Arg Tyr Phe Asn
            1055                1060                1065

Ile Phe Asp Lys Glu Leu Asp Glu Thr Glu Ile Gln Thr Leu Tyr
            1070                1075                1080

Ser Asn Glu Pro Asn Thr Asn Ile Leu Lys Asp Phe Trp Gly Asn
            1085                1090                1095

Tyr Leu Leu Tyr Asp Lys Glu Tyr Tyr Leu Leu Asn Val Leu Lys
            1100                1105                1110

Pro Asn Asn Phe Ile Asp Arg Arg Lys Asp Ser Thr Leu Ser Ile
            1115                1120                1125
```

```
Asn Asn Ile Arg Ser Thr Ile Leu Leu Ala Asn Arg Leu Tyr Ser
    1130                1135                1140

Gly Ile Lys Val Lys Ile Gln Arg Val Asn Asn Ser Ser Thr Asn
    1145                1150                1155

Asp Asn Leu Val Arg Lys Asp Gln Val Tyr Ile Asn Phe Val
    1160                1165                1170

Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 72
<211> LENGTH: 1272
<212> TYPE: PRT
<213> ORGANISM: Clostridium botulinum

<400> SEQUENCE: 72

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
```

-continued

```
                210                 215                 220
Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
                290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Lys Lys Leu Lys Val Lys Phe
                370                 375                 380

Arg Gly Gln Asn Ala Asn Lys Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
                420                 425                 430

Ser Leu Val Pro Arg Gly Ser Lys Ala Leu Asn Asp Leu Cys Ile Glu
                435                 440                 445

Ile Asn Asn Gly Glu Leu Phe Phe Val Ala Ser Glu Asn Ser Tyr Asn
                450                 455                 460

Asp Asp Asn Ile Asn Thr Pro Lys Glu Ile Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
                500                 505                 510

Gln Asn Asp Ala Tyr Ile Pro Lys Tyr Asp Ser Asn Gly Thr Ser Asp
                515                 520                 525

Ile Glu Gln His Asp Val Asn Glu Leu Asn Val Phe Phe Tyr Leu Asp
                530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
                595                 600                 605

Gln Lys Ser Thr Val Asp Lys Ile Ala Asp Ile Ser Ile Val Val Pro
610                 615                 620

Tyr Ile Gly Leu Ala Leu Asn Ile Gly Asn Glu Ala Gln Lys Gly Asn
625                 630                 635                 640
```

```
Phe Lys Asp Ala Leu Glu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
            850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
            995                 1000                1005

Lys Trp Ile Phe Val Thr Ile Thr Asn Asp Arg Leu Gly Asp Ser
            1010                1015                1020

Lys Leu Tyr Ile Asn Gly Asn Leu Ile Asp Gln Lys Ser Ile Leu
            1025                1030                1035

Asn Leu Gly Asn Ile His Val Ser Asp Asn Ile Leu Phe Lys Ile
            1040                1045                1050
```

Val Asn Cys Ser Tyr Thr Arg Tyr Ile Gly Ile Arg Tyr Phe Asn
1055                1060                1065

Ile Phe Asp Lys Glu Leu Asp Glu Thr Glu Ile Gln Thr Leu Tyr
1070                1075                1080

Ser Asn Glu Pro Asn Thr Asn Ile Leu Lys Asp Phe Trp Gly Asn
1085                1090                1095

Tyr Leu Leu Tyr Asp Lys Glu Tyr Tyr Leu Leu Asn Val Leu Lys
1100                1105                1110

Pro Asn Asn Phe Ile Asp Arg Arg Lys Asp Ser Thr Leu Ser Ile
1115                1120                1125

Asn Asn Ile Arg Ser Thr Ile Leu Leu Ala Asn Arg Leu Tyr Ser
1130                1135                1140

Gly Ile Lys Val Lys Ile Gln Arg Val Asn Asn Ser Ser Thr Asn
1145                1150                1155

Asp Asn Leu Val Arg Lys Asn Asp Gln Val Tyr Ile Asn Phe Val
1160                1165                1170

Ala Ser Lys Thr His Leu Phe Pro Leu Tyr Ala Asp Thr Ala Thr
1175                1180                1185

Thr Asn Lys Glu Lys Thr Ile Lys Ile Ser Ser Ser Gly Asn Arg
1190                1195                1200

Phe Asn Gln Val Val Val Met Asn Ser Val Gly Asn Asn Cys Thr
1205                1210                1215

Met Asn Phe Lys Asn Asn Asn Gly Asn Asn Ile Gly Leu Leu Gly
1220                1225                1230

Phe Lys Ala Asp Thr Val Val Ala Ser Thr Trp Tyr Tyr Thr His
1235                1240                1245

Met Arg Asp His Thr Asn Ser Asn Gly Cys Phe Trp Asn Phe Ile
1250                1255                1260

Ser Glu Glu His Gly Trp Gln Glu Lys
1265                1270

<210> SEQ ID NO 73
<211> LENGTH: 1272
<212> TYPE: PRT
<213> ORGANISM: Clostridium botulinum

<400> SEQUENCE: 73

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

```
Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
            165                 170                 175

Gly Phe Gly Ser Ile Ala Ile Val Thr Phe Ser Pro Glu Tyr Ser Phe
        180                 185                 190

Arg Phe Asn Asp Asn Ser Met Asn Glu Phe Ile Gln Asp Pro Ala Leu
    195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Lys Lys Leu Lys Val Asn Phe
370                 375                 380

Arg Gly Gln Asn Ala Asn Lys Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
530                 535                 540

Ala Gln Lys Val Pro Glu Gly Glu Asn Asn Val Asn Leu Thr Ser Ser
545                 550                 555                 560
```

```
Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
    610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
    690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
        755                 760                 765

Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
```

```
                980             985              990
Leu Ala Phe Asn Tyr Gly Asn Ala  Asn Gly Ile Ser Asp  Tyr Ile Asn
        995                1000                1005

Lys Trp Ile Phe Val Thr Ile  Thr Asn Asp Arg Leu  Gly Asp Ser
       1010                1015                 1020

Lys Leu Tyr Ile Asn Gly Asn  Leu Ile Asp Gln Lys  Ser Ile Leu
       1025                1030                 1035

Asn Leu Gly Asn Ile His Val  Ser Asp Asn Ile Leu  Phe Lys Ile
       1040                1045                 1050

Val Asn Cys Ser Tyr Thr Arg  Tyr Ile Gly Ile Arg  Tyr Phe Asn
       1055                1060                 1065

Ile Phe Asp Lys Glu Leu Asp  Glu Thr Glu Ile Gln  Thr Leu Tyr
       1070                1075                 1080

Ser Asn Glu Pro Asn Thr Asn  Ile Leu Lys Asp Phe  Trp Gly Asn
       1085                1090                 1095

Tyr Leu Leu Tyr Asp Lys Glu  Tyr Tyr Leu Leu Asn  Val Leu Lys
       1100                1105                 1110

Pro Asn Asn Phe Ile Asp Arg  Arg Lys Asp Ser Thr  Leu Ser Ile
       1115                1120                 1125

Asn Asn Ile Arg Ser Thr Ile  Leu Leu Ala Asn Arg  Leu Tyr Ser
       1130                1135                 1140

Gly Ile Lys Val Lys Ile Gln  Arg Val Asn Asn Ser  Ser Thr Asn
       1145                1150                 1155

Asp Asn Leu Val Arg Lys Asn  Asp Gln Val Tyr Ile  Asn Phe Val
       1160                1165                 1170

Ala Ser Lys Thr His Leu Phe  Pro Leu Tyr Ala Asp  Thr Ala Thr
       1175                1180                 1185

Thr Asn Lys Glu Lys Thr Ile  Lys Ile Ser Ser Ser  Gly Asn Arg
       1190                1195                 1200

Phe Asn Gln Val Val Val Met  Asn Ser Val Gly Asn  Asn Cys Thr
       1205                1210                 1215

Met Asn Phe Lys Asn Asn Asn  Gly Asn Asn Ile Gly  Leu Leu Gly
       1220                1225                 1230

Phe Lys Ala Asp Thr Val Val  Ala Ser Thr Trp Tyr  Tyr Thr His
       1235                1240                 1245

Met Arg Asp His Thr Asn Ser  Asn Gly Cys Phe Trp  Asn Phe Ile
       1250                1255                 1260

Ser Glu Glu His Gly Trp Gln  Glu Lys
       1265                1270

<210> SEQ ID NO 74
<211> LENGTH: 1272
<212> TYPE: PRT
<213> ORGANISM: Clostridium botulinum

<400> SEQUENCE: 74

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
             20                  25                  30

Phe Asn Ile Met Lys Asn Ile Trp Ile Ile Pro Glu Arg Asn Val Ile
         35                  40                  45

Gly Thr Thr Pro Gln Asp Phe His Pro Pro Ser Leu Lys Asn Gly
     50                  55                  60
```

```
Asp Ser Ser Tyr Tyr Asp Pro Asn Tyr Leu Gln Ser Asp Glu Glu Lys
 65                  70                  75                  80

Asp Arg Phe Leu Lys Ile Val Thr Lys Ile Phe Asn Arg Ile Asn Asn
             85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
            115                 120                 125

Ala Ser Ala Val Glu Ile Lys Phe Ser Asn Gly Ser Gln Asp Ile Leu
            130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
            195                 200                 205

Thr Leu Met His Glu Leu Ile His Ser Leu His Gly Leu Tyr Gly Ala
            210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
            290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
            355                 360                 365

Tyr Asn Ile Ser Glu Gly Tyr Asn Ile Lys Lys Leu Lys Val Asn Phe
370                 375                 380

Arg Gly Gln Asn Ala Asn Leu Asn Pro Lys Ile Ile Thr Pro Ile Thr
385                 390                 395                 400

Gly Arg Gly Leu Val Lys Lys Ile Ile Arg Phe Cys Val Arg Gly Ile
            405                 410                 415

Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
            450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
```

```
            485                 490                 495
Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Val Asn Leu Thr Ser Ser
545                 550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
            610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                        645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
            690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                        725                 730                 735

Thr Ile Ile Glu Ser Lys Tyr Asn Ser Tyr Thr Leu Glu Glu Lys Asn
                        740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                        805                 810                 815

Ile Ile Gln His Gly Ser Ile Leu Gly Glu Ser Gln Glu Leu Asn
            820                 825                 830

Ser Met Val Thr Asp Thr Leu Asn Asn Ser Ile Pro Phe Lys Leu Ser
            835                 840                 845

Ser Tyr Thr Asp Asp Lys Ile Leu Ile Ser Tyr Phe Asn Lys Phe Phe
            850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                        885                 890                 895

Asp Val Tyr Lys Tyr Pro Thr Asn Lys Asn Gln Phe Gly Ile Tyr Asn
            900                 905                 910
```

-continued

Asp Lys Leu Ser Glu Val Asn Ile Ser Gln Asn Asp Tyr Ile Ile Tyr
            915                 920                 925

Asp Asn Lys Tyr Lys Asn Phe Ser Ile Ser Phe Trp Val Arg Ile Pro
    930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala Asn Gly Ile Ser Asp Tyr Ile Asn
            995                 1000                1005

Lys Trp Ile Phe Val Thr Ile Thr Asn Asp Arg Leu Gly Asp Ser
        1010                1015                1020

Lys Leu Tyr Ile Asn Gly Asn Leu Ile Asp Gln Lys Ser Ile Leu
        1025                1030                1035

Asn Leu Gly Asn Ile His Val Ser Asp Asn Ile Leu Phe Lys Ile
        1040                1045                1050

Val Asn Cys Ser Tyr Thr Arg Tyr Ile Gly Ile Arg Tyr Phe Asn
        1055                1060                1065

Ile Phe Asp Lys Glu Leu Asp Glu Thr Glu Ile Gln Thr Leu Tyr
        1070                1075                1080

Ser Asn Glu Pro Asn Thr Asn Ile Leu Lys Asp Phe Trp Gly Asn
        1085                1090                1095

Tyr Leu Leu Tyr Asp Lys Glu Tyr Tyr Leu Leu Asn Val Leu Lys
        1100                1105                1110

Pro Asn Asn Phe Ile Asp Arg Arg Lys Asp Ser Thr Leu Ser Ile
        1115                1120                1125

Asn Asn Ile Arg Ser Thr Ile Leu Leu Ala Asn Arg Leu Tyr Ser
        1130                1135                1140

Gly Ile Lys Val Lys Ile Gln Arg Val Asn Asn Ser Ser Thr Asn
        1145                1150                1155

Asp Asn Leu Val Arg Lys Asn Asp Gln Val Tyr Ile Asn Phe Val
        1160                1165                1170

Ala Ser Lys Thr His Leu Phe Pro Leu Tyr Ala Asp Thr Ala Thr
        1175                1180                1185

Thr Asn Lys Glu Lys Thr Ile Lys Ile Ser Ser Ser Gly Asn Arg
        1190                1195                1200

Phe Asn Gln Val Val Val Met Asn Ser Val Gly Asn Asn Cys Thr
        1205                1210                1215

Met Asn Phe Lys Asn Asn Gly Asn Asn Ile Gly Leu Leu Gly
        1220                1225                1230

Phe Lys Ala Asp Thr Val Val Ala Ser Thr Trp Tyr Tyr Thr His
        1235                1240                1245

Met Arg Asp His Thr Asn Ser Asn Gly Cys Phe Trp Asn Phe Ile
        1250                1255                1260

Ser Glu Glu His Gly Trp Gln Glu Lys
        1265                1270

<210> SEQ ID NO 75
<211> LENGTH: 1272
<212> TYPE: PRT
<213> ORGANISM: Clostridium botulinum

<400> SEQUENCE: 75

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65              70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
    290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Lys Lys Leu Lys Val Asn Phe
    370                 375                 380

Arg Gly Gln Asn Ala Asn Leu Asn Pro Arg Ile Ile Thr Pro Ile Lys
385                 390                 395                 400

Gly Arg Gly Leu Val Lys Lys Ile Ile Arg Phe Cys Val Arg Gly Ile
                405                 410                 415
```

```
Ile Thr Ser Leu Thr Phe Glu His Asn Trp Ala Gln Leu Thr Ser Lys
            420                 425                 430

Ser Leu Val Pro Arg Gly Ser Lys Ala Leu Asn Asp Leu Cys Ile Glu
            435                 440                 445

Ile Asn Asn Gly Glu Leu Phe Phe Val Ala Ser Glu Asn Ser Tyr Asn
            450                 455                 460

Asp Asp Asn Ile Asn Thr Pro Lys Glu Ile Asp Thr Val Thr Ser
465             470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
            515                 520                 525

Ile Glu Gln His Asp Val Asn Glu Leu Asn Val Phe Phe Tyr Leu Asp
            530                 535                 540

Ala Gln Lys Val Pro Glu Gly Glu Asn Asn Val Asn Leu Thr Ser Ser
545             550                 555                 560

Ile Asp Thr Ala Leu Leu Glu Gln Pro Lys Ile Tyr Thr Phe Phe Ser
            565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
            595                 600                 605

Gln Lys Ser Thr Val Asp Lys Ile Ala Asp Ile Ser Ile Val Val Pro
            610                 615                 620

Tyr Ile Gly Leu Ala Leu Asn Ile Gly Asn Glu Ala Gln Lys Gly Asn
625             630                 635                 640

Phe Lys Asp Ala Leu Glu Leu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
            675                 680                 685

Asn Ala Leu Lys Glu Arg Asp Glu Lys Trp Lys Glu Val Tyr Ser Phe
            690                 695                 700

Ile Val Ser Asn Trp Met Thr Lys Ile Asn Thr Gln Phe Asn Lys Arg
705             710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
            740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
            770                 775                 780

Ser Ser Ile Ser Tyr Leu Met Lys Leu Ile Asn Glu Val Lys Ile Asn
785             790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Gln Glu Leu Asn
            820                 825                 830
```

-continued

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
850                 855                 860

Lys Arg Ile Lys Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
                900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
                930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
                980                 985                 990

Leu Ala Phe Asn Tyr Gly Asn Ala Asn Gly Ile Ser Asp Tyr Ile Asn
                995                 1000                1005

Lys Trp Ile Phe Val Thr Ile Thr Asn Asp Arg Leu Gly Asp Ser
                1010                1015                1020

Lys Leu Tyr Ile Asn Gly Asn Leu Ile Asp Gln Lys Ser Ile Leu
                1025                1030                1035

Asn Leu Gly Asn Ile His Val Ser Asp Asn Ile Leu Phe Lys Ile
                1040                1045                1050

Val Asn Cys Ser Tyr Thr Arg Tyr Ile Gly Ile Arg Tyr Phe Asn
                1055                1060                1065

Ile Phe Asp Lys Glu Leu Asp Glu Thr Glu Ile Gln Thr Leu Tyr
                1070                1075                1080

Ser Asn Glu Pro Asn Thr Asn Ile Leu Lys Asp Phe Trp Gly Asn
                1085                1090                1095

Tyr Leu Leu Tyr Asp Lys Glu Tyr Tyr Leu Leu Asn Val Leu Lys
                1100                1105                1110

Pro Asn Asn Phe Ile Asp Arg Arg Lys Asp Ser Thr Leu Ser Ile
                1115                1120                1125

Asn Asn Ile Arg Ser Thr Ile Leu Leu Ala Asn Arg Leu Tyr Ser
                1130                1135                1140

Gly Ile Lys Val Lys Ile Gln Arg Val Asn Asn Ser Ser Thr Asn
                1145                1150                1155

Asp Asn Leu Val Arg Lys Asn Asp Gln Val Tyr Ile Asn Phe Val
                1160                1165                1170

Ala Ser Lys Thr His Leu Phe Pro Leu Tyr Ala Asp Thr Ala Thr
                1175                1180                1185

Thr Asn Lys Glu Lys Thr Ile Lys Ile Ser Ser Ser Gly Asn Arg
                1190                1195                1200

Phe Asn Gln Val Val Val Met Asn Ser Val Gly Asn Asn Cys Thr
                1205                1210                1215

Met Asn Phe Lys Asn Asn Asn Gly Asn Asn Ile Gly Leu Leu Gly
                1220                1225                1230

Phe Lys Ala Asp Thr Val Val Ala Ser Thr Trp Tyr Tyr Thr His

```
                    1235                1240                1245
Met Arg Asp His Thr Asn Ser Asn Gly Cys Phe Trp Asn Phe Ile
               1250                1255                1260

Ser Glu Glu His Gly Trp Gln Glu Lys
               1265                1270

<210> SEQ ID NO 76
<211> LENGTH: 1272
<212> TYPE: PRT
<213> ORGANISM: Clostridium botulinum

<400> SEQUENCE: 76

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Gln Asp Phe His Pro Pro Thr Ser Leu Lys Asn Gly
        50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335
```

```
Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Lys Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Thr Ser Lys
                420                 425                 430

Ser Leu Val Pro Arg Gly Ser Lys Ala Leu Asn Asp Leu Cys Ile Glu
                435                 440                 445

Ile Asn Asn Gly Glu Leu Phe Phe Val Ala Ser Glu Asn Ser Tyr Asn
            450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
                500                 505                 510

Gln Asn Asp Ala Tyr Ile Pro Lys Tyr Asp Ser Asn Gly Thr Ser Asp
                515                 520                 525

Ile Glu Gln His Asp Val Asn Glu Leu Asn Val Phe Phe Tyr Leu Asp
                530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
                580                 585                 590

Val Ser Trp Ile Gln Gln Val Leu Val Asp Phe Thr Thr Glu Ala Asn
                595                 600                 605

Gln Lys Ser Thr Val Asp Lys Ile Ala Asp Ile Ser Ile Val Val Pro
                610                 615                 620

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
                645                 650                 655

Glu Pro Glu Leu Leu Ile Pro Thr Ile Leu Val Phe Thr Ile Lys Ser
                660                 665                 670

Phe Leu Gly Ser Ser Asp Asn Lys Asn Lys Val Ile Lys Ala Ile Asn
                675                 680                 685

Asn Ala Leu Lys Glu Arg Asp Glu Lys Trp Lys Glu Val Tyr Ser Phe
                690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
```

-continued

```
            755                 760                 765
    Gln Lys Val Ser Ile Ala Met Asn Asn Ile Asp Arg Phe Leu Thr Glu
    770                 775                 780

Ser Ser Ile Ser Tyr Leu Met Lys Leu Ile Asn Glu Val Lys Ile Asn
    785                 790                 795                 800

Lys Leu Arg Glu Tyr Asp Glu Asn Val Lys Thr Tyr Leu Leu Asn Tyr
                        805                 810                 815

Ile Ile Gln His Gly Ser Ile Leu Gly Glu Ser Gln Gln Leu Asn
                    820                 825                 830

Ser Met Val Thr Asp Thr Leu Asn Asn Ser Ile Pro Phe Lys Leu Ser
                835                 840                 845

Ser Tyr Thr Asp Asp Lys Ile Leu Ile Ser Tyr Phe Asn Lys Phe Phe
            850                 855                 860

Lys Arg Ile Lys Ser Ser Val Leu Asn Met Arg Tyr Lys Asn Asp
    865                 870                 875                 880

Lys Tyr Val Asp Thr Ser Gly Tyr Asp Ser Asn Ile Asn Ile Asn Gly
                        885                 890                 895

Asp Val Tyr Lys Tyr Pro Thr Asn Lys Asn Gln Phe Gly Ile Tyr Asn
                    900                 905                 910

Asp Lys Leu Ser Glu Val Asn Ile Ser Gln Asn Asp Tyr Ile Ile Tyr
                915                 920                 925

Asp Asn Lys Tyr Lys Asn Phe Ser Ile Ser Phe Trp Val Arg Ile Pro
            930                 935                 940

Asn Tyr Asp Asn Lys Ile Val Asn Val Asn Asn Glu Tyr Thr Ile Ile
    945                 950                 955                 960

Asn Cys Met Arg Asp Asn Asn Ser Gly Trp Lys Val Ser Leu Asn His
                        965                 970                 975

Asn Glu Ile Ile Trp Thr Leu Gln Asp Asn Ala Gly Ile Asn Gln Lys
                    980                 985                 990

Leu Ala Phe Asn Tyr Gly Asn Ala  Asn Gly Ile Ser Asp  Tyr Ile Asn
                995                 1000                1005

Lys Trp  Ile Phe Val Thr Ile  Thr Asn Asp Arg Leu  Gly Asp Ser
    1010                1015                1020

Lys Leu  Tyr Ile Asn Gly Asn  Leu Ile Asp Gln Lys  Ser Ile Leu
    1025                1030                1035

Asn Leu  Gly Asn Ile His Val  Ser Asp Asn Ile Leu  Phe Lys Ile
    1040                1045                1050

Val Asn  Cys Ser Tyr Thr Arg  Tyr Ile Gly Ile Arg  Tyr Phe Asn
    1055                1060                1065

Ile Phe  Asp Lys Glu Leu Asp  Glu Thr Glu Ile Gln  Thr Leu Tyr
    1070                1075                1080

Ser Asn  Glu Pro Asn Thr Asn  Ile Leu Lys Asp Phe  Trp Gly Asn
    1085                1090                1095

Tyr Leu  Leu Tyr Asp Lys Glu  Tyr Tyr Leu Leu Asn  Val Leu Lys
    1100                1105                1110

Pro Asn  Asn Phe Ile Asp Arg  Arg Lys Asp Ser Thr  Leu Ser Ile
    1115                1120                1125

Asn Asn  Ile Arg Ser Thr Ile  Leu Leu Ala Asn Arg  Leu Tyr Ser
    1130                1135                1140

Gly Ile  Lys Val Lys Ile Gln  Arg Val Asn Asn Ser  Ser Thr Asn
    1145                1150                1155

Asp Asn  Leu Val Arg Lys Asn  Asp Gln Val Tyr Ile  Asn Phe Val
    1160                1165                1170
```

-continued

```
Ala Ser Lys Thr His Leu Phe Pro Leu Tyr Ala Asp Thr Ala Thr
    1175                1180                1185

Thr Asn Lys Glu Lys Thr Ile Lys Ile Ser Ser Ser Gly Asn Arg
    1190                1195                1200

Phe Asn Gln Val Val Val Met Asn Ser Val Gly Asn Asn Cys Thr
    1205                1210                1215

Met Asn Phe Lys Asn Asn Gly Asn Asn Ile Gly Leu Leu Gly
    1220                1225                1230

Phe Lys Ala Asp Thr Val Val Ala Ser Thr Trp Tyr Tyr Thr His
    1235                1240                1245

Met Arg Asp His Thr Asn Ser Asn Gly Cys Phe Trp Asn Phe Ile
    1250                1255                1260

Ser Glu Glu His Gly Trp Gln Glu Lys
    1265                1270

<210> SEQ ID NO 77
<211> LENGTH: 1272
<212> TYPE: PRT
<213> ORGANISM: Clostridium botulinum

<400> SEQUENCE: 77

Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
                20                  25                  30

Phe Asn Ile Met Lys Asn Ile Trp Ile Ile Pro Glu Arg Asn Val Ile
            35                  40                  45

Gly Thr Thr Pro Lys Asp Phe His Pro Pro Thr Ser Leu Lys Asn Gly
        50                  55                  60

Asp Ser Ser Tyr Tyr Asp Pro Lys Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
```

```
            260             265             270
Thr Asn Leu Leu Ala Asp Tyr Lys Lys Ile Ala Ser Lys Leu Ser Lys
            275             280             285

Val Gln Val Ser Asn Pro Leu Leu Asn Pro Tyr Lys Asp Val Phe Glu
            290             295             300

Ala Lys Tyr Gly Leu Asp Lys Asp Ala Ser Gly Ile Tyr Ser Val Asn
305             310             315             320

Ile Asn Lys Phe Asn Asp Ile Phe Lys Lys Leu Tyr Ser Phe Thr Glu
            325             330             335

Phe Asp Leu Ala Thr Lys Phe Gln Val Lys Cys Arg Gln Thr Tyr Ile
            340             345             350

Gly Gln Tyr Lys Tyr Phe Lys Leu Ser Asn Leu Leu Asn Asp Ser Ile
            355             360             365

Tyr Asn Ile Ser Glu Gly Tyr Asn Ile Lys Lys Leu Val Asn Phe
            370             375             380

Arg Gly Gln Asn Ala Asn Leu Asn Pro Arg Ile Ile Thr Pro Ile Lys
385             390             395             400

Gly Arg Gly Leu Val Lys Lys Ile Ile Arg Phe Cys Val Arg Gly Ile
            405             410             415

Ile Thr Ser Leu Thr Phe Glu His Asn Trp Ala Gln Leu Thr Ser Lys
            420             425             430

Ser Leu Val Pro Arg Gly Ser Lys Ala Leu Asn Asp Leu Cys Ile Glu
            435             440             445

Ile Asn Asn Gly Glu Leu Phe Phe Val Ala Ser Glu Asn Ser Tyr Asn
            450             455             460

Asp Asp Asn Ile Asn Thr Pro Lys Glu Ile Asp Asp Thr Val Thr Ser
465             470             475             480

Asn Asn Asn Tyr Glu Asn Asp Leu Asp Gln Val Ile Leu Asn Phe Asn
            485             490             495

Ser Glu Ser Ala Pro Gly Leu Ser Asp Glu Lys Leu Asn Leu Thr Ile
            500             505             510

Gln Asn Asp Ala Tyr Ile Pro Lys Tyr Asp Ser Asn Gly Thr Ser Asp
            515             520             525

Ile Glu Gln His Asp Val Asn Glu Leu Asn Val Phe Phe Tyr Leu Asp
            530             535             540

Ala Gln Lys Val Pro Glu Gly Glu Asn Asn Val Asn Leu Thr Ser Ser
545             550             555             560

Ile Asp Thr Ala Leu Leu Glu Gln Pro Lys Ile Tyr Thr Phe Phe Ser
            565             570             575

Ser Glu Phe Ile Asn Asn Val Asn Lys Pro Val Gln Ala Ala Leu Phe
            580             585             590

Val Ser Trp Ile Gln Gln Val Leu Val Asp Phe Thr Thr Glu Ala Asn
            595             600             605

Gln Lys Ser Thr Val Asp Lys Ile Ala Asp Ile Ser Ile Val Val Pro
            610             615             620

Tyr Ile Gly Leu Ala Leu Asn Ile Gly Asn Glu Ala Gln Lys Gly Asn
625             630             635             640

Phe Lys Asp Ala Leu Glu Leu Leu Gly Ala Gly Ile Leu Leu Glu Phe
            645             650             655

Glu Pro Glu Leu Leu Ile Pro Thr Ile Leu Val Phe Thr Ile Lys Ser
            660             665             670

Phe Leu Gly Ser Ser Asp Asn Lys Asn Lys Val Ile Lys Ala Ile Asn
            675             680             685
```

```
Asn Ala Leu Lys Glu Arg Asp Glu Lys Trp Lys Glu Val Tyr Ser Phe
    690             695             700

Ile Val Ser Asn Trp Met Thr Lys Ile Asn Thr Gln Phe Asn Lys Arg
705             710             715             720

Lys Glu Gln Met Tyr Gln Ala Leu Gln Asn Gln Val Asn Ala Ile Lys
            725             730             735

Thr Ile Ile Glu Ser Lys Tyr Asn Ser Tyr Thr Leu Glu Glu Lys Asn
                740             745             750

Glu Leu Thr Asn Lys Tyr Asp Ile Lys Gln Ile Glu Asn Glu Leu Asn
        755             760             765

Gln Lys Val Ser Ile Ala Met Asn Asn Ile Asp Arg Phe Leu Thr Glu
    770             775             780

Ser Ser Ile Ser Tyr Leu Met Lys Leu Ile Asn Glu Val Lys Ile Asn
785             790             795             800

Lys Leu Arg Glu Tyr Asp Glu Asn Val Lys Thr Tyr Leu Leu Asn Tyr
            805             810             815

Ile Ile Gln His Gly Ser Ile Leu Gly Ser Gln Gln Glu Leu Asn
                820             825             830

Ser Met Val Thr Asp Thr Leu Asn Asn Ser Ile Pro Phe Lys Leu Ser
        835             840             845

Ser Tyr Thr Asp Asp Lys Ile Leu Ile Ser Tyr Phe Asn Lys Phe Phe
    850             855             860

Lys Arg Ile Lys Ser Ser Val Leu Asn Met Arg Tyr Lys Asn Asp
865             870             875             880

Lys Tyr Val Asp Thr Ser Gly Tyr Asp Ser Asn Ile Asn Ile Asn Gly
            885             890             895

Asp Val Tyr Lys Tyr Pro Thr Asn Lys Asn Gln Phe Gly Ile Tyr Asn
                900             905             910

Asp Lys Leu Ser Glu Val Asn Ile Ser Gln Asn Asp Tyr Ile Ile Tyr
        915             920             925

Asp Asn Lys Tyr Lys Asn Phe Ser Ile Ser Phe Trp Val Arg Ile Pro
    930             935             940

Asn Tyr Asp Asn Lys Ile Val Asn Val Asn Asn Glu Tyr Thr Ile Ile
945             950             955             960

Asn Cys Met Arg Asp Asn Asn Ser Gly Trp Lys Val Ser Leu Asn His
            965             970             975

Asn Glu Ile Ile Trp Thr Leu Gln Asp Asn Ala Gly Ile Asn Gln Lys
                980             985             990

Leu Ala Phe Asn Tyr Gly Asn Ala  Asn Gly Ile Ser Asp  Tyr Ile Asn
        995             1000             1005

Lys Trp Ile Phe Val Thr Ile  Thr Asn Asp Arg Leu  Gly Asp Ser
    1010             1015             1020

Lys Leu Tyr Ile Asn Gly Asn  Leu Ile Asp Gln Lys  Ser Ile Leu
    1025             1030             1035

Asn Leu Gly Asn Ile His Val  Ser Asp Asn Ile Leu  Phe Lys Ile
    1040             1045             1050

Val Asn Cys Ser Tyr Thr Arg  Tyr Ile Gly Ile Arg  Tyr Phe Asn
    1055             1060             1065

Ile Phe Asp Lys Glu Leu Asp  Glu Thr Glu Ile Gln  Thr Leu Tyr
    1070             1075             1080

Ser Asn Glu Pro Asn Thr Asn  Ile Leu Lys Asp Phe  Trp Gly Asn
    1085             1090             1095
```

```
Tyr Leu  Leu Tyr Asp Lys Glu  Tyr Tyr Leu Leu Asn  Val Leu Lys
    1100                 1105                 1110

Pro Asn  Asn Phe Ile Asp Arg  Arg Lys Asp Ser Thr  Leu Ser Ile
    1115                 1120                 1125

Asn Asn  Ile Arg Ser Thr Ile  Leu Leu Ala Asn Arg  Leu Tyr Ser
    1130                 1135                 1140

Gly Ile  Lys Val Lys Ile Gln  Arg Val Asn Asn Ser  Ser Thr Asn
    1145                 1150                 1155

Asp Asn  Leu Val Arg Lys Asn  Asp Gln Val Tyr Ile  Asn Phe Val
    1160                 1165                 1170

Ala Ser  Lys Thr His Leu Phe  Pro Leu Tyr Ala Asp  Thr Ala Thr
    1175                 1180                 1185

Thr Asn  Lys Glu Lys Thr Ile  Lys Ile Ser Ser Ser  Gly Asn Arg
    1190                 1195                 1200

Phe Asn  Gln Val Val Val Met  Asn Ser Val Gly Asn  Asn Cys Thr
    1205                 1210                 1215

Met Asn  Phe Lys Asn Asn Asn  Gly Asn Asn Ile Gly  Leu Leu Gly
    1220                 1225                 1230

Phe Lys  Ala Asp Thr Val Val  Ala Ser Thr Trp Tyr  Tyr Thr His
    1235                 1240                 1245

Met Arg  Asp His Thr Asn Ser  Asn Gly Cys Phe Trp  Asn Phe Ile
    1250                 1255                 1260

Ser Glu  Glu His Gly Trp Gln  Glu Lys
    1265                 1270
```

```
<210> SEQ ID NO 78
<211> LENGTH: 12
<212> TYPE: PRT
<213> ORGANISM: artificial sequence
<220> FEATURE:
<223> OTHER INFORMATION: ligase recognition motif

<400> SEQUENCE: 78

Leu Thr Phe Glu His Asn Trp Ala Gln Leu Glu Asn
1               5                   10

<210> SEQ ID NO 79
<211> LENGTH: 3819
<212> TYPE: DNA
<213> ORGANISM: Artificial sequence
<220> FEATURE:
<223> OTHER INFORMATION: recombinant protein BONT/E with MDM2 binding
      motif

<400> SEQUENCE: 79
atgccgaaaa tcaacagctt caactataac gatccggtga acgatcgtac catcctgtat      60
attaaaccgg gcggttgcca ggaattttac aaaagcttca acatcatgaa aaacatctgg     120
attattccgg aacgtaacgt gattggcacc accccgcagg attttcatcc gccgaccagc     180
ctgaaaaacg gcgatagcag ctattatgat ccgaactatc tgcagtctga tgaagaaaaa     240
gatcgcttcc tgaaaatcgt gaccaaaatc ttcaaccgca tcaacaacaa cctgagcggc     300
ggcattctgc tggaagaact gagcaaagcg aatccgtatc tgggcaacga taacactcca     360
gataaccagt ttcatattgg tgatgcgagc gcggtggaaa ttaaatttag caacggctct     420
caggacattc tgctgccgaa cgtgattatt atgggcgcgg aaccggacct gtttgaaacc     480
aacagcagca acattagcct gcgtaacaac tatatgccga gcaaccatgg ttttggcagc     540
attgcgattg tgacctttag cccggaatat agctttcgct tcaacgataa cagcatgaac     600
```

```
gaatttattc aggacccggc gctgaccctg atgcacgagc tgattcatag cctgcatggc    660
ctgtatggcg cgaaaggcat taccaccaaa tataccatca cccagaaaca gaatccgctg    720
attaccaaca ttcgtggcac caacattgaa gaatttctga cctttggcgg caccgatctg    780
aacattatta ccagcgcgca gagcaacgat atctatacca acctgctggc cgattataaa    840
aaaatcgcgt ctaaactgag caaagtgcag gtgagcaatc cgctgctgaa tccgtataaa    900
gatgtgtttg aagcgaaata tggcctggat aaagatgcta gcggcattta tagcgtgaac    960
atcaacaaat tcaacgacat cttcaaaaaa ctgtatagct ttaccgaatt tgatctggcc   1020
accaaatttc aggtgaaatg ccgccagacc tatattggcc agtataaata ttttaaactg   1080
agcaacctgc tgaacgatag catttacaac atcagcgaag gctataacat caacaacctg   1140
aaagtgaact ttcgtggcca gaacgcgaat ttaaatccgc gtattattac cccgattacc   1200
ggccgtggac tagtgaaaaa aattatccgt ttttgcgtgc gtggcattat caccagcctg   1260
acctttgaac ataattgggc acagctgaaa aacaaaagcc tggtgccgcg tggcagcaaa   1320
gcgttaaatg atttatgcat cgaaatcaac aacggcgaac tgttttttgt ggcgagcgaa   1380
aacagctata cgatgataa catcaacacc ccgaaagaaa ttgatgatac cgtgaccagc   1440
aataacaact acgaaaacga tctggatcag gtgattctga actttaacag cgaaagcgca   1500
ccgggcctgt ctgatgaaaa actgaacctg accattcaga cgatgcgta tatcccgaaa   1560 tatgatagca acggcaccag cgatattgaa cagcatgatg tgaacgaact gaacgtgttt   1620
ttttatctgg atgcgcagaa agtgccggaa ggcgaaaaca cgtgaatct gaccagctca   1680 attgataccg cgctgctgga acagccgaaa atctatacct tttttagcag cgaattcatc   1740
aacaacgtga acaaaccggt gcaggcggcg ctgtttgtga gctggattca gcaggtgctg   1800 gttgattta ccaccgaagc gaaccagaaa agcaccgtgg ataaaattgc ggatattagc   1860
attgtggtgc cgtatattgg cctggccctg aacattggca acgaagcgca gaaaggcaac   1920
tttaaagatg cgctggaact gctgggtgcg ggcattctgc tggaatttga accggaactg   1980
ctgattccga ccattctggt gtttaccatc aaaagctttc tgggcagcag cgataacaaa   2040
aacaaagtga tcaaagcgat taacaacgcg ctgaaagaac gtgatgaaaa atggaaagaa   2100
gtgtatagct tcattgtgtc taactggatg accaaaatca cacccagtt caacaaacgt   2160 aaagaacaaa tgtatcaggc gctgcagaac caggtgaacg cgattaaaac catcatcgaa   2220
agcaaataca acagctacac cctggaagaa aaaaacgaac tgaccaacaa atatgacatc   2280
aaacaaatcg aaaatgaact gaaccagaaa gtgagcattg ccatgaacaa cattgatcgc   2340
tttctgaccg aaagcagcat tagctacctg atgaaactga tcaacgaagt gaaaatcaac   2400
aaactgcgcg aatatgatga aacgtgaaa acctacctgc tgaactatat tattcagcat   2460
ggcagcattc tgggcgaaag ccagcaagaa ctgaacagca tggttaccga taccctgaac   2520
aacagcattc cgtttaaact gagcagctac accgatgata aaatcctgat cagctacttc   2580
aacaaattct tcaaacgcat caaaagcagc agcgtgctga acatgcgtta taaaaacgat   2640
aaatacgtag ataccagcgg ctatgatagc aatatcaaca ttaacggtga tgtgtataaa   2700
tacccgacca caaaaaacca gttcggcatc tacaacgata aactgagcga agtgaacatt   2760
agccagaacg attatatcat ctacgataat aaatataaaa acttcagcat cagcttttgg   2820
gtgcgtattc cgaactacga taacaaaatc gtgaacgtga acaacgaata caccatcatt   2880
aactgcatgc gtgataacaa cagcggctgg aaagtgagcc tgaaccataa cgaaatcatc   2940
```

-continued

```
tggaccctgc aggataacgc cggcattaac cagaaactgg cctttaacta tggcaacgcg    3000
aacggcatta gcgattacat caacaaatgg atctttgtga ccattaccaa cgatcgtctg    3060
ggcgatagca aactgtatat taacggcaac ctgatcgacc agaaaagcat tctgaacctg    3120
ggcaacattc atgtgagcga taacatcctg ttcaaaattg tgaactgcag ctatacccgt    3180
tatattggca tccgctattt caacatcttc gataaagaac tggatgaaac cgaaattcag    3240
accctgtata gcaacgaacc gaacaccaac atcctgaaag atttctgggg caactatctg    3300
ctgtacgata agaatatta tctgctgaac gtgctgaaac cgaacaactt tattgatcgc    3360
cgtaaagata gcacccctgag cattaacaac attcgtagca ccattctgct ggccaaccgt    3420
ctgtatagcg gcattaaagt gaaaattcag cgcgtgaaca atagcagcac caacgataac    3480
ctggtgcgta aaaacgatca ggtgtatatc aactttgtgg ccagcaaaac ccacctgttt    3540
ccgctgtatg cggataccgc gaccaccaac aaagaaaaaa ccattaaaat cagcagcagc    3600
ggcaaccgtt ttaaccaggt ggtggtgatg aacagcgtgg gcaacaactg tacaatgaac    3660
ttcaaaaaca caacggcaa caacattggc ctgctgggct ttaaagcgga taccgtggtg    3720
gcgagcacct ggtattatac ccacatgcgt gatcatacca acagcaacgg ctgcttttgg    3780
aactttatta gcgaagaaca tggctggcag gaaaaatga                           3819
```

<210> SEQ ID NO 80
<211> LENGTH: 1272
<212> TYPE: PRT
<213> ORGANISM: artificial sequence
<220> FEATURE:
<223> OTHER INFORMATION: recombinant protein BONT/E with MDM2 binding motif

<400> SEQUENCE: 80

```
Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205
```

```
Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
        275                 280                 285

Val Gln Val Ser Asn Pro Leu Leu Asn Pro Tyr Lys Asp Val Phe Glu
290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
            340                 345                 350

Gly Gln Tyr Lys Tyr Phe Lys Leu Ser Asn Leu Leu Asn Asp Ser Ile
        355                 360                 365

Tyr Asn Ile Ser Glu Gly Tyr Asn Ile Asn Asn Leu Lys Val Asn Phe
370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Leu Thr Phe Glu His Asn Trp Ala Gln Leu Glu Asn Lys
            420                 425                 430

Ser Leu Val Pro Arg Gly Ser Lys Ala Leu Asn Asp Leu Cys Ile Glu
        435                 440                 445

Ile Asn Asn Gly Glu Leu Phe Phe Val Ala Ser Glu Asn Ser Tyr Asn
450                 455                 460

Asp Asp Asn Ile Asn Thr Pro Lys Glu Ile Asp Asp Thr Val Thr Ser
465                 470                 475                 480

Asn Asn Asn Tyr Glu Asn Asp Leu Asp Gln Val Ile Leu Asn Phe Asn
                485                 490                 495

Ser Glu Ser Ala Pro Gly Leu Ser Asp Glu Lys Leu Asn Leu Thr Ile
            500                 505                 510

Gln Asn Asp Ala Tyr Ile Pro Lys Tyr Asp Ser Asn Gly Thr Ser Asp
        515                 520                 525

Ile Glu Gln His Asp Val Asn Glu Leu Asn Val Phe Phe Tyr Leu Asp
530                 535                 540

Ala Gln Lys Val Pro Glu Gly Glu Asn Asn Val Asn Leu Thr Ser Ser
545                 550                 555                 560

Ile Asp Thr Ala Leu Leu Glu Gln Pro Lys Ile Tyr Thr Phe Phe Ser
                565                 570                 575

Ser Glu Phe Ile Asn Asn Val Asn Lys Pro Val Gln Ala Ala Leu Phe
            580                 585                 590

Val Ser Trp Ile Gln Gln Val Leu Val Asp Phe Thr Thr Glu Ala Asn
        595                 600                 605

Gln Lys Ser Thr Val Asp Lys Ile Ala Asp Ile Ser Ile Val Val Pro
610                 615                 620
```

-continued

Tyr Ile Gly Leu Ala Leu Asn Ile Gly Asn Glu Ala Gln Lys Gly Asn
625                 630                 635                 640

Phe Lys Asp Ala Leu Glu Leu Leu Gly Ala Gly Ile Leu Leu Glu Phe
            645                 650                 655

Glu Pro Glu Leu Leu Ile Pro Thr Ile Leu Val Phe Thr Ile Lys Ser
            660                 665                 670

Phe Leu Gly Ser Ser Asp Asn Lys Asn Lys Val Ile Lys Ala Ile Asn
        675                 680                 685

Asn Ala Leu Lys Glu Arg Asp Glu Lys Trp Lys Glu Val Tyr Ser Phe
690                 695                 700

Ile Val Ser Asn Trp Met Thr Lys Ile Asn Thr Gln Phe Asn Lys Arg
705                 710                 715                 720

Lys Glu Gln Met Tyr Gln Ala Leu Gln Asn Gln Val Asn Ala Ile Lys
                725                 730                 735

Thr Ile Ile Glu Ser Lys Tyr Asn Ser Tyr Thr Leu Glu Glu Lys Asn
                740                 745                 750

Glu Leu Thr Asn Lys Tyr Asp Ile Lys Gln Ile Glu Asn Glu Leu Asn
            755                 760                 765

Gln Lys Val Ser Ile Ala Met Asn Asn Ile Asp Arg Phe Leu Thr Glu
770                 775                 780

Ser Ser Ile Ser Tyr Leu Met Lys Leu Ile Asn Glu Val Lys Ile Asn
785                 790                 795                 800

Lys Leu Arg Glu Tyr Asp Glu Asn Val Lys Thr Tyr Leu Leu Asn Tyr
                805                 810                 815

Ile Ile Gln His Gly Ser Ile Leu Gly Glu Ser Gln Asn Glu Leu Asn
            820                 825                 830

Ser Met Val Thr Asp Thr Leu Asn Asn Ser Ile Pro Phe Lys Leu Ser
        835                 840                 845

Ser Tyr Thr Asp Asp Lys Ile Leu Ile Ser Tyr Phe Asn Lys Phe Phe
    850                 855                 860

Lys Arg Ile Lys Ser Ser Ser Val Leu Asn Met Arg Tyr Lys Asn Asp
865                 870                 875                 880

Lys Tyr Val Asp Thr Ser Gly Tyr Asp Ser Asn Ile Asn Ile Asn Gly
                885                 890                 895

Asp Val Tyr Lys Tyr Pro Thr Asn Lys Asn Gln Phe Gly Ile Tyr Asn
            900                 905                 910

Asp Lys Leu Ser Glu Val Asn Ile Ser Gln Asn Asp Tyr Ile Ile Tyr
        915                 920                 925

Asp Asn Lys Tyr Lys Asn Phe Ser Ile Ser Phe Trp Val Arg Ile Pro
930                 935                 940

Asn Tyr Asp Asn Lys Ile Val Asn Val Asn Asn Glu Tyr Thr Ile Ile
945                 950                 955                 960

Asn Cys Met Arg Asp Asn Asn Ser Gly Trp Lys Val Ser Leu Asn His
                965                 970                 975

Asn Glu Ile Ile Trp Thr Leu Gln Asp Asn Ala Gly Ile Asn Gln Lys
            980                 985                 990

Leu Ala Phe Asn Tyr Gly Asn Ala  Asn Gly Ile Ser Asp Tyr Ile Asn
        995                 1000                1005

Lys Trp Ile Phe Val Thr Ile  Thr Asn Asp Arg Leu  Gly Asp Ser
        1010                1015                1020

Lys Leu Tyr Ile Asn Gly Asn  Leu Ile Asp Gln Lys  Ser Ile Leu
        1025                1030                1035

Asn Leu Gly Asn Ile His Val  Ser Asp Asn Ile Leu  Phe Lys Ile

|   |   |   |   |   |   |   |   |   |   |
|---|---|---|---|---|---|---|---|---|---|
| | | | 1040 | | | 1045 | | | 1050 |
| Val | Asn | Cys | Ser | Tyr | Thr | Arg | Tyr | Ile | Gly | Ile | Arg | Tyr | Phe | Asn |
| | | 1055 | | | | 1060 | | | 1065 |
| Ile | Phe | Asp | Lys | Glu | Leu | Asp | Glu | Thr | Glu | Ile | Gln | Thr | Leu | Tyr |
| | 1070 | | | | 1075 | | | | 1080 |
| Ser | Asn | Glu | Pro | Asn | Thr | Asn | Ile | Leu | Lys | Asp | Phe | Trp | Gly | Asn |
| | 1085 | | | | 1090 | | | | 1095 |
| Tyr | Leu | Leu | Tyr | Asp | Lys | Glu | Tyr | Tyr | Leu | Leu | Asn | Val | Leu | Lys |
| | 1100 | | | | 1105 | | | | 1110 |
| Pro | Asn | Asn | Phe | Ile | Asp | Arg | Arg | Lys | Asp | Ser | Thr | Leu | Ser | Ile |
| | 1115 | | | | 1120 | | | | 1125 |
| Asn | Asn | Ile | Arg | Ser | Thr | Ile | Leu | Leu | Ala | Asn | Arg | Leu | Tyr | Ser |
| | 1130 | | | | 1135 | | | | 1140 |
| Gly | Ile | Lys | Val | Lys | Ile | Gln | Arg | Val | Asn | Asn | Ser | Ser | Thr | Asn |
| | 1145 | | | | 1150 | | | | 1155 |
| Asp | Asn | Leu | Val | Arg | Lys | Asn | Asp | Gln | Val | Tyr | Ile | Asn | Phe | Val |
| | 1160 | | | | 1165 | | | | 1170 |
| Ala | Ser | Lys | Thr | His | Leu | Phe | Pro | Leu | Tyr | Ala | Asp | Thr | Ala | Thr |
| | 1175 | | | | 1180 | | | | 1185 |
| Thr | Asn | Lys | Glu | Lys | Thr | Ile | Lys | Ile | Ser | Ser | Ser | Gly | Asn | Arg |
| | 1190 | | | | 1195 | | | | 1200 |
| Phe | Asn | Gln | Val | Val | Val | Met | Asn | Ser | Val | Gly | Asn | Asn | Cys | Thr |
| | 1205 | | | | 1210 | | | | 1215 |
| Met | Asn | Phe | Lys | Asn | Asn | Asn | Gly | Asn | Asn | Ile | Gly | Leu | Leu | Gly |
| | 1220 | | | | 1225 | | | | 1230 |
| Phe | Lys | Ala | Asp | Thr | Val | Val | Ala | Ser | Thr | Trp | Tyr | Tyr | Thr | His |
| | 1235 | | | | 1240 | | | | 1245 |
| Met | Arg | Asp | His | Thr | Asn | Ser | Asn | Gly | Cys | Phe | Trp | Asn | Phe | Ile |
| | 1250 | | | | 1255 | | | | 1260 |
| Ser | Glu | Glu | His | Gly | Trp | Gln | Glu | Lys |
| | 1265 | | | | 1270 |

<210> SEQ ID NO 81
<211> LENGTH: 3789
<212> TYPE: DNA
<213> ORGANISM: Clostridium botulinum

<400> SEQUENCE: 81

```
atgccgaaaa tcaacagctt caactataac gatccggtga cgatcgtac catcctgtat      60
attaaaccgg gcggttgcca ggaattttac aaaagcttca acatcatgaa aaacatctgg     120
attattccgg aacgtaacgt gattggcacc accccgcagg attttcatcc gccgaccagc     180
ctgaaaaacg gcgatagcag ctattatgat ccgaactatc tgcagtctga tgaagaaaaa     240
gatcgcttcc tgaaaatcgt gaccaaaatc ttcaaccgca tcaacaacaa cctgagcggc     300
ggcattctgc tggaagaact gagcaaagcg aatccgtatc tgggcaacga taacactcca     360
gataaccagt tcatattggt tgatgcgagc gcggtggaaa ttaaatttag caacggctct     420
caggacattc tgctgccgaa cgtgattatt atgggcgcgg aaccggacct gtttgaaacc     480
aacagcagca acattagcct gcgtaacaac tatatgccga gcaaccatgg ttttggcagc     540
attgcgattg tgaccttag cccggaatat agctttcgct tcaacgataa cagcatgaac     600
gaatttattc aggacccggc gctgaccctg atgcacgagc tgattcatag cctgcatggc     660
ctgtatggcg cgaaaggcat taccaccaaa tataccatca cccagaaaca gaatccgctg     720
```

```
attaccaaca ttcgtggcac caacattgaa gaatttctga cctttggcgg caccgatctg    780
aacattatta ccagcgcgca gagcaacgat atctatacca acctgctggc cgattataaa    840
aaaatcgcgt ctaaactgag caaagtgcag gtgagcaatc cgctgctgaa tccgtataaa    900
gatgtgtttg aagcgaaata tggcctggat aaagatgcta gcggcattta tagcgtgaac    960
atcaacaaat tcaacgacat cttcaaaaaa ctgtatagct ttaccgaatt tgatctggcc   1020
accaaatttc aggtgaaatg ccgccagacc tatattggcc agtataaata ttttaaactg   1080
agcaacctgc tgaacgatag catttacaac atcagcgaag gctataacat caacaacctg   1140
aaagtgaact tcgtggcca gaacgcgaat ttaaatccgc gtattattac cccgattacc   1200
ggccgtggac tagtgaaaaa aattatccgt ttttgcgtgc gtggcattat caccagcaaa   1260
accaaaagcc tggtgccgcg tggcagcaaa gcgttaaatg atttatgcat cgaaatcaac   1320
aacggcgaac tgttttttgt ggcgagcgaa aacagctata cgatgataa catcaacacc    1380
ccgaaagaaa ttgatgatac cgtgaccagc aataacaact acgaaaacga tctggatcag   1440
gtgattctga actttaacag cgaaagcgca ccgggcctgt ctgatgaaaa actgaacctg   1500
accattcaga cgatgcgta tatcccgaaa tatgatagca acggcaccag cgatattgaa    1560
cagcatgatg tgaacgaact gaacgtgttt ttttatctgg atgcgcagaa agtgccggaa   1620
ggcgaaaaca acgtgaatct gaccagctca attgataccg cgctgctgga acagccgaaa   1680
atctatacct tttttagcag cgaattcatc aacaacgtga acaaaccggt gcaggcggcg   1740
ctgtttgtga gctggattca gcaggtgctg gttgattta ccaccgaagc gaaccagaaa    1800
agcaccgtgg ataaaattgc ggatattagc attgtggtgc gtatattgg cctggccctg    1860
aacattggca cgaagcgca gaaaggcaac tttaaagatg cgctggaact gctgggtgcg    1920
ggcattctgc tggaatttga accggaactg ctgattccga ccattctggt gtttaccatc   1980
aaaagctttc tgggcagcag cgataacaaa acaaagtga tcaaagcgat taacaacgcg    2040
ctgaaagaac gtgatgaaaa atggaaagaa gtgtatagct tcattgtgtc taactggatg   2100
accaaaatca cacccagtt caacaaacgt aaagaacaaa tgtatcaggc gctgcagaac    2160
caggtgaacg cgattaaaac catcatcgaa agcaaataca acagctacac cctggaagaa   2220
aaaacgaac tgaccaacaa atatgacatc aaacaaatcg aaaatgaact gaaccagaaa    2280
gtgagcattg ccatgaacaa cattgatcgc tttctgaccg aaagcagcat tagctacctg   2340
atgaaactga tcaacgaagt gaaaatcaac aaactgcgcg aatatgatga aacgtgaaa    2400
acctacctgc tgaactatat tattcagcat ggcagcattc tgggcgaaag ccagcaagaa   2460
ctgaacagca tggttaccga taccctgaac aacagcattc cgtttaaact gagcagctac   2520
accgatgata aaatcctgat cagctacttc aacaaattct tcaaacgcat caaaagcagc   2580
agcgtgctga acatgcgtta taaaaacgat aaatacgtag ataccagcgg ctatgatagc   2640
aatatcaaca ttaacggtga tgtgtataaa tacccgacca caaaaaacca gttcggcatc   2700
tacaacgata aactgagcga agtgaacatt agccagaacg attatatcat ctacgataat   2760
aaatataaaa acttcagcat cagcttttgg gtgcgtattc cgaactacga taacaaaatc   2820
gtgaacgtga caacgaata caccatcatt aactgcatgc gtgataacaa cagcggctgg    2880
aaagtgagcc tgaaccataa cgaaatcatc tggaccctgc aggataacgc cggcattaac   2940
cagaaactgg cctttaacta tggcaacgcg aacggcatta gcgattacat caacaaatgg   3000
atctttgtga ccattaccaa cgatcgtctg ggcgatagca aactgtatat taacggcaac   3060
ctgatcgacc agaaaagcat tctgaacctg gcaacattc atgtgagcga taacatcctg   3120
```

```
ttcaaaattg tgaactgcag ctatacccgt tatattggca tccgctattt caacatcttc    3180
gataaagaac tggatgaaac cgaaattcag accctgtata gcaacgaacc gaacaccaac    3240
atcctgaaag atttctgggg caactatctg ctgtacgata agaatatta tctgctgaac    3300 gtgctgaaac cgaacaactt tattgatcgc cgtaaagata gcaccctgag cattaacaac    3360
attcgtagca ccattctgct ggccaaccgt ctgtatagcg gcattaaagt gaaaattcag    3420
cgcgtgaaca atagcagcac caacgataac ctggtgcgta aaaacgatca ggtgtatatc    3480
aactttgtgg ccagcaaaac ccacctgttt ccgctgtatg cggataccgc gaccaccaac    3540
aaagaaaaaa ccattaaaat cagcagcagc ggcaaccgtt ttaaccaggt ggtggtgatg    3600
aacagcgtgg gcaacaactg tacaatgaac ttcaaaaaca caacggcaa caacattggc    3660 ctgctgggct ttaaagcgga taccgtggtg cgcagcaccc tggtattatac ccacatgcgt    3720 gatcatacca acagcaacgg ctgcttttgg aactttatta gcgaagaaca tggctggcag    3780
gaaaaatga                                                             3789
```

<210> SEQ ID NO 82
<211> LENGTH: 1262
<212> TYPE: PRT
<213> ORGANISM: Clostridium botulinum

<400> SEQUENCE: 82

```
Met Pro Lys Ile Asn Ser Phe Asn Tyr Asn Asp Pro Val Asn Asp Arg
1               5                   10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205

Thr Leu Met His Glu Leu Ile His Ser Leu His Gly Leu Tyr Gly Ala
    210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
```

```
            245                 250                 255
Gly Thr Asp Leu Asn Ile Ile Thr Ser Ala Gln Ser Asn Asp Ile Tyr
            260                 265                 270

Thr Asn Leu Leu Ala Asp Tyr Lys Lys Ile Ala Ser Lys Leu Ser Lys
            275                 280                 285

Val Gln Val Ser Asn Pro Leu Leu Asn Pro Tyr Lys Asp Val Phe Glu
            290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
            370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Val Arg Gly Ile
                405                 410                 415

Ile Thr Ser Lys Thr Lys Ser Leu Val Pro Arg Gly Ser Lys Ala Leu
                420                 425                 430

Asn Asp Leu Cys Ile Glu Ile Asn Asn Gly Glu Leu Phe Phe Val Ala
            435                 440                 445

Ser Glu Asn Ser Tyr Asn Asp Asp Asn Ile Asn Thr Pro Lys Glu Ile
            450                 455                 460

Asp Asp Thr Val Thr Ser Asn Asn Asn Tyr Glu Asn Asp Leu Asp Gln
465                 470                 475                 480

Val Ile Leu Asn Phe Asn Ser Glu Ser Ala Pro Gly Leu Ser Asp Glu
                485                 490                 495

Lys Leu Asn Leu Thr Ile Gln Asn Asp Ala Tyr Ile Pro Lys Tyr Asp
                500                 505                 510

Ser Asn Gly Thr Ser Asp Ile Glu Gln His Asp Val Asn Glu Leu Asn
                515                 520                 525

Val Phe Phe Tyr Leu Asp Ala Gln Lys Val Pro Glu Gly Glu Asn Asn
            530                 535                 540

Val Asn Leu Thr Ser Ser Ile Asp Thr Ala Leu Leu Glu Gln Pro Lys
545                 550                 555                 560

Ile Tyr Thr Phe Phe Ser Ser Glu Phe Ile Asn Asn Val Asn Lys Pro
                565                 570                 575

Val Gln Ala Ala Leu Phe Val Ser Trp Ile Gln Gln Val Leu Val Asp
                580                 585                 590

Phe Thr Thr Glu Ala Asn Gln Lys Ser Thr Val Asp Lys Ile Ala Asp
                595                 600                 605

Ile Ser Ile Val Val Pro Tyr Ile Gly Leu Ala Leu Asn Ile Gly Asn
            610                 615                 620

Glu Ala Gln Lys Gly Asn Phe Lys Asp Ala Leu Glu Leu Leu Gly Ala
625                 630                 635                 640

Gly Ile Leu Leu Glu Phe Glu Pro Glu Leu Leu Ile Pro Thr Ile Leu
                645                 650                 655

Val Phe Thr Ile Lys Ser Phe Leu Gly Ser Ser Asp Asn Lys Asn Lys
                660                 665                 670
```

-continued

Val Ile Lys Ala Ile Asn Asn Ala Leu Lys Glu Arg Asp Glu Lys Trp
        675                 680                 685

Lys Glu Val Tyr Ser Phe Ile Val Ser Asn Trp Met Thr Lys Ile Asn
        690                 695                 700

Thr Gln Phe Asn Lys Arg Lys Glu Gln Met Tyr Gln Ala Leu Gln Asn
705                 710                 715                 720

Gln Val Asn Ala Ile Lys Thr Ile Ile Glu Ser Lys Tyr Asn Ser Tyr
            725                 730                 735

Thr Leu Glu Glu Lys Asn Glu Leu Thr Asn Lys Tyr Asp Ile Lys Gln
                740                 745                 750

Ile Glu Asn Glu Leu Asn Gln Lys Val Ser Ile Ala Met Asn Asn Ile
            755                 760                 765

Asp Arg Phe Leu Thr Glu Ser Ser Ile Ser Tyr Leu Met Lys Leu Ile
        770                 775                 780

Asn Glu Val Lys Ile Asn Lys Leu Arg Glu Tyr Asp Glu Asn Val Lys
785                 790                 795                 800

Thr Tyr Leu Leu Asn Tyr Ile Ile Gln His Gly Ser Ile Leu Gly Glu
                805                 810                 815

Ser Gln Gln Glu Leu Asn Ser Met Val Thr Asp Thr Leu Asn Asn Ser
        820                 825                 830

Ile Pro Phe Lys Leu Ser Ser Tyr Thr Asp Asp Lys Ile Leu Ile Ser
        835                 840                 845

Tyr Phe Asn Lys Phe Phe Lys Arg Ile Lys Ser Ser Ser Val Leu Asn
        850                 855                 860

Met Arg Tyr Lys Asn Asp Lys Tyr Val Asp Thr Ser Gly Tyr Asp Ser
865                 870                 875                 880

Asn Ile Asn Ile Asn Gly Asp Val Tyr Lys Tyr Pro Thr Asn Lys Asn
            885                 890                 895

Gln Phe Gly Ile Tyr Asn Asp Lys Leu Ser Glu Val Asn Ile Ser Gln
        900                 905                 910

Asn Asp Tyr Ile Ile Tyr Asp Asn Lys Tyr Lys Asn Phe Ser Ile Ser
        915                 920                 925

Phe Trp Val Arg Ile Pro Asn Tyr Asp Asn Lys Ile Val Asn Val Asn
        930                 935                 940

Asn Glu Tyr Thr Ile Ile Asn Cys Met Arg Asp Asn Asn Ser Gly Trp
945                 950                 955                 960

Lys Val Ser Leu Asn His Asn Glu Ile Ile Trp Thr Leu Gln Asp Asn
            965                 970                 975

Ala Gly Ile Asn Gln Lys Leu Ala Phe Asn Tyr Gly Asn Ala Asn Gly
            980                 985                 990

Ile Ser Asp Tyr Ile Asn Lys Trp Ile Phe Val Thr Ile Thr Asn Asp
        995                 1000                1005

Arg Leu Gly Asp Ser Lys Leu Tyr Ile Asn Gly Asn Leu Ile Asp
    1010                1015                1020

Gln Lys Ser Ile Leu Asn Leu Gly Asn Ile His Val Ser Asp Asn
    1025                1030                1035

Ile Leu Phe Lys Ile Val Asn Cys Ser Tyr Thr Arg Tyr Ile Gly
    1040                1045                1050

Ile Arg Tyr Phe Asn Ile Phe Asp Lys Glu Leu Asp Glu Thr Glu
    1055                1060                1065

Ile Gln Thr Leu Tyr Ser Asn Glu Pro Asn Thr Asn Ile Leu Lys
    1070                1075                1080

```
Asp Phe Trp Gly Asn Tyr Leu Leu Tyr Asp Lys Glu Tyr Tyr Leu
    1085            1090                1095

Leu Asn Val Leu Lys Pro Asn Asn Phe Ile Asp Arg Arg Lys Asp
    1100            1105                1110

Ser Thr Leu Ser Ile Asn Asn Ile Arg Ser Thr Ile Leu Leu Ala
    1115            1120                1125

Asn Arg Leu Tyr Ser Gly Ile Lys Val Lys Ile Gln Arg Val Asn
    1130            1135                1140

Asn Ser Ser Thr Asn Asp Asn Leu Val Arg Lys Asn Asp Gln Val
    1145            1150                1155

Tyr Ile Asn Phe Val Ala Ser Lys Thr His Leu Phe Pro Leu Tyr
    1160            1165                1170

Ala Asp Thr Ala Thr Thr Asn Lys Glu Lys Thr Ile Lys Ile Ser
    1175            1180                1185

Ser Ser Gly Asn Arg Phe Asn Gln Val Val Val Met Asn Ser Val
    1190            1195                1200

Gly Asn Asn Cys Thr Met Asn Phe Lys Asn Asn Asn Gly Asn Asn
    1205            1210                1215

Ile Gly Leu Leu Gly Phe Lys Ala Asp Thr Val Val Ala Ser Thr
    1220            1225                1230

Trp Tyr Tyr Thr His Met Arg Asp His Thr Asn Ser Asn Gly Cys
    1235            1240                1245

Phe Trp Asn Phe Ile Ser Glu Glu His Gly Trp Gln Glu Lys
    1250            1255                1260
```

UNITED STATES PATENT AND TRADEMARK OFFICE
CERTIFICATE OF CORRECTION

PATENT NO. : 9,809,809 B2
APPLICATION NO. : 14/356449
DATED : November 7, 2017
INVENTOR(S) : Michael Schmidt et al.

Page 1 of 1

It is certified that error appears in the above-identified patent and that said Letters Patent is hereby corrected as shown below:

In the Claims

Column 303, Line 48 in Claim 2: "LTFEHVVVVSS-" should read -- LTFEHWWSS- --

Column 303, Line 52 in Claim 2: "ETFEHVVWSQLLS" should read -- ETFEHWWSQLLS --

Column 304, Line 51 in Claim 9: "*coil*" should read -- *coli* --

Signed and Sealed this
Fifteenth Day of May, 2018

Andrei Iancu
*Director of the United States Patent and Trademark Office*